(12) United States Patent
Gill et al.

(10) Patent No.: US 10,851,161 B2
(45) Date of Patent: Dec. 1, 2020

(54) ANTIBODIES THAT BIND CELL SURFACE GRP78

(71) Applicant: University of Southern California, Los Angeles, CA (US)

(72) Inventors: Parkash Gill, Agoura, CA (US); Ren Liu, Azusa, CA (US); Amy Lee, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 16/438,289

(22) Filed: Jun. 11, 2019

(65) Prior Publication Data

US 2020/0140541 A1    May 7, 2020

Related U.S. Application Data

(60) Division of application No. 15/590,379, filed on May 9, 2017, now abandoned, which is a continuation of application No. 14/776,659, filed as application No. PCT/US2014/028868 on Mar. 14, 2014, now abandoned.

(60) Provisional application No. 61/781,395, filed on Mar. 14, 2013.

(51) Int. Cl.
| | |
|---|---|
| *C07K 16/28* | (2006.01) |
| *C07K 16/18* | (2006.01) |
| *C07K 16/30* | (2006.01) |
| *A61K 47/68* | (2017.01) |
| *A61K 39/00* | (2006.01) |
| *A61K 49/00* | (2006.01) |
| *G01N 33/574* | (2006.01) |

(52) U.S. Cl.
CPC .......... *C07K 16/28* (2013.01); *A61K 47/6803* (2017.08); *A61K 47/6849* (2017.08); *A61K 47/6851* (2017.08); *A61K 47/6898* (2017.08); *A61K 49/0032* (2013.01); *A61K 49/0058* (2013.01); *C07K 16/18* (2013.01); *C07K 16/30* (2013.01); *C07K 16/303* (2013.01); *C07K 16/3015* (2013.01); *C07K 16/3023* (2013.01); *C07K 16/3069* (2013.01); *G01N 33/57492* (2013.01); *A61K 2039/505* (2013.01); *C07K 2317/21* (2013.01); *C07K 2317/24* (2013.01); *C07K 2317/33* (2013.01); *C07K 2317/34* (2013.01); *C07K 2317/54* (2013.01); *C07K 2317/55* (2013.01); *C07K 2317/565* (2013.01); *C07K 2317/622* (2013.01); *C07K 2317/626* (2013.01); *C07K 2317/73* (2013.01); *C07K 2317/76* (2013.01); *C07K 2317/77* (2013.01); *C07K 2317/92* (2013.01); *C07K 2317/94* (2013.01); *G01N 2333/705* (2013.01)

(58) Field of Classification Search
None
See application file for complete search history.

(56) References Cited

U.S. PATENT DOCUMENTS

| | | |
|---|---|---|
| 2002/0039583 A1 | 4/2002 | Subjeck et al. |
| 2007/0077545 A1 | 4/2007 | Boilard et al. |
| 2010/0041074 A1 | 2/2010 | Kimura |
| 2010/0135904 A1 | 6/2010 | Gray et al. |
| 2011/0059111 A1 | 3/2011 | Ibrahim et al. |
| 2012/0189617 A1 | 7/2012 | Takayanagi et al. |
| 2013/0309664 A1 | 11/2013 | Duncan |
| 2016/0185853 A1 | 6/2016 | Gill et al. |

FOREIGN PATENT DOCUMENTS

| | | |
|---|---|---|
| WO | WO-99/12566 | 3/1999 |
| WO | WO-2010/088739 A1 | 8/2010 |
| WO | WO-2011/155607 | 12/2011 |

OTHER PUBLICATIONS

Arap M A et al. (2004), "Cell surface expression of the stress response chaperone GRP78 enables tumor targeting by circulating ligands", Cell, 3:275-284.

Dong D et al. (2008), "Critical Role of the Stress Chaperone GRP78/BiP in Tumor Proliferation, Survival, and Tumor Angiogenesis in Transgene-Induced Mammary Tumor Development", Cancer Res 2008, 68(2): 498-505.

Dong D et al. (2011), "A Critical Role for GRP78/BiP in the Tumor Microenvironment for Neovascularization During Tumor Growth and Metastasis", Cancer Res., 71(8): 2848-2857.

Extended European Search Report dated Dec. 13, 2016, from European application No. 14770483.7.

Fu Y et al. (2008), "Pten null prostate tumorigenesis and AKT activation are blocked by targeted knockout of ER chaperone GRP78/BiP in prostate epithelium", Proc. Natl. Acad. Sci. U.S.A., 49: 19444-19449.

Giusti, A.M. et al. (1987) "Somatic diversification of S107 from an antiphosphocholine to an anti-DNA autoantibody is due to a single base change in its heavy chain variable region," Proc. Natl. Acad. Sci. USA 84:2926-2930.

Goldenberg, D.M. et al. (2012) "Using antibodies to target cancer therapeutics," Expert Opinion on Biological Therapy 12(9):1173-1190.

(Continued)

*Primary Examiner* — Elly-Gerald Stoica
(74) *Attorney, Agent, or Firm* — Foley & Lardner LLP

(57) ABSTRACT

This application provides, inter alia, antibodies or antigen-binding fragments thereof, targeting cell surface GRP78 expressed on tumor cells, tumor endothelial cells, and tumor initiating cancer cells. These anti-GRP78 antibodies, or antigen-binding fragments thereof, have a high affinity for GRP78 and are less immunogenic compared to their unmodified parent antibodies in a given species, e.g., a human, and function to inhibit GRP78. Importantly, these isolated novel antibodies and antigen-binding fragments thereof, attenuate PI3K signaling and promote apoptosis in tumor cells, while leaving normal cells unaffected. The antibodies and antigen-binding fragments are useful for UPR-targeted cancer therapeutic treatments.

7 Claims, 18 Drawing Sheets

Specification includes a Sequence Listing.

(56) References Cited

OTHER PUBLICATIONS

Gonzalez-Gronow M et al. (2009), "GRP78: A Multifunctional Receptor on the Cell Surface", Antioxid. Redox Signal, 9:2299-2306.
Grant Award report titled "Stress Induction of Glucose Regulated Protein GRP78/BiP" (Feb. 6, 2009) [Retrieved from the Internet Dec. 15, 2014: <http://taggs.hhs.gov/readinesstool/AwardDetail508.cfm?STATE_CODE=6&s_RecipID=0AA4AE1FE9030D05ABD29E87&s_AwardDetail=3R01CA027607-29S1>], again retrieved from Internet on Jun. 8, 2016.
Gussow, D. et al. (1991) "Humanization of Monoclonal Antibodies," Methods in Enzymology 203:99-121.
Gustaaf De Ridder et al: "Cell-Surface GRP78 and its Antibodies: Pathologic and Therapeutic Roles in Cancer," Jan. 1, 2010, XP055201398.
Holm, P. et al. (2007) "Functional mapping and single chain construction of the anti-cytokeratin 8 monoclonal antibody TS1," Molecular Immunology 44:1075-1084.
International Search Report and Written Opinion for International Application No. PCT/US2014/028868 dated Dec. 1, 2014 (13 pages).
Lee A S (2007), "GRP78 Induction in Cancer: Therapeutic and Prognostic Implications", Cancer Res 2007, 67(8): 3496-3499.
Li X et al. (2011), "Unfolded protein response in cancer: the Physician's perspective", J Hematol Oncol, 4:8, pp. 1-10.
Li Z et al. (2012), "Glucose regulated protein 78: a critical link between tumor microenvironment and cancer hallmarks", Biochem. Biophys. Acta, 1:13-22.
Liu Y et al. (2007), "Mechanistic Studies of a Peptidic GRP78 Ligand for Cancer Cell-Specific Drug Delivery", Mol. Pharm., 4(3): 435-447.
Lloyd, et al., "Modelling the human immune response: performance of a 1011 human antibody repertoire against a broad panel of therapeutically relevant antigens", Protein Engineering, Design & Selection, vol. 22, No. 3, pp. 159-168, 2009.
Ma Y et al. (2004), "The Role of the Unfolded Protein Response in Tumour Development: Friend or Foe?", Cancer, 12:966-977.
Mariuzza, R.A. et al. (1987) "The Structural Basis of Antigen-Antibody Recognition," Ann. Rev. Biophys. Chem. 16:139-159.
Miharada K et al. (2011), "Cripto Regulates Hematopoietic Stem Cells as a Hypoxic-Niche-Related Factor through Cell Surface Receptor GRP78", Cell Stem Cell, 9(4):330-344.
Ni M et al. (2011), "Beyond the endoplasmic reticulum: atypical GRP78 in cell viability, signalling and therapeutic targeting", Biochem. J., 434(2): 181-188.
Non-Final Office Action dated Jul. 31, 2018, from U.S. Appl. No. 15/590,379.
Non-Final Office Action dated Sep. 13, 2016, from U.S. Appl. No. 14/776,659.
Notice of Allowance dated Feb. 9, 2017, from U.S. Appl. No. 14/776,659.
Notice of Allowance dated Apr. 12, 2019, from U.S. Appl. No. 15/590,379.
Notice of Allowance dated Mar. 12, 2019, from U.S. Appl. No. 15/590,379.
Pece S et al. (2010), "Biological and Molecular Heterogeneity of Breast Cancers Correlates with Their Cancer Stem Cell Content", Cell 140(1): 62-73.
Phaffenbach K T et al. (2011), "The critical role of GRP78 in physiologic and pathologic stress", Curr Opin Cell Biol. 2011, 23(2): 150-156.
Restriction Requirement in U.S. Appl. No. 14/776,659, dated May 17, 2016.
Rudikoff, S. et al. (1982) "Single amino acid substitution altering antigen-binding specificity," Proc. Natl. Acad. Sci. USA 79:1979-1983.
Sato M et al. (2010), "GRP78 signaling hub a receptor for targeted tumor therapy", Adv. Genet., 69: 97-114.
Takahashi H et al. (2011), "Overexpression of GRP78 and GRP94 is involved in colorectal carcinogenesis", Histol Histopathol., 26(6):663-671.
U. K. Misra et al: "Ligation of cancer cell surface GRP78 with antibodies directed against its COOH-terminal domain up-regulates p53 activity and promotes apoptosis," Molecular Cancer Therapeutics, vol. 8, No. 5, May 1, 2009, XP 055326239.
University of Southern California Award Report, "Stress Induction of Glucose Regulated Protein GRP78/BiP" (Feb. 6, 2009), retrieved from the Internet Dec. 15, 2014 (http://taggs.hhs.gov/readinesstool/AwardDetail508.cfm?STATE_CODE=6&s_RecipID=0AA4AE1FE9030D05ABD29E87&s_AwardDetail=3R01CA027607-29S1).
Zhang Y et al. (2610), "Cell Surface Relocalization of the Endoplasmic Reticulum Chaperone and Unfolded Protein Response Regulator GRP78/BiP", J. Biol. Chem. 2010, 285(20): 15065-15075.

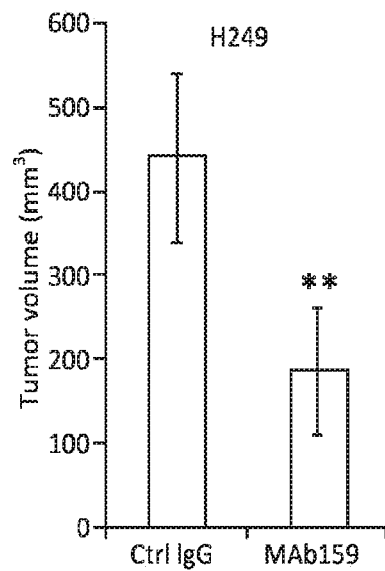
FIG. 4A
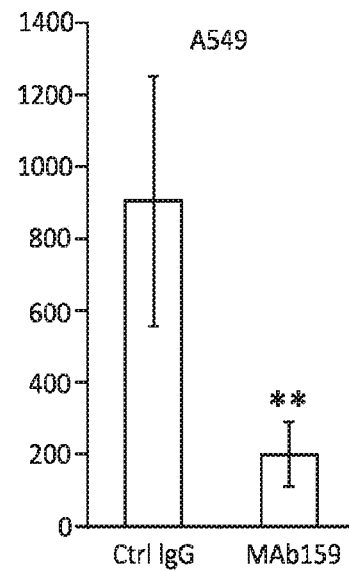
FIG. 4B
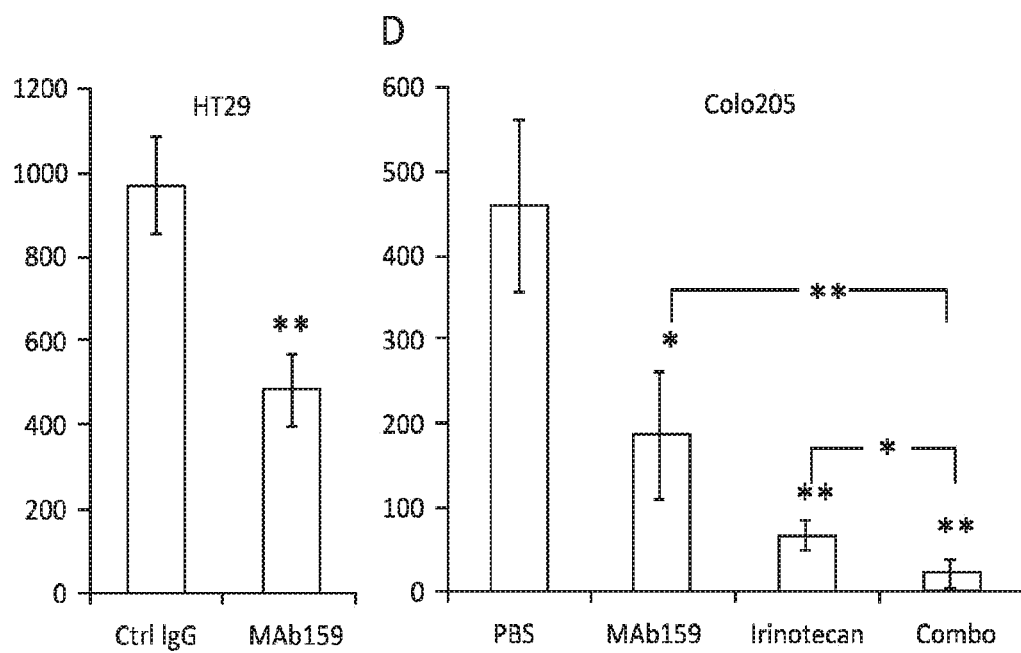
FIG. 4C
FIG. 4D

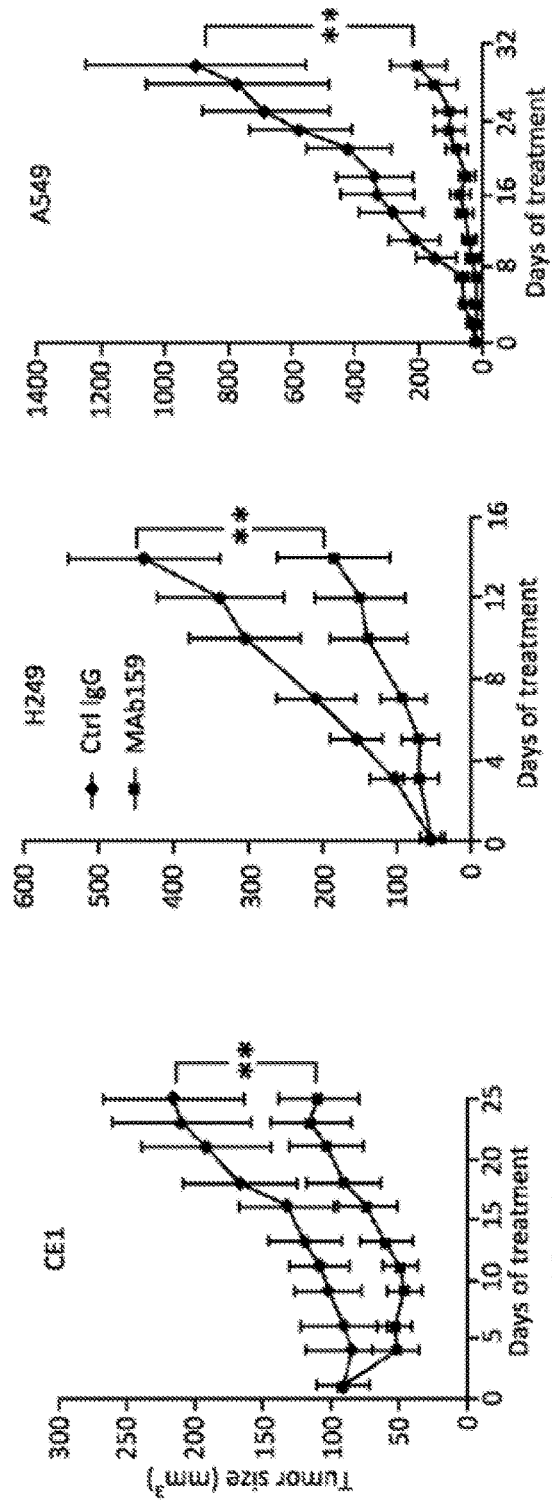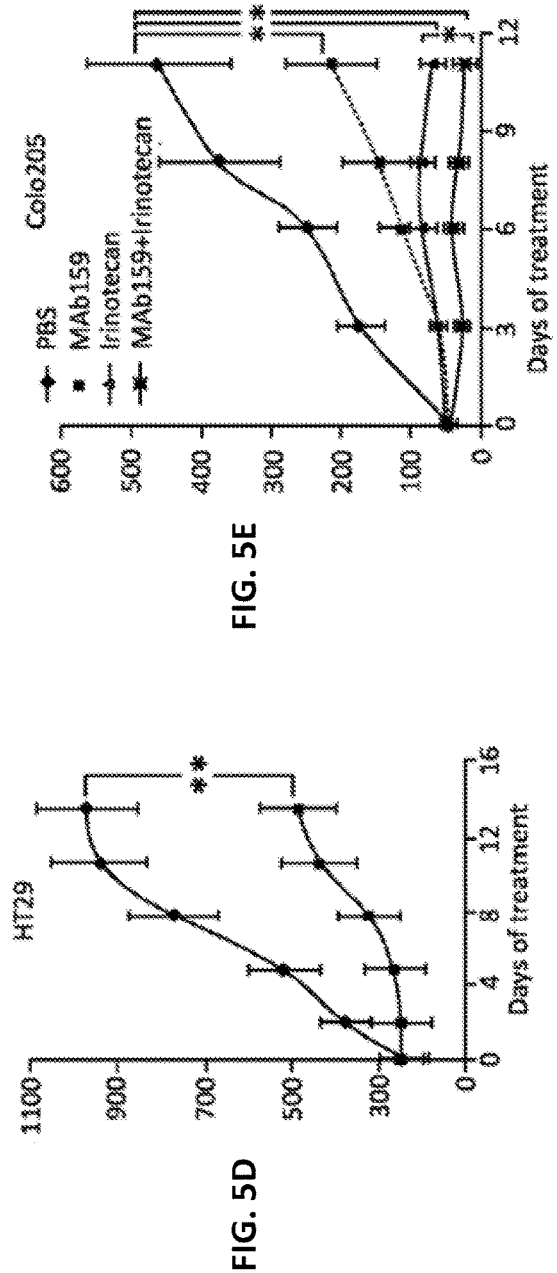
FIG. 5A
FIG. 5B
FIG. 5C
FIG. 5D
FIG. 5E

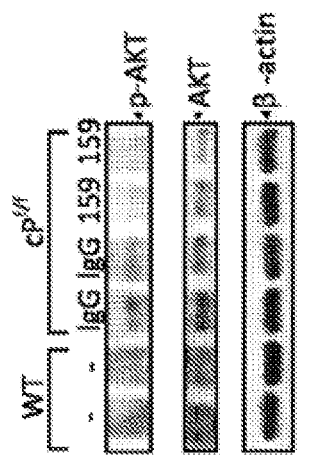
FIG. 6A
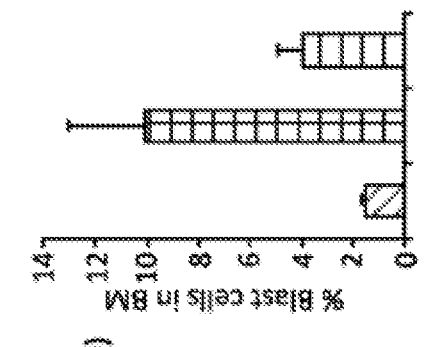
FIG. 6B
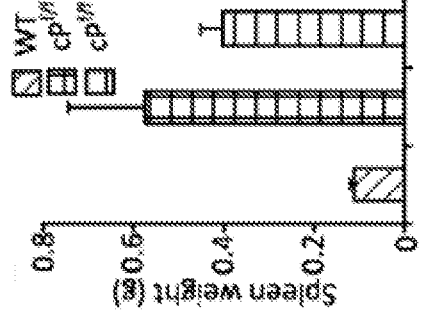
FIG. 6D
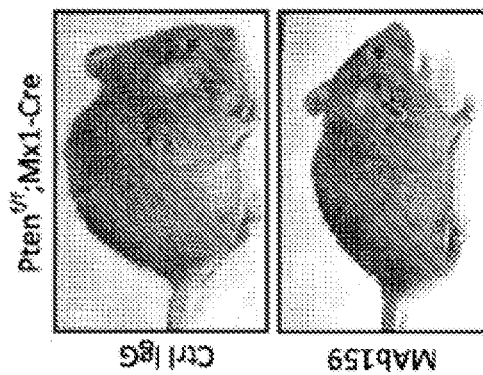
FIG. 6C
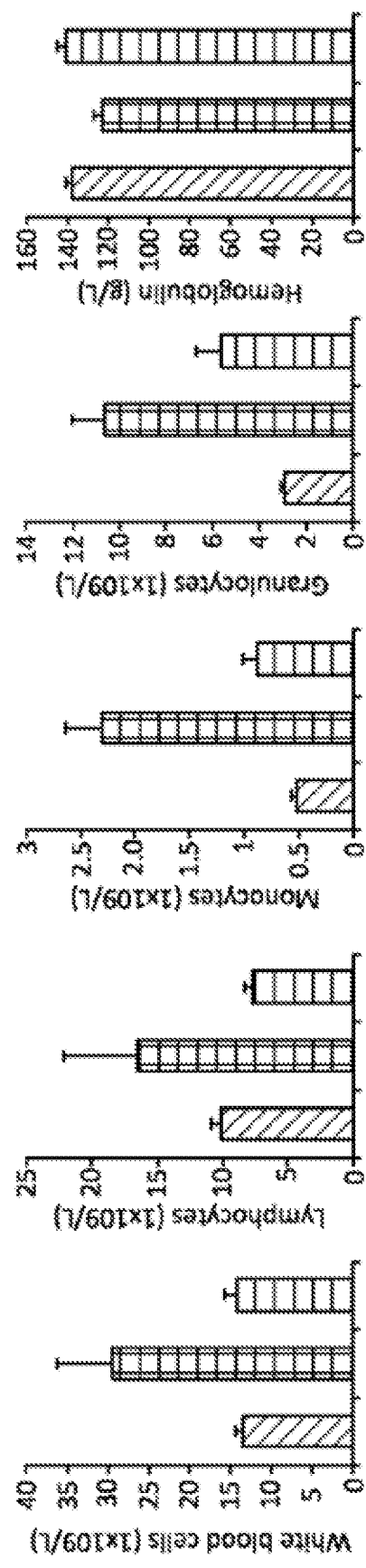

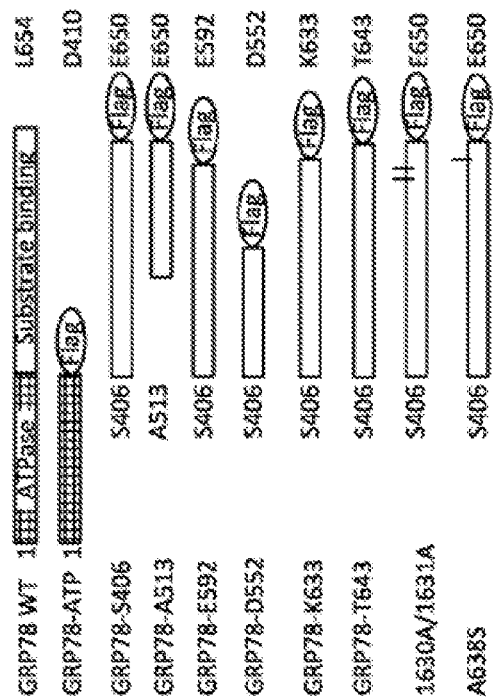
FIG. 14A
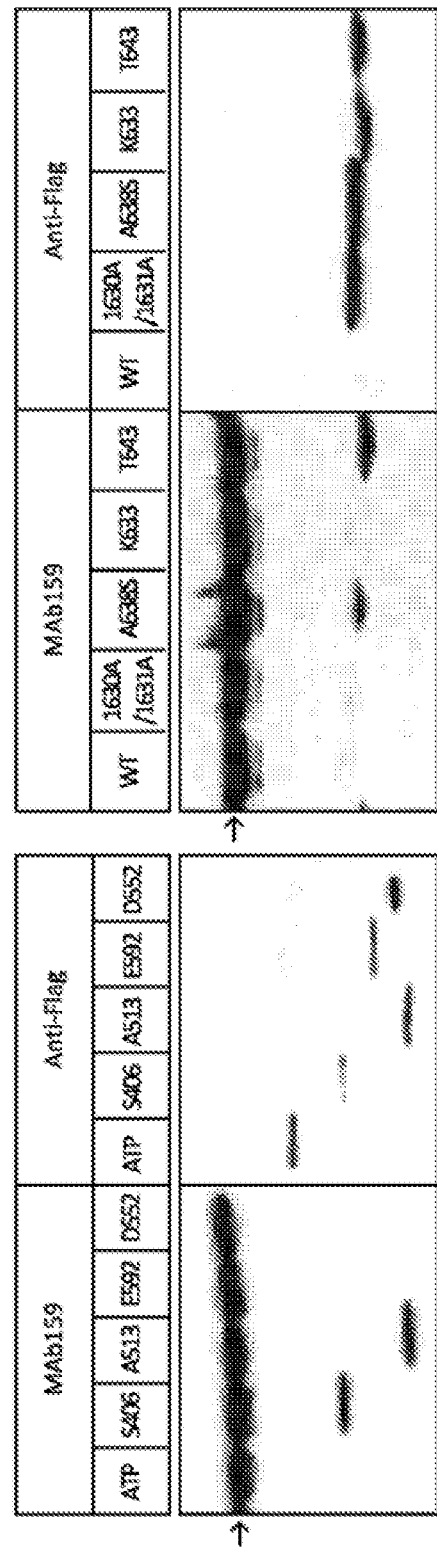
FIG. 14C
FIG. 14B

SEQUENCE LISTING

<160> NUMBER OF SEQ ID NOS: 36

<210> SEQ ID NO 1
<211> LENGTH: 654
<212> TYPE: PRT
<213> ORGANISM: Homo sapiens
<220> FEATURE:
<223> OTHER INFORMATION: Human cell surface GRP78 protein - amino acid
      residues 651-654 represent a C-terminal peptide

<400> SEQUENCE: 1

| Met | Lys | Leu | Ser | Leu | Val | Ala | Ala | Met | Leu | Leu | Leu | Leu | Ser | Ala | Ala |
| 1 | | | | 5 | | | | | 10 | | | | | 15 | |

| Arg | Ala | Glu | Glu | Glu | Asp | Lys | Lys | Glu | Asp | Val | Gly | Thr | Val | Val | Gly |
| | | | 20 | | | | | 25 | | | | | 30 | | |

| Ile | Asp | Leu | Gly | Thr | Thr | Tyr | Ser | Cys | Val | Gly | Val | Phe | Lys | Asn | Gly |
| | | | | 35 | | | | | 40 | | | | | 45 | |

| Arg | Val | Glu | Ile | Ile | Ala | Asn | Asp | Gln | Gly | Asn | Arg | Ile | Thr | Pro | Ser |
| | | 50 | | | | | 55 | | | | | 60 | | | |

| Tyr | Val | Ala | Phe | Thr | Pro | Glu | Gly | Glu | Arg | Leu | Ile | Gly | Asp | Ala | Ala |
| 65 | | | | | 70 | | | | | 75 | | | | | 80 |

| Lys | Asn | Gln | Leu | Thr | Ser | Asn | Pro | Glu | Asn | Thr | Val | Phe | Asp | Ala | Lys |

```
                     85                  90                  95
Arg Leu Ile Gly Arg Thr Trp Asn Asp Pro Ser Val Gln Gln Asp Ile
                100                 105                 110

Lys Phe Leu Pro Phe Lys Val Val Glu Lys Thr Lys Pro Tyr Ile
            115                 120                 125

Gln Val Asp Ile Gly Gly Gln Thr Lys Thr Phe Ala Pro Glu Glu
    130                 135                 140

Ile Ser Ala Met Val Leu Thr Lys Met Lys Glu Thr Ala Glu Ala Tyr
145                 150                 155                 160

Leu Gly Lys Lys Val Thr His Ala Val Thr Val Pro Ala Tyr Phe
                165                 170                 175

Asn Asp Ala Gln Arg Gln Ala Thr Lys Asp Ala Gly Thr Ile Ala Gly
                180                 185                 190

Leu Asn Val Met Arg Ile Ile Asn Glu Pro Thr Ala Ala Ala Ile Ala
                195                 200                 205

Tyr Gly Leu Asp Lys Arg Glu Gly Glu Lys Asn Ile Leu Val Phe Asp
    210                 215                 220

Leu Gly Gly Gly Thr Phe Asp Val Ser Leu Leu Thr Ile Asp Asn Gly
225                 230                 235                 240

Val Phe Glu Val Val Ala Thr Asn Gly Asp Thr His Leu Gly Gly Glu
                245                 250                 255

Asp Phe Asp Gln Arg Val Met Glu His Phe Ile Lys Leu Tyr Lys Lys
                260                 265                 270

Lys Thr Gly Lys Asp Val Arg Lys Asp Asn Arg Ala Val Gln Lys Leu
            275                 280                 285

Arg Arg Glu Val Glu Lys Ala Lys Arg Ala Leu Ser Ser Gln His Gln
    290                 295                 300

Ala Arg Ile Glu Ile Glu Ser Phe Tyr Glu Gly Glu Asp Phe Ser Glu
305                 310                 315                 320

Thr Leu Thr Arg Ala Lys Phe Glu Glu Leu Asn Met Asp Leu Phe Arg
                325                 330                 335

Ser Thr Met Lys Pro Val Gln Lys Val Leu Glu Asp Ser Asp Leu Lys
                340                 345                 350

Lys Ser Asp Ile Asp Glu Ile Val Leu Val Gly Gly Ser Thr Arg Ile
            355                 360                 365

Pro Lys Ile Gln Gln Leu Val Lys Glu Phe Phe Asn Gly Lys Glu Pro
    370                 375                 380

Ser Arg Gly Ile Asn Pro Asp Glu Ala Val Ala Tyr Gly Ala Ala Val
385                 390                 395                 400

Gln Ala Gly Val Leu Ser Gly Asp Gln Asp Thr Gly Asp Leu Val Leu
                405                 410                 415

Leu Asp Val Cys Pro Leu Thr Leu Gly Ile Glu Thr Val Gly Gly Val
                420                 425                 430

Met Thr Lys Leu Ile Pro Arg Asn Thr Val Val Pro Thr Lys Lys Ser
                435                 440                 445

Gln Ile Phe Ser Thr Ala Ser Asp Asn Gln Pro Thr Val Thr Ile Lys
    450                 455                 460

Val Tyr Glu Gly Glu Arg Pro Leu Thr Lys Asp Asn His Leu Leu Gly
465                 470                 475                 480

Thr Phe Asp Leu Thr Gly Ile Pro Pro Ala Pro Arg Gly Val Pro Gln
                485                 490                 495

Ile Glu Val Thr Phe Glu Ile Asp Val Asn Gly Ile Leu Arg Val Thr
                500                 505                 510
```

```
Ala Glu Asp Lys Gly Thr Gly Asn Lys Asn Lys Ile Thr Ile Thr Asn
        515                 520                 525
Asp Gln Asn Arg Leu Thr Pro Glu Glu Ile Glu Arg Met Val Asn Asp
        530                 535                 540
Ala Glu Lys Phe Ala Glu Glu Asp Lys Lys Leu Lys Glu Arg Ile Asp
545                 550                 555                 560
Thr Arg Asn Glu Leu Glu Ser Tyr Ala Tyr Ser Leu Lys Asn Gln Ile
                565                 570                 575
Gly Asp Lys Glu Lys Leu Gly Gly Lys Leu Ser Ser Glu Asp Lys Glu
            580                 585                 590
Thr Met Glu Lys Ala Val Glu Glu Lys Ile Glu Trp Leu Glu Ser His
        595                 600                 605
Gln Asp Ala Asp Ile Glu Asp Phe Lys Ala Lys Lys Lys Glu Leu Glu
    610                 615                 620
Glu Ile Val Gln Pro Ile Ile Ser Lys Leu Tyr Gly Ser Ala Gly Pro
625                 630                 635                 640
Pro Pro Thr Gly Glu Glu Asp Thr Ala Glu Lys Asp Glu Leu
                645                 650

<210> SEQ ID NO 2
<211> LENGTH: 1965
<212> TYPE: DNA
<213> ORGANISM: Homo sapiens
<220> FEATURE:
<223> OTHER INFORMATION: Nucleic acid encoding human cell surface GRP78
      protein residues 1-1950 represent the coding region

<400> SEQUENCE: 2
atgaagctct ccctggtggc cgcgatgctg ctgctgctca gcgcggcgcg ggccgaggag     60
gaggacaaga aggaggacgt gggcacggtg gtcggcatcg acctggggac cacctactcc    120
tgcgtcggcg tgttcaagaa cggccgcgtg gagatcatcg ccaacgatca gggcaaccgc    180
atcacgccgt cctatgtcgc cttcactcct gaaggggaac gtctgattgg cgatgccgcc    240
aagaaccagc tcacctccaa ccccgagaac acggtctttg acgccaagcg gctcatcggc    300
cgcacgtgga atgacccgtc tgtgcagcag gacatcaagt tcttgccgtt caaggtggtt    360
gaaaagaaaa ctaaaccata cattcaagtt gatattggag gtgggcaaac aaagacattt    420
gctcctgaag aaatttctgc catggttctc actaaaatga agaaaccgc tgaggcttat    480 ttgggaaaga aggttaccca tgcagttgtt actgtaccag cctattttaa tgatgcccaa    540
cgccaagcaa ccaaagacgc tggaactatt gctggcctaa atgttatgag gatcatcaac    600
gagcctacgg cagctgctat tgcttatggc ctggataaga gggaggggga agaacatc     660 ctggtgtttg acctgggtgg cggaaccttc gatgtgtctc ttctcaccat tgacaatggt    720
gtcttcgaag ttgtggccac taatggagat actcatctgg gtggagaaga ctttgaccag    780
cgtgtcatgg aacacttcat caaactgtac aaaaagaaga ccggcaaaga tgtcaggaaa    840
gacaatagag ctgtgcagaa actccggcgc gaggtagaaa aggccaaacg ggccctgtct    900
tctcagcatc aagcaagaat tgaaattgag tccttctatg aaggagaaga ctttttctgag    960 acccctgactc gggccaaatt tgaagagctc aacatggatc tgttccggtc tactatgaag   1020
cccgtccaga aagtgttgga agattctgat ttgaagaagt ctgatattga tgaaattgtt   1080
cttgttggtg gctcgactcg aattccaaag attcagcaac tggttaaaga gttcttcaat   1140
ggcaaggaac catcccgtgg cataaaccca gatgaagctg tagcgtatgg tgctgctgtc   1200
```

```
caggctggtg tgctctctgg tgatcaagat acaggtgacc tggtactgct tgatgtatgt    1260 cccccttacac ttggtattga aactgtggga ggtgtcatga ccaaactgat tccaaggaac   1320
acagtggtgc ctaccaagaa gtctcagatc tttctacag cttctgataa tcaaccaact     1380
gttacaatca aggtctatga aggtgaaaga cccctgacaa aagacaatca tcttctgggt    1440
acatttgatc tgactggaat tcctcctgct cctcgtgggg tcccacagat tgaagtcacc    1500
tttgagatag atgtgaatgg tattcttcga gtgacagctg aagacaaggg tacagggaac    1560
aaaaataaga tcacaatcac caatgaccag aatcgcctga cacctgaaga aatcgaaagg    1620
atggttaatg atgctgagaa gtttgctgag gaagacaaaa agctcaagga gcgcattgat    1680
actagaaatg agttggaaag ctatgcctat tctctaaaga atcagattgg agataaagaa    1740
aagctgggag gtaaactttc ctctgaagat aaggagacca tggaaaaagc tgtagaagaa    1800
aagattgaat ggctggaaag ccaccaagat gctgacattg aagacttcaa agctaagaag    1860
aaggaactgg aagaaattgt tcaaccaatt atcagcaaac tctatggaag tgcaggccct    1920 ccccccaactg gtgaagagga tacagcagaa aaagatgagt tgtag                   1965
```

<210> SEQ ID NO 3
<211> LENGTH: 5
<212> TYPE: PRT
<213> ORGANISM: Mus sp.
<220> FEATURE:
<223> OTHER INFORMATION: Murine MAb159 heavy chain CDR1 protein sequence

<400> SEQUENCE: 3

Ser Tyr Trp Met His
1               5

<210> SEQ ID NO 4
<211> LENGTH: 17
<212> TYPE: PRT
<213> ORGANISM: Mus sp.
<220> FEATURE:
<223> OTHER INFORMATION: Murine MAb159 heavy chain CDR2 protein sequence

<400> SEQUENCE: 4

Glu Ile Asn Pro Gly Asn Gly Arg Thr Asn Tyr Asn Glu Lys Phe Lys
1               5                   10                  15

Arg

<210> SEQ ID NO 5
<211> LENGTH: 10
<212> TYPE: PRT
<213> ORGANISM: Mus sp.
<220> FEATURE:
<223> OTHER INFORMATION: Murine MAb159 heavy chain CDR3 protein sequence

<400> SEQUENCE: 5

Leu Tyr Tyr Tyr Asp Gly Thr Tyr Asp Tyr
1               5                   10

<210> SEQ ID NO 6
<211> LENGTH: 11
<212> TYPE: PRT
<213> ORGANISM: Mus sp.
<220> FEATURE:
<223> OTHER INFORMATION: Murine MAb159 light chain CDR1 protein sequence

<400> SEQUENCE: 6

Lys Ala Ser Gln Asn Val Gly Thr Asp Val Ala
1               5                   10

<210> SEQ ID NO 7
<211> LENGTH: 7
<212> TYPE: PRT
<213> ORGANISM: Mus sp.
<220> FEATURE:
<223> OTHER INFORMATION: Murine MAb159 light chain CDR2 protein sequence

<400> SEQUENCE: 7

Trp Ala Ser Asn Arg Phe Thr
1               5

<210> SEQ ID NO 8
<211> LENGTH: 9
<212> TYPE: PRT
<213> ORGANISM: Mus sp.
<220> FEATURE:
<223> OTHER INFORMATION: Murine MAb159 light chain CDR3 protein sequence

<400> SEQUENCE: 8

Gln Gln Tyr Ser Ser Ser Pro Trp Thr
1               5

<210> SEQ ID NO 9
<211> LENGTH: 119
<212> TYPE: PRT
<213> ORGANISM: Mus sp.
<220> FEATURE:
<223> OTHER INFORMATION: Murine MAb159 heavy chain variable region
      protein sequence

<400> SEQUENCE: 9

Gln Ala Gln Leu Gln Gln Pro Gly Ala Glu Leu Val Lys Pro Gly Ala
1               5                   10                  15

Ser Val Arg Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Gly Asn Gly Arg Thr Asn Tyr Asn Glu Lys Phe
    50                  55                  60

Lys Arg Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Thr Leu Tyr Tyr Tyr Asp Gly Thr Tyr Asp Tyr Trp Gly Gln Gly
            100                 105                 110

Thr Thr Leu Thr Val Ser Ser
        115

<210> SEQ ID NO 10
<211> LENGTH: 357
<212> TYPE: DNA
<213> ORGANISM: Mus sp.
<220> FEATURE:
<223> OTHER INFORMATION: Nucleic acid encoding murine MAb159 heavy chain
      variable region

<400> SEQUENCE: 10
caggcccaac tgcagcagcc tggggctgaa ctggtgaagc ctggggcttc agtgaggctg        60
tcctgcaagg cttctggtta ccttcacc agctactgga tgcactgggt gaagcagagg       120
cctggacaag gccttgagtg gattggagag attaatcctg gcaacggtcg tactaactac       180

```
aatgagaagt tcaagagaaa ggccacactg actgtagaca atcctccag cacagcctac    240 atgcaactca acagcctgac atctgaggac tctgcggtct attactgtgc aacccttat    300 tactacgatg gtacttacga ctactggggc caaggcacca ctctcacagt ctcctca     357
```

<210> SEQ ID NO 11
<211> LENGTH: 107
<212> TYPE: PRT
<213> ORGANISM: Mus sp.
<220> FEATURE:
<223> OTHER INFORMATION: Murine MAb159 light chain variable region
      protein sequence

<400> SEQUENCE: 11

```
Asp Ile Val Met Thr Gln Ser His Lys Phe Met Ser Thr Ser Val Gly
1               5                   10                  15

Asp Arg Val Ser Val Thr Cys Lys Ala Ser Gln Asn Val Gly Thr Asp
            20                  25                  30

Val Ala Trp Tyr Gln Gln Lys Pro Gly Gln Ser Pro Lys Ala Leu Ile
        35                  40                  45

Tyr Trp Ala Ser Asn Arg Phe Thr Gly Val Pro Asp Arg Phe Thr Gly
    50                  55                  60

Ser Gly Ser Gly Thr Asp Phe Thr Leu Thr Ile Asn Asn Val Gln Ser
65                  70                  75                  80

Glu Asp Leu Val Asp Tyr Phe Cys Gln Gln Tyr Ser Ser Ser Pro Trp
                85                  90                  95

Thr Phe Gly Gly Gly Thr Lys Leu Glu Ile Lys
            100                 105
```

<210> SEQ ID NO 12
<211> LENGTH: 321
<212> TYPE: DNA
<213> ORGANISM: Mus sp.
<220> FEATURE:
<223> OTHER INFORMATION: Nucleic acid encoding murine MAb159 light chain
      variable region

<400> SEQUENCE: 12

```
gacattgtga tgacccagtc tcacaaattc atgtccacat cagtaggaga cagggtcagc    60
gtcacctgca aggccagtca gaatgtgggt actgatgtag cctggtatca acagaaacca   120
gggcaatctc ctaaagcact gatttactgg gcatccaacc ggttcactgg agtccctgat   180
cgcttcacag gcagtggatc tgggacagat ttcactctca ccattaacaa tgtgcagtct   240
gaagacttag tagattattt ctgtcagcaa tatagcagct ctccgtggac gttcggtgga   300
ggcaccaagc tggaaatcaa a                                             321
```

<210> SEQ ID NO 13
<211> LENGTH: 119
<212> TYPE: PRT
<213> ORGANISM: Artificial Sequence
<220> FEATURE:
<223> OTHER INFORMATION: Description of Artificial Sequence: Synthetic
      Humanized GRP78 antibody heavy chain variable region protein
      sequence

<400> SEQUENCE: 13

```
Gln Ala Gln Leu Val Gln Ser Gly Ala Glu Leu Lys Lys Pro Gly Ala
1               5                   10                  15

Ser Val Lys Leu Ser Cys Lys Ala Ser Gly Tyr Thr Phe Thr Ser Tyr
            20                  25                  30
```

Trp Met His Trp Val Lys Gln Ala Pro Gly Gln Gly Leu Glu Trp Ile
            35                  40                  45

Gly Glu Ile Asn Pro Gly Asn Gly Arg Thr Asn Tyr Asn Glu Lys Phe
 50                  55                  60

Lys Arg Arg Ala Thr Leu Thr Val Asp Lys Ser Ala Ser Thr Ala Tyr
 65                  70                  75                  80

Met Glu Leu Ser Ser Leu Arg Ser Glu Asp Ser Ala Val Tyr Tyr Cys
                 85                  90                  95

Ala Thr Leu Tyr Tyr Tyr Asp Gly Thr Tyr Asp Tyr Trp Gly Gln Gly
                100                 105                 110

Thr Thr Val Thr Val Ser Ser
            115

<210> SEQ ID NO 14
<211> LENGTH: 357
<212> TYPE: DNA
<213> ORGANISM: Artificial Sequence
<220> FEATURE:
<223> OTHER INFORMATION: Description of Artificial Sequence: Synthetic
      Nucleic acid encoding a humanized GRP78 antibody heavy chain
      variable region

<400> SEQUENCE: 14
caggcccagc tggtgcagtc tggcgccgag ctgaagaaac ctggcgcctc cgtgaagctg      60
tcctgcaagg cctccggcta caccttcacc agctactgga tgcactgggt gaaacaggcc    120
ccaggccagg gactggaatg gatcggcgag atcaaccccg gcaacggccg gaccaactac    180
aacgagaagt tcaagcggag agccaccctg accgtggaca gtccgcctc caccgcctac    240 atggaactgt cctccctgcg gagcgaggac tccgccgtgt actactgcgc caccctgtac    300
tactacgacg gcacctacga ctactggggc cagggcacca ccgtgaccgt gtctagc       357

<210> SEQ ID NO 15
<211> LENGTH: 119
<212> TYPE: PRT
<213> ORGANISM: Artificial Sequence
<220> FEATURE:
<223> OTHER INFORMATION: Description of Artificial Sequence: Synthetic
      Humanized GRP78 antibody heavy chain variable region protein
      sequence

<400> SEQUENCE: 15

Gln Ala Gln Leu Val Gln Ser Gly Ala Glu Val Lys Lys Pro Gly Ala
 1               5                  10                  15

Ser Val Lys Leu Ser Cys Lys Ala Ser Gly Tyr Thr Phe Thr Ser Tyr
             20                  25                  30

Trp Met His Trp Val Lys Gln Ala Pro Gly Gln Gly Leu Glu Trp Ile
            35                  40                  45

Gly Glu Ile Asn Pro Gly Asn Gly Arg Thr Asn Tyr Asn Glu Lys Phe
 50                  55                  60

Lys Arg Arg Ala Thr Leu Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Thr Leu Tyr Tyr Tyr Asp Gly Thr Tyr Asp Tyr Trp Gly Gln Gly
                100                 105                 110

Thr Thr Val Thr Val Ser Ser
            115

<210> SEQ ID NO 16
<211> LENGTH: 357
<212> TYPE: DNA
<213> ORGANISM: Artificial Sequence
<220> FEATURE:
<223> OTHER INFORMATION: Description of Artificial Sequence: Synthetic
      Nucleic acid encoding a humanized GRP78 antibody heavy chain
      variable region

<400> SEQUENCE: 16
caggcccagc tggtgcagtc tggcgccgag gtgaagaaac ctggcgcctc cgtgaagctg      60
tcctgcaagg cctccggcta caccttcacc agctactgga tgcactgggt gaaacaggcc     120
ccaggccagg gactggaatg gatcggcgag atcaacccg gcaacggccg gaccaactac      180
aacgagaagt tcaagcggag agccaccctg accgtggaca gtccgcctc caccgcctac      240 atggaactgt cctccctgcg gagcgaggac accgccgtgt actactgcgc cacccctgtac    300 tactacgacg gcacctacga ctactggggc cagggcacca ccgtgaccgt gtctagc        357

<210> SEQ ID NO 17
<211> LENGTH: 119
<212> TYPE: PRT
<213> ORGANISM: Artificial Sequence
<220> FEATURE:
<223> OTHER INFORMATION: Description of Artificial Sequence: Synthetic
      Humanized GRP78 antibody heavy chain variable region protein
      sequence

<400> SEQUENCE: 17

Gln Ala Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Glu Ile Asn Pro Gly Asn Gly Arg Thr Asn Tyr Asn Glu Lys Phe
    50                  55                  60

Lys Arg Arg Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Leu Tyr Tyr Tyr Asp Gly Thr Tyr Asp Tyr Trp Gly Gln Gly
            100                 105                 110

Thr Thr Val Thr Val Ser Ser
        115

<210> SEQ ID NO 18
<211> LENGTH: 357
<212> TYPE: DNA
<213> ORGANISM: Artificial Sequence
<220> FEATURE:
<223> OTHER INFORMATION: Description of Artificial Sequence: Synthetic
      Nucleic acid encoding a humanized GRP78 antibody heavy chain
      variable region

<400> SEQUENCE: 18
caggcccagc tggtgcagtc tggcgccgag gtgaagaaac ctggcgcctc cgtgaagctg      60
tcctgcaagg cctccggcta caccttcacc agctactgga tgcactgggt gcggcaggcc     120
ccaggccagg gactggaatg gatcggcgag atcaacccg gcaacggccg gaccaactac      180
aacgagaagt tcaagcggag agccaccctg accgtggaca gtccgcctc caccgcctac      240

```
atggaactgt cctccctgcg gagcgaggac accgccgtgt actactgcgc caccctgtac      300
tactacgacg gcacctacga ctactggggc cagggcacca ccgtgaccgt gtctagc          357
```

<210> SEQ ID NO 19
<211> LENGTH: 119
<212> TYPE: PRT
<213> ORGANISM: Artificial Sequence
<220> FEATURE:
<223> OTHER INFORMATION: Description of Artificial Sequence: Synthetic
      Humanized GRP78 antibody heavy chain variable region protein
      sequence

<400> SEQUENCE: 19

Gln Ala Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Glu Ile Asn Pro Gly Asn Gly Arg Thr Asn Tyr Asn Glu Lys Phe
    50                  55                  60

Lys Arg Arg Ala Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Leu Tyr Tyr Tyr Asp Gly Thr Tyr Asp Tyr Trp Gly Gln Gly
            100                 105                 110

Thr Thr Val Thr Val Ser Ser
        115

<210> SEQ ID NO 20
<211> LENGTH: 357
<212> TYPE: DNA
<213> ORGANISM: Artificial Sequence
<220> FEATURE:
<223> OTHER INFORMATION: Description of Artificial Sequence: Synthetic
      Nucleic acid encoding a humanized GRP78 antibody heavy chain
      variable region

<400> SEQUENCE: 20

```
caggcccagc tggtgcagtc tggcgccgag gtgaagaaac ctggcgcctc cgtgaaggtg      60
tcctgcaagg cctccggcta caccttcacc agctactgga tgcactgggt gcggcaggcc     120
ccaggccagg gactggaatg gatcggcgag atcaacccg gcaacggccg gaccaactac      180
aacgagaagt tcaagcggag agccaccatc accgtggaca gtccgcctc caccgcctac      240 atggaactgt cctccctgcg gagcgaggac accgccgtgt actactgcgc caccctgtac     300
tactacgacg gcacctacga ctactggggc cagggcacca ccgtgaccgt gtctagc         357
```

<210> SEQ ID NO 21
<211> LENGTH: 119
<212> TYPE: PRT
<213> ORGANISM: Artificial Sequence
<220> FEATURE:
<223> OTHER INFORMATION: Description of Artificial Sequence: Synthetic
      Humanized GRP78 antibody heavy chain variable region protein
      sequence

<400> SEQUENCE: 21

Gln Ala Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
            35                  40                  45

Gly Glu Ile Asn Pro Gly Asn Gly Arg Thr Asn Tyr Asn Glu Lys Phe
50                  55                  60

Lys Arg Arg Val Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Ala Thr Leu Tyr Tyr Tyr Asp Gly Thr Tyr Asp Tyr Trp Gly Gln Gly
            100                 105                 110

Thr Thr Val Thr Val Ser Ser
            115

<210> SEQ ID NO 22
<211> LENGTH: 356
<212> TYPE: DNA
<213> ORGANISM: Artificial Sequence
<220> FEATURE:
<223> OTHER INFORMATION: Description of Artificial Sequence: Synthetic
      Nucleic acid encoding a humanized GRP78 antibody heavy chain
      variable region

<400> SEQUENCE: 22
caggcccagc tggtgcagtc tggcgccgag gtgaagaaac ctggcgcctc cgtgaaggtg      60
tcctgcaagg cctccggcta accttcacca gctactggat gcactgggtg cggcaggccc    120
caggccaggg actggaatgg atcggcgaga tcaaccccgg caacggccgg accaactaca    180
acgagaagtt caagcggaga gtgaccatca ccgtggacaa gtccgcctcc accgcctaca    240
tggaactgtc ctccctgcgg agcgaggaca ccgccgtgta ctactgcgcc accctgtact    300
actacgacgg cacctacgac tactggggcc agggcaccac cgtgaccgtg tctagc        356

<210> SEQ ID NO 23
<211> LENGTH: 107
<212> TYPE: PRT
<213> ORGANISM: Artificial Sequence
<220> FEATURE:
<223> OTHER INFORMATION: Description of Artificial Sequence: Synthetic
      Humanized GRP78 antibody light chain variable region protein
      sequence

<400> SEQUENCE: 23

Asp Ile Val Met Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Asp
            20                  25                  30

Val Ala Trp Tyr Gln Gln Lys Pro Gly Lys Ala Pro Lys Ala Leu Ile
            35                  40                  45

Tyr Trp Ala Ser Asn Arg Phe Thr Gly Val Pro Asp Arg Phe Thr Gly
            50                  55                  60

Ser Gly Ser Gly Thr Asp Phe Thr Leu Thr Ile Ser Ser Leu Gln Ser
65                  70                  75                  80

Glu Asp Val Ala Asp Tyr Phe Cys Gln Gln Tyr Ser Ser Ser Pro Trp
            85                  90                  95

Thr Phe Gly Gly Gly Thr Lys Val Glu Ile Lys
            100                 105

```
<210> SEQ ID NO 24
<211> LENGTH: 321
<212> TYPE: DNA
<213> ORGANISM: Artificial Sequence
<220> FEATURE:
<223> OTHER INFORMATION: Description of Artificial Sequence: Synthetic
      Nucleic acid encoding a humanized GRP78 antibody light chain
      variable region

<400> SEQUENCE: 24
gacatcgtga tgacccagtc ccccagcttc ctgtccgcct ccgtgggcga cagagtgacc    60
atcacatgca aggcctccca gaacgtgggc accgacgtgg cctggtatca gcagaagccc   120
ggcaaggccc ccaaggccct gatctactgg gcctccaacc ggttcaccgg cgtgcccgac   180
agattcaccg gctctggctc cggcaccgac ttcaccctga ccatctccag cctgcagtcc   240
gaggacgtgg ccgactactt ctgccagcag tactcctcca gcccctggac cttcggcgga   300
ggcaccaagg tggaaatcaa g                                             321

<210> SEQ ID NO 25
<211> LENGTH: 107
<212> TYPE: PRT
<213> ORGANISM: Artificial Sequence
<220> FEATURE:
<223> OTHER INFORMATION: Description of Artificial Sequence: Synthetic
      Humanized GRP78 antibody light chain variable region protein
      sequence

<400> SEQUENCE: 25

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asp
            20                  25                  30

Val Ala Trp Tyr Gln Gln Lys Pro Gly Lys Ala Pro Lys Ala Leu Ile
        35                  40                  45

Tyr Trp Ala Ser Asn Arg Phe Thr Gly Val Pro Asp Arg Phe Thr Gly
    50                  55                  60

Ser Gly Ser Gly Thr Asp Phe Thr Leu Thr Ile Ser Ser Leu Gln Ala
65                  70                  75                  80

Glu Asp Val Ala Asp Tyr Phe Cys Gln Gln Tyr Ser Ser Ser Pro Trp
                85                  90                  95

Thr Phe Gly Gly Gly Thr Lys Val Glu Ile Lys
            100                 105

<210> SEQ ID NO 26
<211> LENGTH: 321
<212> TYPE: DNA
<213> ORGANISM: Artificial Sequence
<220> FEATURE:
<223> OTHER INFORMATION: Description of Artificial Sequence: Synthetic
      Nucleic acid encoding a humanized GRP78 antibody light chain
      variable region

<400> SEQUENCE: 26
gacatcgtga tgacccagtc ccccagctcc ctgtccgcct ccgtgggcga cagagtgacc    60
atcacatgca aggcctccca gaacgtgggc accgacgtgg cctggtatca gcagaagccc   120
ggcaaggccc ccaaggccct gatctactgg gcctccaacc ggttcaccgg cgtgcccgac   180
agattcaccg gctctggctc cggcaccgac ttcaccctga ccatctccag cctgcaggcc   240
gaggacgtgg ccgactactt ctgccagcag tactcctcca gcccctggac cttcggcgga   300
ggcaccaagg tggaaatcaa g                                             321
```

<210> SEQ ID NO 27
<211> LENGTH: 107
<212> TYPE: PRT
<213> ORGANISM: Artificial Sequence
<220> FEATURE:
<223> OTHER INFORMATION: Description of Artificial Sequence: Synthetic
      Humanized GRP78 antibody light chain variable region protein
      sequence

<400> SEQUENCE: 27

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asp
            20                  25                  30

Val Ala Trp Tyr Gln Gln Lys Pro Gly Lys Ala Pro Lys Ala Leu Ile
        35                  40                  45

Tyr Trp Ala Ser Asn Arg Phe Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Asp Tyr Phe Cys Gln Gln Tyr Ser Ser Ser Pro Trp
                85                  90                  95

Thr Phe Gly Gly Gly Thr Lys Val Glu Ile Lys
            100                 105

<210> SEQ ID NO 28
<211> LENGTH: 321
<212> TYPE: DNA
<213> ORGANISM: Artificial Sequence
<220> FEATURE:
<223> OTHER INFORMATION: Description of Artificial Sequence: Synthetic
      Nucleic acid encoding a humanized GRP78 antibody light chain
      variable region

<400> SEQUENCE: 28
gacatcgtga tgacccagtc ccccagctcc ctgtccgcct ccgtgggcga cagagtgacc      60
atcacatgca aggcctccca gaacgtgggc accgacgtgg cctggtatca gcagaagccc     120
ggcaaggccc ccaaggccct gatctactgg gcctccaacc ggttcaccgg cgtgcccgac     180
agattctccg gctctggctc cggcaccgac ttcaccctga ccatctccag cctgcaggcc     240
gaggacgtgg ccgactactt ctgccagcag tactcctcca gcccctggac cttcggcgga     300
ggcaccaagg tggaaatcaa g                                              321

<210> SEQ ID NO 29
<211> LENGTH: 107
<212> TYPE: PRT
<213> ORGANISM: Artificial Sequence
<220> FEATURE:
<223> OTHER INFORMATION: Description of Artificial Sequence: Synthetic
      Humanized GRP78 antibody light chain variable region protein
      sequence

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asp
            20                  25                  30

Val Ala Trp Tyr Gln Gln Lys Pro Gly Lys Ala Pro Lys Ala Leu Ile
        35                  40                  45

```
Tyr Trp Ala Ser Asn Arg Phe Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Asp Tyr Phe Cys Gln Gln Tyr Ser Ser Ser Pro Trp
                85                  90                  95

Thr Phe Gly Gly Gly Thr Lys Val Glu Ile Lys
            100                 105
```

<210> SEQ ID NO 30
<211> LENGTH: 321
<212> TYPE: DNA
<213> ORGANISM: Artificial Sequence
<220> FEATURE:
<223> OTHER INFORMATION: Description of Artificial Sequence: Synthetic
      Nucleic acid encoding a humanized GRP78 antibody light chain
      variable region

<400> SEQUENCE: 30

```
gacatccaga tgacccagtc ccccagctcc ctgtccgcct ccgtgggcga cagagtgacc    60
atcacatgca aggcctccca gaacgtgggc accgacgtgg cctggtatca gcagaagccc   120
ggcaaggccc ccaaggccct gatctactgg gcctccaacc ggttcaccgg cgtgcccgac   180
agattctccg gctctggctc cggcaccgac ttcaccctga ccatctccag cctgcaggcc   240
gaggacgtgg ccgactactt ctgccagcag tactcctcca gcccctggac cttcggcgga   300
ggcaccaagg tggaaatcaa g                                             321
```

<210> SEQ ID NO 31
<211> LENGTH: 29
<212> TYPE: PRT
<213> ORGANISM: Artificial Sequence
<220> FEATURE:
<223> OTHER INFORMATION: Description of Artificial Sequence: Synthetic
      GRP78 peptide sequence

<400> SEQUENCE: 31

```
Gln Asp Ala Asp Ile Glu Asp Phe Lys Ala Lys Lys Lys Glu Leu Glu
1               5                   10                  15

Glu Ile Val Gln Pro Ile Ile Ser Lys Leu Tyr Gly Ser
                20                  25
```

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      GRP78 peptide sequence

<400> SEQUENCE: 32

```
Leu Glu Glu Ile Val Gln Pro Ile Ile Ser Lys Leu Tyr Gly Ser
1               5                   10                  15
```

<210> SEQ ID NO 33
<211> LENGTH: 4
<212> TYPE: PRT
<213> ORGANISM: Homo sapiens

<400> SEQUENCE: 33

```
Lys Asp Glu Leu
1
```

```
<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 34

His His His His His His
1               5

<210> SEQ ID NO 35
<211> LENGTH: 24
<212> TYPE: PRT
<213> ORGANISM: Homo sapiens

<400> SEQUENCE: 35

Lys Lys Glu Leu Glu Glu Ile Val Gln Pro Ile Ile Ser Lys Leu Tyr
1               5                   10                  15

Gly Ser Ala Gly Pro Pro Pro Thr
            20

<210> SEQ ID NO 36
<211> LENGTH: 357
<212> TYPE: DNA
<213> ORGANISM: Artificial Sequence
<220> FEATURE:
<223> OTHER INFORMATION: Description of Artificial Sequence: Synthetic
      Nucleic acid encoding a humanized GRP78 antibody heavy chain
      variable region

<400> SEQUENCE: 36
caggcccagc tggtgcagtc tggcgccgag gtgaagaaac ctggcgcctc cgtgaaggtg      60
tcctgcaagg cctccggcta caccttcacc agctactgga tgcactgggt gcggcaggcc     120
ccaggccagg gactggaatg gatcggcgag atcaacccg gcaacggccg gaccaactac      180
aacgagaagt tcaagcggag agtgaccatc accgtggaca gtccgcctc caccgcctac     240 atggaactgt cctccctgcg gagcgaggac accgccgtgt actactgcgc caccctgtac     300
tactacgacg gcacctacga ctactggggc cagggcacca ccgtgaccgt gtctagc        357
```

ANTIBODIES THAT BIND CELL SURFACE GRP78

RELATED PATENT APPLICATIONS

This application is a divisional under 35 U.S.C. § 120 of U.S. application Ser. No. 15/590,379, filed on May 9, 2017, which is a continuation under 35 U.S.C. § 120 of U.S. application Ser. No. 14/776,659, filed Sep. 14, 2015, which is a national stage entry under 35 U.S.C. § 371 of International Application No. PCT/US2014/028868, filed Mar. 14, 2014, which claims benefit under 35 U.S.C. § 119(e) of U.S. Provisional Application No. 61/781,395, filed on Mar. 14, 2013, the content of each of which is incorporated in its entirety by reference herein.

SEQUENCE LISTING

The instant application contains a Sequence Listing which has been submitted electronically in ASCII format and is hereby incorporated by reference in its entirety. Said ASCII copy, created on Jan. 16, 2020, is named 064189-7283_SL.txt and is 32,516 bytes in size.

TECHNICAL FIELD

This application relates to antibodies or antigen-binding fragments thereof which specifically bind to cell surface GRP78 expressed on tumor cells, tumor endothelial cells, and tumor initiating cancer cells; and methods of use thereof.

BACKGROUND ART

Cancer cells are characterized by metabolic alterations and the tumor microenvironment is often marked with impaired blood flow and hypoxia, all of which can elicit endoplasmic reticulum (ER) stress. Tumor cells adapt to these adverse conditions by activating the unfolded protein response (UPR), a cascade of intracellular stress signaling events in response to an accumulation of unfolded or misfolded proteins in the lumen of the ER. The UPR pathways are activated in a great variety of tumor types, and have been demonstrated to be essential for tumor cells to survive the unfriendly tumor microenvironment (Li et al., *J Heamtol. Oncol*, 4:8, 2011). Depending upon the duration and degree of ER stress, the UPR can provide either survival signals by activating adaptive and anti-apoptotic pathways, or death signals by inducing cell death programs. Because most normal cells are not undergoing active "stress" response, the UPR pathways remain in a quiescent state in these cells. This discrepancy between tumor cells and normal cells offers an advantage for the agents that target the UPR to achieve the specificity in cancer therapy, and UPR-targeted cancer therapeutics capable of inducing or repressing UPR pharmacologically have been evaluated (Id).

Induction of the ER chaperone GRP78 is a major pro-survival arm of the UPR signaling pathways (Ma and Hendrshot, *Cancer*, 12:966-977, 2004). GRP78, also referred to as BiP/HSPA5, is a 78 kilodalton glucose regulated protein with potent anti-apoptotic properties that plays critical roles in cancer cell survival, tumor progression, metastasis and resistance to therapy (Lee, *Cancer Res.*, 8:3496-99, 2007; Li and Li, *Biochim. Biophys. Acta*, 1:13-22, 2012)(each incorporated by reference in its entirety for all purposes). In human studies, GRP78 upregulation widely associates with tumor virulence and therapeutic resistance (Pfaffenbach and Lee, *Curr. Opin. Cell Biol.*, 2:150-156, 2011)(incorporated by reference in its entirety for all purposes). The creation of genetically altered Grp78 mouse models further demonstrated the critical role of GRP78 in cancer in vivo. For instance, in solid tumor models, Grp78 haploinsufficiency exhibited delayed tumor latency, decreased tumor proliferation, increased apoptosis, decreased tumor neoangiogenesis and metastatic growth (Dong et al., *Cancer Res.*, 2:498-505, 2008)(incorporated by reference in its entirety for all purposes). GRP78 has been established as a novel regulator of the PI3K/AKT oncogenic signaling and a target for anti-cancer therapy (Fu et al, *Proc. Natl. Acad. Sci. U.S.A.*, 49:19444-194449, 2008)(incorporated by reference in its entirety for all purposes).

While traditionally GRP78 has been regarded as an ER lumenal protein due to the KDEL retention motif (SEQ ID NO: 33) present on its carboxyl terminus, evidence has accumulated that a sub-fraction of GRP78 can exist in the outer plasma membrane of specific cell types (Arap et al, *Cell*, 3:275-284, 2004; Gonzalez-Gronow et al, *Antioxid. Redox Signal*, 9:2299-2306, 2009; Ni et al., *Biochem. J.*, 2:181-188, 2011)(each incorporated by reference in its entirety for all purposes). Biochemical studies further reveal that ER stress actively promotes cell surface localization of GRP78 and the translocation of GRP78 from the ER to the cell surface is regulated by the KDEL (SEQ ID NO: 33) retrieval machinery (Zhang et al, *J. Biol. Chem.*, 20:15065-15075, 2010)(incorporated by reference in its entirety for all purposes). This, coupled with the observation that peptides targeting GRP78 homed into tumor tissues but much less in normal organs suggests that cell surface GRP78 presents an opportunity for therapeutic targeting (Liu et al, *Mol. Pharm.*, 3:435-447, 2007; Sato et al, *Adv. Genet.*, 97-114, 2010)(each incorporated by reference in its entirety for all purposes).

DISCLOSURE OF THE INVENTION

This application provides, inter alia, novel antibodies, or antigen-binding fragments thereof, targeting cell surface GRP78 expressed on tumor cells, tumor endothelial cells, and tumor initiating cancer cells. These anti-GRP78 antibodies, or antigen-binding fragments thereof, have a high affinity for cell surface GRP78 and are less immunogenic compared to their unmodified parent antibodies in a given species, e.g., a human, and function to inhibit GRP78. Importantly, these isolated novel antibodies and antigen-binding fragments thereof, attenuate PI3K signaling, and promote apoptosis in tumor cells, while leaving normal cells unaffected. The antibodies and antigen-binding fragments are useful for UPR-targeted cancer therapeutic treatments.

In one aspect, isolated antibodies or antigen-binding fragments thereof which bind to human cell surface GRP78 as depicted in SEQ ID NO: 1 are provided. In certain embodiments, an isolated antibody or antigen-binding fragment of the invention binds to an epitope depicted in SEQ ID NO: 31. In certain embodiments, an isolated antibody or antigen-binding fragment of the invention binds to an epitope depicted in SEQ ID NO: 32.

In certain embodiments, an isolated antibody or antigen-binding fragment thereof of the invention binds to human cell surface GRP78 and comprises CDR regions VHCDR1, VHCDR2, VHCDR3, having the amino acid sequences set forth in SEQ ID NO: 3, SEQ ID NO: 4, and SEQ ID NO: 5, respectively. In certain embodiments, an isolated antibody or antigen-binding fragment thereof of the invention binds to human cell surface GRP78 and comprises CDR regions $V_HCDR_1$, $V_HCDR_2$, and $V_HCDR_3$ having the amino acid sequences set forth in SEQ ID NO: 6, SEQ ID NO: 7, and SEQ ID NO: 8, respectively. In certain embodiments, an isolated antibody or antigen-binding fragment thereof of the invention binds to human cell surface GRP78 and comprises CDR regions $V_HCDR_1$, $V_HCDR_2$, $V_HCDR_3$, having the amino acid sequences set forth in SEQ ID NO: 3, SEQ ID NO: 4, and SEQ ID NO: 5, respectively, and comprises CDR regions $V_HCDR_1$, $V_HCDR_2$, and $V_HCDR_3$ having the amino acid sequences set forth in SEQ ID NO: 6, SEQ ID NO: 7, and SEQ ID NO: 8, respectively.

In certain embodiments, an isolated humanized antibody or antigen-binding fragment thereof of the invention binds to human cell surface GRP78 and comprises a heavy chain variable region having the sequence set forth in SEQ ID NO: 13, SEQ ID NO: 15, SEQ ID NO: 17, SEQ ID NO: 19 or SEQ ID NO: 21, and a light chain variable region having the sequence set forth in SEQ ID NO: 23, SEQ ID NO: 25, SEQ ID NO: 27 or SEQ ID NO: 29.

In one embodiment, an isolated antibody or antigen-binding fragment thereof of the invention binds to human cell surface GRP78 and comprises the heavy chain variable region sequence set forth in SEQ ID NO: 21, and the light chain variable region sequence set forth in SEQ ID NO: 23.

In one embodiment, an isolated antibody or antigen-binding fragment thereof of the invention binds to human cell surface GRP78 and comprises the heavy chain variable region sequence set forth in SEQ ID NO: 15, and the light chain variable region sequence forth in SEQ ID NO: 27.

In one embodiment, an isolated antibody or antigen-binding fragment thereof of the invention binds to human cell surface GRP78 and comprises the heavy chain variable region sequence set forth in SEQ ID NO: 13, and the light chain variable region sequence set forth in SEQ ID NO: 23.

In one embodiment, an isolated antibody or antigen-binding fragment thereof of the invention binds to human cell surface GRP78 and comprises the heavy chain variable region sequence set forth in SEQ ID NO: 17, and the light chain variable region sequence set forth in SEQ ID NO: 25.

In one embodiment, an isolated antibody or antigen-binding fragment thereof of the invention binds to human cell surface GRP78 and comprises the heavy chain variable region sequence set forth in SEQ ID NO: 19, and the light chain variable region sequence set forth in SEQ ID NO: 25.

In one embodiment, an isolated antibody or antigen-binding fragment thereof of the invention binds to human cell surface GRP78 and comprises the heavy chain variable region sequence set forth in SEQ ID NO: 19, and the light chain variable region sequence set forth in SEQ ID NO: 29.

In certain embodiments, the heavy chain variable region includes a) an FR1 selected from the group consisting of amino acids 1-30 of SEQ ID NO: 13, SEQ ID NO: 15, SEQ ID NO: 17, SEQ ID NO: 19, and SEQ ID NO: 21; b) an FR2 selected from the group consisting of amino acids 36-49 of SEQ ID NO: 13, SEQ ID NO: 15, SEQ ID NO: 17, SEQ ID NO: 19, and SEQ ID NO: 21; c) an FR3 selected from the group consisting of amino acids 67-98 of SEQ ID NO: 13, SEQ ID NO: 15, SEQ ID NO: 17, SEQ ID NO: 19, and SEQ ID NO: 21; and d) an FR4 selected from the group consisting of amino acids 109-119 of SEQ ID NO: 13, SEQ ID NO: 15, SEQ ID NO: 17, SEQ ID NO: 19, and SEQ ID NO: 21.

In certain embodiments, the light chain variable region includes a) an FR1 selected from the group consisting of amino acids 1-23 of SEQ ID NO: 23, SEQ ID NO: 25, SEQ ID NO: 27, and SEQ ID NO: 29; b) an FR2 selected from the group consisting of amino acids 35-49 of SEQ ID NO: 23, SEQ ID NO: 25, SEQ ID NO: 27, and SEQ ID NO: 29; c) an FR3 selected from the group consisting of amino acids 55-86 of SEQ ID NO: 23, SEQ ID NO: 25, SEQ ID NO: 27, and SEQ ID NO: 29; and d) an FR4 selected from the group consisting of amino acids 96-105 of SEQ ID NO: 23, SEQ ID NO: 25, SEQ ID NO: 27, and SEQ ID NO: 29.

In another aspect, isolated antibodies or antigen-binding fragments thereof which bind to human cell surface GRP78 and are less immunogenic in a human subject than the monoclonal antibody which comprises the heavy chain variable region sequence set forth in SEQ ID NO: 9 and the light chain variable region sequence set forth in SEQ ID NO: 11 are provided.

In another aspect, isolated antibodies or antigen-binding fragments thereof which bind to human cell surface GRP78 with a similar or greater binding affinity than the monoclonal antibody which comprises the heavy chain variable region sequence set forth in SEQ ID NO: 9 and the light chain variable region sequence set forth in SEQ ID NO: 11 are provided.

In another aspect, isolated antibodies or antigen-binding fragments thereof which compete for binding to the epitope depicted in SEQ ID NO: 31 with the monoclonal antibody which comprises the heavy chain variable region sequence set forth in SEQ ID NO: 9 and the light chain valiable region sequence set forth in SEQ ID NO: 11 are provided.

In another aspect, isolated antibodies or antigen-binding fragments thereof which compete for binding to the epitope depicted in SEQ ID NO: 32 with the monoclonal antibody which comprises the heavy chain variable region sequence set forth in SEQ ID NO: 9 and the light chain variable region sequence set forth in SEQ ID NO: 11 are provided.

In certain embodiments, the antibody or antigen-binding fragment thereof is a polyclonal antibody, a monoclonal antibody or antigen-binding fragment thereof, a recombinant antibody, a diabody, a chimerized or chimeric antibody or antigen-binding fragment thereof, a humanized antibody or antigen-binding fragment thereof, a fully human antibody or antigen-binding fragment thereof, a CDR-grafted antibody or antigen-binding fragment thereof, a single chain antibody, an Fv, an Fd, an Fab, an Fab', or an F(ab')$_2$, and synthetic or semi-synthetic antibodies.

In certain embodiments, the antibody or antigen-binding fragment binds to cell surface GRP78 protein with a dissociation constant ($K_D$) of at least about $1\times10^{-3}$ M, at least about $1\times10^{-4}$ M, at least about $1\times10^{-5}$ M, at least about $1\times10^{-6}$ M, at least about $1\times10^{-7}$ M, at least about $1\times10^{-8}$ M, at least about $1\times10^{-9}$ M, at least about $1\times10^{-10}$ M, at least about $1\times10^{-11}$ M, or at least about $1\times10^{-12}$ M.

In another aspect, the antibodies and antigen-binding fragments thereof are of use for detecting tumors that express GFP78, such as, e.g., tumors associated with prostate cancer, uterine cancer, breast cancer, ovarian cancer, myeloid leukemia, lymphatic leukemia, small cell lung cancer, colon cancer, pancreatic cancer, glioma, and head-neck cancer.

In another aspect, a method of inhibiting signaling through the PI3K/AKT pathway in a cell is provided. In certain embodiments, said method may comprise contacting the cell with an effective amount of antibody or antigen-binding fragment which binds to cell surface GRP78 protein and inhibits an activity of the GRP78.

In another aspect, a method of reducing the growth rate of a tumor in a subject is provided. In certain embodiments, the method includes administering to the subject a therapeutically effective amount of an antibody or antigen-binding fragment which binds to human cell surface GRP78. In one embodiment, the subject is a human subject. In certain embodiments, the tumor includes cells expressing a higher level of GRP78 than noncancerous cells of a comparable tissue.

In another aspect, the disclosure provides methods for treating a subject suffering from a cancer, including: (a) identifying in the subject a tumor having a plurality of cancer cells that express cell surface GRP78; and (b) administering to the subject an antibody or antigen-binding fragment which binds to cell surface GRP78. In certain embodiments, the cancer will be a cancer with high PI3K activity, e.g., prostate cancer, uterine cancer, breast cancer, ovarian cancer, myeloid leukemia, lymphatic leukemia, small cell lung cancer, colon cancer, pancreatic cancer, glioma, and head-neck cancer.

In another aspect, pharmaceutical compositions comprising an antibody or antigen-binding fragment thereof disclosed herein are provided. In certain embodiments, the composition may also include any pharmaceutically acceptable carriers or excipients.

In another aspect, the use of the antibodies or antigen-binding fragments thereof disclosed herein in the manufacture of a medicament for treating cancer is provided.

In another aspect, the antibodies or antigen-binding fragments disclosed herein may be covalently linked to (or otherwise stably associated with) an additional functional moiety, such as a label or a moiety that confers desirable pharmacokinetic properties. Exemplary labels include those that are suitable for detection by a method selected from the group consisting of: fluorescence detection methods, positron emission tomography detection methods and nuclear magnetic resonance detection methods. Labels may, for example, be selected from the group consisting of: a fluorescent label, a radioactive label, and a label having a distinctive nuclear magnetic resonance signature.

In another aspect, an isolated immunoconjugate comprising an antibody or antigen-binding fragment linked to (or otherwise stably associated with) an effector molecule is provided. In certain embodiments, the effector molecule is an immunotoxin, cytokine, chemokine, therapeutic agent, or chemotherapeutic agent. In various embodiments, the therapeutic agent is an auristatin or an auristatin derivative. In various embodiments, the auristatin derivative is dovaline-valine-dolaisoleunine-dolaproine-phenylalanine (MMAF) or monomethyauristatin E (MMAE).

In another aspect, polynucleotides including a nucleotide sequence encoding the antibodies or antigen-binding fragments thereof disclosed herein are provided. In celiain embodiments, polynucleotides that hybridize under stringent conditions to polynucleotides encoding the antibody or antigen-binding fragment thereof disclosed herein are provided. In another aspect, vectors including one or more nucleotide sequences encoding the antibodies or antigen-binding fragments thereof disclosed herein are provided. In another aspect, isolated cells including a vector that expresses the antibodies or antigen-binding fragments thereof disclosed herein are provided.

BRIEF DESCRIPTION OF THE DRAWINGS

FIG. 4A shows that MAb159 treatment (10 mg/kg, twice a week) significantly inhibited (58%) tumor progression in SCLC cell H249 xenograft model. FIG. 4B shows that MAb159 treatment (10 mg/kg, twice a week) significantly inhibited (78%) tumor progression in lung carcinoma cell A549 xenograft model. FIG. 4C shows that MAb159 treatment (10 mg/kg, twice a week) significantly inhibited (50%) tumor progression in colon cancer cell HT29 xenograft model. Normal mouse IgG (10 mg/kg antibodies, twice a week) was used as a control. Only the end point data of each study are shown. FIG. 4D shows that treatment using MAb159 (10 mg/kg, twice a week) improved the efficacy of Irinotecan (18 mg/kg, twice a week) in colon cancer cell colo205 xenograft model. When administrated alone, MAb159 inhibited tumor growth by 54% compared to control group. Irinotecan mono-therapy inhibited tumor growth by 85%. The combination therapy was more effective: it inhibited tumor growth by 95% and caused tumor regression to 47% of the starting tumor volume. Only the end point data of this study are shown. All data in FIGS. 4A-4D was presented as mean±standard error of mean (s.e.m). P value was calculated with student T-test, 2 tail, (*, P<0.05); (**, P<0.02).

FIG. 5A shows the efficacy of MAb159 in PTEN deficient, hormone refractory mouse prostate cancer cell CE1, FIG. 5B shows the efficacy of MAb159 in SCLC cell H249, FIG. 5C shows the efficacy of MAb159 in lung carcinoma cell A549, and FIG. 5D shows the efficacy of MAb159 in colon cancer cell HT29 xenograft models. The tumors were treated with 10 mg/kg antibodies, twice a week. FIG. 5E shows that MAb159 (10 mg/kg, twice a week) improved the efficacy of Irinotecan (18 mg/kg, twice a week) in colon cancer cell colo205 xenograft model. Only the end point data of this study are shown.

FIG. 6A shows pictures showing the hunched posture of $Pten^{f/f}$; Mx1-Cre mice treated with IgG compared to normal posture of those treated with Mab159 (10 mg/kg of normal mouse IgG or MAb159 co-administered with pIpC for 7 doses). FIG. 6B are graphs depicting quantitation of the spleen weight and leukemic blast cell percentages of WT (n=4), $cP^{f/f}$ treated with IgG (n=5), and $cP^{f/f}$ treated with MAb159 (n=8). All data are presented as mean±standard error (s.e.m). FIG. 6C are graphs depicting complete blood count with tail peripheral blood from WT (n=4), $cP^{f/f}$ treated with IgG (n=5), and $cP^{f/f}$ treated with MAb159 (n=8). Peripheral blood was collected via tail bleeding and analyzed using an auto hematology analyzer BC-2800 vet (Mindray) according to manufacturer's instructions. All data are presented as mean±standard error. FIG. 6D shows a representative Western blot result using bone marrow cell lysates for detection of the indicated protein levels. For each group, samples from two mice were used for analysis.

FIG. 14A depicts the first and last amino acids of GFP78 variants that were transiently expressed in 293T cells and the denatured and reduced total whole cell lysates were used for Western blotting with anti-Flag antibody and MAb159. FIG. 14B, left and right panel, are immunoblots showing the results of the Western blotting. Endogenously expressed GRP78 is indicated with black arrows. Based on the results depicted in FIG. 14C depicts the putative MAb159 epitope (SEQ ID NO: 35). The underlined residues are the last residue for K633 and T643 variants respectively. A638 is in bold black.

MODE(S) FOR CARRYING OUT THE INVENTION

Figure 1A:
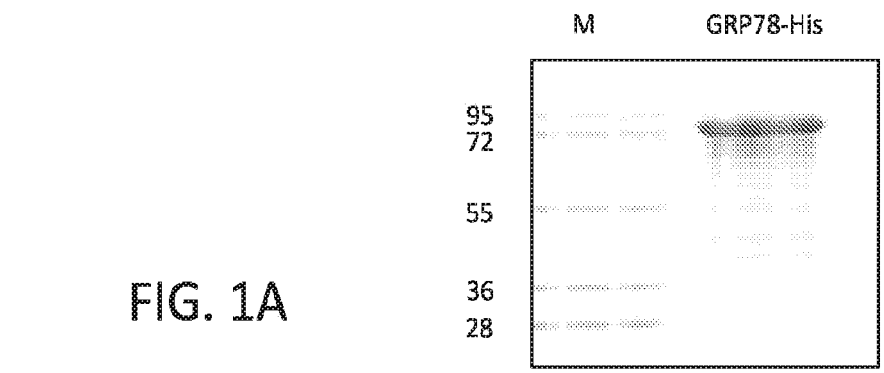
FIG. 1A depicts Coomassie staining of GRP78-His polypeptide on SDS-PAGE. M is the protein ladder.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those commonly used and well known in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2nd ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual, Cold Spring Harbor Laboratory Press, Cold Spring Harbor, N.Y. (1990), incorporated herein by reference. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those commonly used and well known in the art. Standard techniques are used for chemical syntheses, chemical analyses, pharmaceutical preparation, formulation, and delivery, and treatment of patients.

Definitions

The terms "polypeptide", "peptide" and "protein" are used interchangeably herein to refer to a polymer of amino acid residues. In certain embodiments, "peptides", "polypeptides", and "proteins" are chains of amino acids whose alpha carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free a-amino group on an amino acid at the amino terminal of a peptide or to the a-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to, peptide mimetics such as amino acids joined by an ether as opposed to an amide bond.

The term "polypeptide derivative" as used herein refers to a polypeptide that has been chemically modified, e.g., conjugation to another chemical moiety such as, for example, polyethylene glycol, albumin (e.g., human serum albumin), phosphorylation, and glycosylation. Polypeptides of the invention include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (5) confer or modify other physicochemical or functional properties. For example, single or multiple amino acid substitutions (e.g., conservative amino acid substitutions) may be made in the naturally occurring sequence (e.g., in the portion of the polypeptide outside the domain(s) forming intermolecular contacts). A "conservative amino acid substitution" refers to the substitution in a polypeptide of an amino acid with a functionally similar amino acid. The following six groups each contain amino acids that are conservative substitutions for one another:

Alanine (A), Serine (S), and Threonine (T)
Aspartic acid (D) and Glutamic acid (E)
Asparagine (N) and Glutamine (Q)
Arginine (R) and Lysine (K)
Isoleucine (I), Leucine (L), Methionine (M), and Valine (V)
Phenylalanine (F), Tyrosine (Y), and Tryptophan (W)

Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. (1991) Nature 354:105).

The term "polypeptide fragment" as used herein refers to a polypeptide that has an amino-terminal and/or carboxy-terminal deletion as compared to a corresponding full-length protein. In certain embodiments, fragments can be, e.g., at least 5, at least 10, at least 25, at least 50, at least 100, at least 150, at least 200, at least 250, at least 300, at least 350, at least 400, at least 450, at least 500, at least 600, at least 700, at least 800, at least 900 or at least 1000 amino acids in length. In certain embodiments, fragments can also be, e.g., at most 1000, at most 900, at most 800, at most 700, at most 600, at most 500, at most 450, at most 400, at most 350, at most 300, at most 250, at most 200, at most 150, at most 100, at most 50, at most 25, at most 10, or at most 5 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence).

The term "polypeptide analog" as used herein refers to a polypeptide that comprises a segment that has substantial identity to a portion of an amino acid sequence and that retains the ability to, e.g., regulate the PI3K/AKT oncogenic signaling. Typically, polypeptide analogs comprise a conservative amino acid substitution (or insertion or deletion) with respect to the native sequence. Analogs typically are at least 20 or 25 amino acids long, preferably at least 50, 60, 70, 80, 90, 100, 150 or 200 amino acids long or longer, and can often be as long as a full-length polypeptide.

The terms "polypeptide variant" and "polypeptide mutant" as used herein refers to a polypeptide that comprises an amino acid sequence wherein one or more amino acid residues are inserted into, deleted from and/or substituted into the amino acid sequence relative to another polypeptide sequence. In certain embodiments, the number of amino acid residues to be inserted, deleted, or substituted can be, e.g., at least 1, at least 2, at least 3, at least 4, at least 5, at least 10, at least 25, at least 50, at least 75, at least 100, at least 125, at least 150, at least 175, at least 200, at least 225, at least 250, at least 275, at least 300, at least 350, at least 400, at least 450 or at least 500 amino acids in length. Variants of the present invention include immunoconjugates and fusion proteins.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm, and means that a given sequence is at least 80% identical to another length of another sequence. In certain embodiments, the % identity is selected from, e.g., at least 60%, at least 65%, at least 70%, at least 75%, at least 80%, at least 85%, at least 90%, at least 95%, or at least 99% or more sequence identity to a given sequence. In certain embodiments, the % identity is in the range of, e.g., about 60% to about 70%, about 70% to about 80%, about 80% to about 85%, about 85% to about 90%, about 90% to about 95%, or about 95% to about 99%.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. In certain embodiments, the % homology is selected from, e.g., at least 60%, at least 65%, at least 70%, at least 75%, at least 80%, at least 85%, at least 90%, at least 95%, or at least 99% or more sequence homology to a given sequence. In certain embodiments, the % homology is in the range of, e.g., about 60% to about 70%, about 70% to about 80%, about 80% to about 85%, about 85% to about 90%, about 90% to about 95%, or about 95% to about 99%.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., 1990, J. Mol. Biol. 215:403-10 (with special reference to the published default setting, i.e., parameters w=4, t=17) and Altschul et al., 1997, Nucleic Acids Res., 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix.

In addition to calculating percent sequence identity, the BLAST algorithm also performs a statistical analysis of the similarity between two sequences (see, e.g., Karlin & Altschul, Proc. Nat'l. Acad. Sci. USA, 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is, e.g., less than about 0.1, less than about 0.01, or less than about 0.001.

The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

A protein or polypeptide is "substantially pure," "substantially homogeneous," or "substantially purified" when at least about 60 to 75% of a sample exhibits a single species of polypeptide. The polypeptide or protein may be monomeric or multimeric. A substantially pure polypeptide or protein will typically comprise about 50%, 60%, 70%, 80% or 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

As used herein, an "antibody" refers to a protein comprising one or more polypeptides substantially or partially encoded by immunoglobulin genes or fragments of immunoglobulin genes and having specificity to a tumor antigen or specificity to a molecule overexpressed in a pathological state. The recognized immunoglobulin genes include the kappa, lambda, alpha, gamma, delta, epsilon and mu constant region genes, as well as subtypes of these genes and myriad of immunoglobulin variable region genes. Light chains (LC) are classified as either kappa or lambda. Heavy chains (HC) are classified as gamma, mu, alpha, delta, or epsilon, which in turn define the immunoglobulin classes, IgG, IgM, IgA, IgD and IgE, respectively. A typical immunoglobulin (e.g., antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively.

In a full-length antibody, each heavy chain is comprised of a heavy chain variable region (abbreviated herein as HCVR or $V_H$) and a heavy chain constant region. The heavy chain constant region is comprised of three domains, $C_{H1}$, $CH_{H2}$ and $C_{H3}$ (and in some instances, $CH_4$). Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: $FR_1$, $CDR_1$, $FR_2$, $CDR_2$, $FR_3$, $CDR_3$, $FR_4$. The extent of the framework region and CDRs has been defined. The sequences of the framework regions of different light or heavy chains are relatively conserved within a species, such as humans. The framework region of an antibody, that is the combined framework regions of the constituent light and heavy chains, serves to position and align the CDRs in three-dimensional space. Immunoglobulin molecules can be of any type (e.g., IgG, IgE, IgM, IgD, IgA and IgY), class (e.g., IgG1, IgG2, IgG 3, IgG4, IgA1 and IgA2) or subclass.

The Kabat definition is a standard for numbering the residues in an antibody and is typically used to identify CDR regions. The Kabat database is now maintained online and CDR sequences can be determined, for example, see IMGTN-QUEST programme version: 3.2.18., Mar. 29, 2011, available on the internet and Brochet, X. et al., Nucl. Acids Res. 36, W503-508, 2008). The Chothia definition is similar to the Kabat definition, but the Chothia definition takes into account positions of certain structural loop regions. See, e.g., Chothia et al., J. Mol. Biol., 196: 901-17 (1986); Chothia et al., Nature, 342: 877-83 (1989). The AbM definition uses an integrated suite of computer programs produced by Oxford Molecular Group that model antibody structure. See, e.g., Martin et al., Proc Natl Acad Sci (USA), 86:9268-9272 (1989); "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl., 3:194-198 (1999). The contact definition is based on an analysis of the available complex crystal structures. See, e.g., MacCallum et al., J. Mol. Biol., 5:732-45 (1996).

The CDRs are primarily responsible for binding to an epitope of an antigen. The CDRs of each chain are typically referred to as $CDR_1$, $CDR_2$, $CDR_3$, numbered sequentially starting from the N-terminus, and are also typically identified by the chain in which the particular CDR is located. Thus, a $V_H CDR_3$ is located in the variable domain of the heavy chain of the antibody in which it is found, whereas a $V_L CDR_1$ is the $CDR_1$ from the variable domain of the light chain of the antibody in which it is found. Antibodies with different specificities (i.e. different combining sites for different antigens) have different CDRs. Although it is the CDRs that vary from antibody to antibody, only a limited number of amino acid positions within the CDRs are directly involved in antigen-binding. These positions within the CDRs are called specificity determining residues (SDRs).

The term "Fc region" is used to define the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a $C_{H2}$ domain and a $C_{H3}$ domain, and optionally comprises a $C_{H4}$ domain. The Fc portion of an antibody mediates several important effector functions e.g. cytokine induction, ADCC, phagocytosis, complement dependent cytotoxicity (CDC) and half-life/clearance rate of antibody and antigen-antibody complexes (e.g., the neonatal FcR (FcRn) binds to the Fe region of IgG at acidic pH in the endosome and protects IgG from degradation, thereby contributing to the long serum half-life of IgG). Replacements of amino acid residues in the Fc portion to alter antibody effector function are known in the art (see, e.g., Winter et al., U.S. Pat. Nos. 5,648,260 and 5,624,821).

Antibodies exist as intact immunoglobulins or as a number of well characterized fragments. Such fragments include Fab fragments, Fab' fragments, $Fab_2$, $F(ab)'_2$ fragments, single chain Fv proteins ("scFv") and disulfide stabilized Fv proteins ("dsFv"), that bind to the target antigen. A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. While various antibody fragments are defined in terms of the digestion of an intact antibody, one of skill will appreciate that such fragments may be synthesized de novo either chemically or by utilizing recombinant DNA methodology. Thus, as used herein, the term antibody encompasses e.g., monoclonal antibodies (including full-length monoclonal antibodies), polyclonal antibodies, multispecific antibodies (e.g., bispecific antibodies) formed from at least two intact antibodies, human antibodies, humanized antibodies, camelised antibodies, chimeric antibodies, single-chain Fvs (scFv), single-chain antibodies, single domain antibodies, domain antibodies, Fab fragments, $F(ab')_2$ fragments, antibody fragments that exhibit the desired biological activity, disulfide-linked Fvs (dsFv), intrabodies, and epitope-binding fragments or antigen-binding fragments of any of the above.

Papain digestion of antibodies produces two identical antigen-binding fragments, called "Fab" fragments, each with a single antigen-binding site. A "Fab fragment" comprises one light chain and the $C_{H1}$ and variable regions of one heavy chain. The heavy chain of a Fab molecule cannot form a disulfide bond with another heavy chain molecule.

A "Fab' fragment" comprises one light chain and a portion of one heavy chain that contains the $V_H$ domain and the $C_{H1}$ domain and also the region between the $C_{H1}$ and $C_{H2}$ domains, such that an interchain disulfide bond can be formed between the two heavy chains of two Fab' fragments to form an $F(ab')_2$ molecule.

Pepsin treatment of an antibody yields an $F(ab')_2$ fragment that has two antigen-combining sites and is still capable of cross-linking antigen. A "$F(ab')_2$ fragment" contains two light chains and two heavy chains containing a portion of the constant region between the $C_{H1}$ and $C_{H2}$ domains, such that an interchain disulfide bond is formed between the two heavy chains. A $F(ab')_2$ fragment thus is composed of two Fab' fragments that are held together by a disulfide bond between the two heavy chains.

The "Fv region" comprises the variable regions from both the heavy and light chains, but lacks the constant regions.

"Single-chain antibodies" are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649, U.S. Pat. Nos. 4,946,778 and 5,260,203, the disclosures of which are incorporated by reference.

The terms "an antigen-binding fragment" and "antigen-binding protein" as used herein means any protein that binds a specified target antigen. In the instant application, the specified target antigen is human cell surface GRP78 protein or fragment thereof "Antigen-binding fragment" includes but is not limited to antibodies and binding parts thereof, such as immunologically functional fragments. An exemplary antigen-binding fragment of an antibody is the heavy chain and/or light chain CDR(s), or the heavy and/or light chain variable region.

The term "immunologically functional fragment" (or simply "fragment") of an antibody or immunoglobulin chain (heavy or light chain) antigen-binding protein, as used herein, is a species of antigen-binding protein comprising a portion (regardless of how that portion is obtained or synthesized) of an antibody that lacks at least some of the amino acids present in a full-length chain but which is still capable of specifically binding to an antigen. Such fragments are biologically active in that they bind to the target antigen and can compete with other antigen-binding proteins, including intact antibodies, for binding to a given epitope. In some embodiments, the fragments are neutralizing fragments. In some embodiments, the fragments can block or reduce the likelihood of the interaction between GRP78 and PI3K. In one aspect, such a fragment will retain at least one CDR present in the full-length light or heavy chain, and in some embodiments will comprise a single heavy chain and/or light chain or portion thereof. These biologically active fragments can be produced by recombinant DNA techniques, or can be produced by enzymatic or chemical cleavage of antigen-binding proteins, including intact antibodies. Immunologically functional immunoglobulin fragments include, but are not limited to, Fab, a diabody, Fab', $F(ab')_2$, Fv, domain antibodies and single-chain antibodies, and can be derived from any mammalian source, including but not limited to human, mouse, rat, camelid or rabbit. It is further contemplated that a functional pollion of the antigen-binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life.

Diabodies are bivalent antibodies comprising two polypeptide chains, wherein each polypeptide chain comprises $V_H$ and $V_L$ regions joined by a linker that is too short to allow for pairing between two regions on the same chain, thus allowing each region to pair with a complementary region on another polypeptide chain (see, e.g., Holliger et al., 1993, Proc. Natl. Acad. Sci. USA 90:6444-48 (1993), and Poljak et al., Structure 2:1121-23 (1994)). If the two polypeptide chains of a diabody are identical, then a diabody resulting from their pairing will have two identical antigen-binding sites. Polypeptide chains having different sequences can be used to make a diabody with two different antigen-binding sites. Similarly, tribodies and tetrabodies are antibodies comprising three and four polypeptide chains, respectively, and forming three and four antigen-binding sites, respectively, which can be the same or different.

In certain embodiments, antibodies and antibody fragments used in the constructs of the present invention can be bispecific. Bispecific antibodies or fragments can be of several configurations. For example, bispecific antibodies may resemble single antibodies (or antibody fragments) but have two different antigen-binding sites (variable regions). In various embodiments bispecific antibodies can be produced by chemical techniques (Kranz et al., Proc. Natl. Acad. Sci., USA, 78:5807, 1981), by "polydoma" techniques (see, e.g., U.S. Pat. No. 4,474,893), or by recombinant DNA techniques. In certain embodiments bispecific antibodies of the present invention can have binding specificities for at least two different epitopes at least one of which is a tumor associate antigen. In various embodiments the antibodies and fragments can also be heteroantibodies. Heteroantibodies are two or more antibodies, or antibody binding fragments (e.g., Fab) linked together, each antibody or fragment having a different specificity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method.

The term "chimeric antibody" as used herein refers to an antibody which has framework residues from one species, such as human, and CDRs (which generally confer antigen-binding) from another species, such as a murine antibody that specifically binds targeted antigen.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular $CDR_3$. However, the term "human antibody", as used herein, is not intended to include antibodies in which CDR sequences derived from the germline of another mammalian species, such as a mouse, have been grafted onto human framework sequences.

The term "humanized antibody" as used herein refers to an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen-binding or other immunoglobulin functions.

The term "recombinant human antibody", as used herein, is intended to include all human antibodies that are prepared, expressed, created or isolated by recombinant means, such as antibodies expressed using a recombinant expression vector transfected into a host cell; antibodies isolated from a recombinant, combinatorial human antibody library; antibodies isolated from an animal (e.g., a mouse) that is transgenic for human immunoglobulin genes; or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo. All such recombinant means are well known to those of ordinary skill in the art.

The term "epitope" as used herein includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. An epitope may be "linear" or "conformational." In a linear epitope, all of the points of interaction between the protein and the interacting molecule (such as an antibody) occur linearly along the primary amino acid sequence of the protein. In a conformational epitope, the points of interaction occur across amino acid residues on the protein that are separated from one another. Once a desired epitope on an antigen is determined, it is possible to generate antibodies to that epitope, e.g., using the techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct cross-competition studies to find antibodies that competitively bind with one another, e.g., the antibodies compete for binding to the antigen.

An antigen-binding protein, including an antibody, "specifically binds" to an antigen if it binds to the antigen with a high binding affinity as determined by a dissociation constant ($K_D$, or corresponding Kb, as defined below) value of at least $1 \times 10^{-6}$ M, or at least $1 \times 10^{-7}$ M, or at least $1 \times 10^{-8}$ M, or at least $1 \times 10^{-9}$ M, or at least $1 \times 10^{-10}$ M, or at least $1 \times 10^{-11}$ M. An antigen-binding protein that specifically binds to the human antigen of interest may be able to bind to the same antigen of interest from other species as well, with the same or different affinities. The term "$K_D$" as used herein refers to the equilibrium dissociation constant of a particular antibody-antigen interaction.

The term "surface plasmon resonance" as used herein refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.). For further descriptions, see Jonsson U. et al., Ann. Biol. Clin. 51:19-26 (1993); Jonsson U. et al., Biotechniques 11:620-627 (1991); Jonsson B. et al., J. Mol. Recognit. 8:125-131 (1995); and Johnsson B. et al., Anal. Biochem. 198:268-277 (1991).

The term "immunoconjugate" as used herein refers to a molecule comprising an antibody or antigen-binding fragment thereof conjugated directly or indirectly to an effector molecule. The effector molecule can be a detectable label, an immunotoxin, cytokine, chemokine, therapeutic agent, or chemotherapeutic agent. An immunoconjugate retains the immunoreactivity of the antibody or antigen-binding fragment, e.g., the antibody or antigen-binding fragment has approximately the same, or only slightly reduced, ability to bind the antigen after conjugation as before conjugation. As used herein, an immunoconjugate is also referred to as an antibody drug conjugate (ADC).

The term "polynucleotide" as used herein refers to a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

The term "complementary" as used herein refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is substantially identical to the nucleotide sequence of the polynucleotide binding partner of the second polynucleotide, or if the first polynucleotide can hybridize to the second polynucleotide under stringent hybridization conditions.

The terms "hybridizing specifically to" or "specific hybridization" or "selectively hybridize to", as used herein refer to the binding, duplexing, or hybridizing of a nucleic acid molecule preferentially to a particular nucleotide sequence under stringent conditions when that sequence is present in a complex mixture (e.g., total cellular) DNA or RNA. The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence-dependent, and are different under different environmental parameters. An extensive guide to the hybridization of nucleic acids can be found in Tijssen, 1993, Laboratory Techniques in Biochemistry and Molecular Biology—Hybridization with Nucleic Acid Probes, part I, chapter 2, "Overview of principles of hybridization and the strategy of nucleic acid probe assays", Elsevier, N.Y.; Sambrook et al., 2001, Molecular Cloning: A Laboratory Manual, Cold Spring Harbor Laboratory, 3.sup.rd ed., NY; and Ausubel et al., eds., Current Edition, Current Protocols in Molecular Biology, Greene Publishing Associates and Wiley Interscience, NY.

Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe. An example of stringent hybridization conditions for hybridization of complementary nucleic acids which have more than about 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes. See Sambrook et al. for a description of SSC buffer. A high stringency wash can be preceded by a low stringency wash to remove background probe signal. An exemplary medium stringency wash for a duplex of, e.g., more than about 100 nucleotides, is 1×SSC at 45° C. for 15 minutes. An exemplary low stringency wash for a duplex of, e.g., more than about 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

The term "primer" as used herein refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

The term "probe," when used herein in reference to a polynucleotide, refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties. In instances where a probe provides a point of initiation for synthesis of a complementary polynucleotide, a probe can also be a primer.

A "vector" is a polynucleotide that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial Oligin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-06.

The term "operably linked" used herein refers to sequences which include both expression control sequences that are contiguous with the gene of interest and expression control sequences that act in trans or at a distance to control the gene of interest. The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

A "host cell" is a cell that can be used to express a polynucleotide of the invention. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but to the progeny or potential progeny of such a cell. Because certain modifications may occur in succeeding generations due to, e.g., mutation or environmental influence, such progeny may not, in fact, be identical to the parent cell, but are still included within the scope of the term as used herein.

The terms "label" or "labeled" as used herein refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^3H$, $^{14}C$, $^{15}N$, $^{35}S$, $^{90}Y$, $^{99}Tc$, $^{111}In$, $^{125}I$, $^{131}I$) fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

The term "immunogenicity" as used herein refers to the ability of an antibody or antigen-binding fragment to elicit an immune response (humoral or cellular) when administered to a recipient and includes, for example, the HAMA response. A HAMA response is initiated when T-cells from a subject make an immune response to the administered antibody. The T-cells then recruit B-cells to generate specific "anti-antibody" antibodies.

The terms "treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment.

GRP78 Antigen

Human cell surface GRP78 as used herein comprises amino acids residues 1-650 of the amino acid sequence set forth in SEQ ID NO: 1:

```
                                              (SEQ ID NO: 1)
MKLSLVAAMLLLLSAARAEEEDKKEDVGTVVGIDLGTTYSCVGVFKNGRV

EIIANDQGNRITPSYVAFTPEGERLIGDAAKNQLTSNPENTVFDAKRLIG

RTWNDPSVQQDIKFLPFKVVEKKTKPYIQVDIGGGQTKTFAPEEISAMVL

TKMKETAEAYLGKKVTHAVVTVPAYFNDAQRQATKDAGTIAGLNVMRIIN

EPTAAAIAYGLDKREGEKNILVFDLGGGTFDVSLLTIDNGVFEVVATNGD

THLGGEDFDQRVMEHFIKLYKKKTGKDVRKDNRAVQKLRREVEKAKRALS

SQHQARIEIESFYEGEDFSETLTRAKFEELNMDLFRSTMKPVQKVLEDSD

LKKSDIDEIVLVGGSTRIPKIQQLVKEFFNGKEPSRGINPDEAVAYGAAV

QAGVLSGDQDTGDLVLLDVCPLTLGIETVGGVMTKLIPRNTVVPTKKSQI

FSTASDNQPTVTIKVYEGERPLTKDNHLLGTFDLTGIPPAPRGVPQIEVT

FEIDVNGILRVTAEDKGTGNKNKITITNDQNRLTPEEIERMVNDAEKFAE

EDKKLKERIDTRNELESYAYSLKNQIGDKEKLGGKLSSEDKETMEKAVEE

KIEWLESHQDADIEDFKAKKKELEEIVQPIISKLYGSAGPPPTGEEDTAE

KDEL
```

Amino acid residues 651-654 (underlined) represent a C-terminal peptide.

Human cell surface GRP78 as used herein is encoded by nucleic acids 1-1950 of the nucleic acid sequence set forth in SEQ ID NO: 2:

```
                                              (SEQ ID NO: 2)
atgaagctctccctggtggccgcgatgctgctgctgctcagcgcggcgcg ggccgaggaggaggacaagaaggaggacgtgggcacggtggtcggcatcg acctggggaccacctactcctgcgtcggcgtgttcaagaacggccgcgtg gagatcatcgccaacgatcagggcaaccgcatcacgccgtcctatgtcgc cttcactcctgaaggggaacgtctgattggcgatgccgccaagaaccagc
```

-continued

```
tcacctccaacccegagaacacggtctttgacgccaagcggctcatcggc cgcacgtggaatgaccegtctgtgcagcaggacatcaagttcttgccgtt caaggtggttgaaaagaaaactaaaccatacattcaagttgatattggag gtgggcaaacaaagacatttgctcctgaagaaatttctgccatggttctc actaaaatgaaagaaaccgctgaggcttatttgggaaagaaggttaccca tgcagttgttactgtaccagcctattttaatgatgcccaacgccaagcaa ccaaagacgctggaactattgctggcctaaatgttatgaggatcatcaac gagcctacggcagctgctattgcttatggcctggataagagggagggggaa gaagaacatcctggtgtttgacctgggtggcggaaccttcgatgtgtctc ttctcaccattgacaatggtgtcttcgaagttgtggccactaatggagat actcatctgggtggagaagactttgaccagcgtgtcatggaacacttcat caaactgtacaaaaagaagacgggcaaagatgtcaggaaagacaatagag ctgtgcagaaactccggcgcgaggtagaaaaggccaaacgggcctgtct tctcagcatcaagcaagaattgaaattgagtccttctatgaaggagaaga cttttctgagaccctgactcgggccaaatttgaagagctcaacatggatc tgttccggtctactatgaagcccgtccagaaagtgttggaagattctgat ttgaagaagtctgatattgatgaaattgttcttgttggtggctcgactcg aattccaaagattcagcaactggttaaagagttcttcaatggcaaggaac catccegtggcataaaccagatgaagctgtagcgtatggtgctgctgtc caggctggtgtgctctctggtgatcaagatacaggtgacctggtactgct tgatgtatgtccccttacacttggtattgaaactgtgggaggtgtcatga ccaaactgattccaaggaacacagtggtgcctaccaagaagtctcagatc ttttctacagcttctgataatcaaccaactgttacaatcaaggtctatga aggtgaaagacccctgacaaaagacaatcatcttctgggtacatttgatc tgactggaattcctcctgctcctcgtggggtcccacagattgaagtcacc tttgagatagatgtgaatggtattcttcgagtgacagctgaagacaaggg tacagggaacaaaaataagatcacaatcaccaatgaccagaatcgcctga cacctgaagaaatcgaaaggatggttaatgatgctgagaagtttgctgag gaagacaaaaagctcaaggagcgcattgatactagaaatgagttggaaag ctatgcctattctctaaagaatcagattggagataaagaaaagctgggag gtaaactttcctctgaagataaggagaccatggaaaaagctgtagaagaa aagattgaatggctggaaagccaccaagatgctgacattgaagacttcaa agctaagaagaaggaactggaagaaattgttcaaccaattatcagcaaac tctatggaagtgcaggccctcccccaactggtgaagaggatacagcagaa aaagatgagttgtag
```

In various embodiments, a cell surface GRP78 polypeptide comprises a sequence of amino acids that is at least 70%, 75%, 80%, 85%, 90%, 95%, 97%, or 99% identical to the amino acid sequence set forth in SEQ ID NO: 1. In various embodiments, a cell surface GRP78 polypeptide comprises a sequence of amino acids that is encoded by a nucleotide sequence that is at least 70%, 75%, 80%, 85%, 90%, 95%, 97%, or 99% identical to the amino acid sequence set forth in SEQ ID NO: 2.

Polypeptide variants of GRP78 may be described herein by reference to the addition, deletion, or substitution of amino acid residue present at a given position in the 650 amino acid sequence of SEQ ID NO: 1. Thus, for example, the term "V27W" indicates that the "V" (valine, in standard single letter code) residue at position 27 in SEQ ID NO: 1 has been substituted with a "W" (tryptophan, in standard single letter code).

Antibodies

Methods of generating novel antibodies that bind to human cell surface GRP78 polypeptide are known to those skilled in the art. For example, a method for generating a monoclonal antibody that binds specifically to an GRP78 polypeptide may comprise administering to a mouse an amount of an immunogenic composition comprising the GRP78 polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monoclonal antibody that binds specifically to the GRP78 polypeptide. Once obtained, a hybridoma can be propagated in a cell culture, optionally in culture conditions where the hybridoma-derived cells produce the monoclonal antibody that binds specifically to GRP78 polypeptide. The monoclonal antibody may be purified from the cell culture. A variety of different techniques are then available for testing antibody:antigen interactions to identify particularly desirable antibodies.

Other suitable methods of producing or isolating antibodies of the requisite specificity can used, including, for example, methods which select recombinant antibody from a library, or which rely upon immunization of transgenic animals (e.g., mice) capable of producing a full repertoire of human antibodies. See e.g., Jakobovits et al., Proc. Natl. Acad. Sci. USA, 90: 2551-2555 (1993); Jakobovits et al., Nature, 362: 255-258 (1993); Lonberg et al., U.S. Pat. No. 5,545,806; Surani et al., U.S. Pat. No. 5,545,807.

Antibodies can be engineered in numerous ways. They can be made as single-chain antibodies (including small modular immunopharmaceuticals or SMIPs™), Fab and F(ab')2 fragments, etc. Antibodies can be humanized, chimerized, deimmunized, or fully human. Numerous publications set forth the many types of antibodies and the methods of engineering such antibodies. For example, see U.S. Pat. Nos. 6,355,245; 6,180,370; 5,693,762; 6,407,213; 6,548,640; 5,565,332; 5,225,539; 6,103,889; and 5,260,203.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 Science 240:1041-1043); Liu et al. (1987) PNAS 84:3439-3443; Liu et al., 1987, J. Immunol. 139:3521-3526; Sun et al. (1987) PNAS 84:214-218; Nishimura et al., 1987, Canc. Res. 47:999-1005; Wood et al. (1985) Nature 314:446-449; and Shaw et al., 1988, J. Natl Cancer Inst. 80:1553-1559).

Methods for humanizing antibodies have been described in the art. In some embodiments, a humanized antibody has one or more amino acid residues introduced from a source that is nonhuman, in addition to the nonhuman CDRs. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable region has been substituted by the corresponding sequence from a nonhuman species. In practice, humanized antibodies are typically human antibodies in which some hypervariable region residues and possibly some framework region residues are substituted by residues from analogous sites in rodent antibodies.

U.S. Pat. No. 5,693,761 to Queen et al, discloses a refinement on Winter et al. for humanizing antibodies, and is based on the premise that ascribes avidity loss to problems in the structural motifs in the humanized framework which, because of steric or other chemical incompatibility, interfere with the folding of the CDRs into the binding-capable conformation found in the mouse antibody. To address this problem, Queen teaches using human framework sequences closely homologous in linear peptide sequence to framework sequences of the mouse antibody to be humanized. Accordingly, the methods of Queen focus on comparing framework sequences between species. Typically, all available human variable region sequences are compared to a particular mouse sequence and the percentage identity between correspondent framework residues is calculated. The human variable region with the highest percentage is selected to provide the framework sequences for the humanizing project. Queen also teaches that it is important to retain in the humanized framework, certain amino acid residues from the mouse framework critical for supporting the CDRs in a binding-capable conformation. Potential criticality is assessed from molecular models. Candidate residues for retention are typically those adjacent in linear sequence to a CDR or physically within 6 Å of any CDR residue.

In other approaches, the importance of particular framework amino acid residues is determined experimentally once a low-avidity humanized construct is obtained, by reversion of single residues to the mouse sequence and assaying antigen-binding as described by Riechmann et al, (1988). Another example approach for identifying important amino acids in framework sequences is disclosed by U.S. Pat. No. 5,821,337 to Carter et al, and by U.S. Pat. No. 5,859,205 to Adair et al. These references disclose specific Kabat residue positions in the framework, which, in a humanized antibody may require substitution with the correspondent mouse amino acid to preserve avidity.

Another method of humanizing antibodies, referred to as "framework shuffling", relies on generating a combinatorial library with nonhuman CDR variable regions fused in frame into a pool of individual human germline frameworks (Dall'Acqua et al., Methods, 36:43 (2005)). The libraries are then screened to identify clones that encode humanized antibodies which retain good binding.

The choice of human variable regions, both light and heavy, to be used in making the humanized antibodies is very important to reduce antigenicity. According to the so-called "best-fit" method, the sequence of the variable region of a rodent antibody is screened against the entire library of known human variable-domain sequences. The human sequence that is closest to that of the rodent is then accepted as the human framework region (framework region) for the humanized antibody (Sims et al., J. Immunol., 151:2296 (1993); Chothia et al., J. Mol. Biol., 196:901 (1987)). Another method uses a particular framework region derived from the consensus sequence of all human antibodies of a particular subgroup of light or heavy chain variable regions. The same framework may be used for several different humanized antibodies (Carter et al., Proc. Natl. Acad. Sci. USA, 89:4285 (1992); Presta et al., J. Immunol., 151:2623 (1993)).

The choice of nonhuman residues to substitute into the human variable region can be influenced by a variety of factors. These factors include, for example, the rarity of the amino acid in a particular position, the probability of interaction with either the CDRs or the antigen, and the probability of participating in the interface between the light and heavy chain variable domain interface. (See, for example, U.S. Pat. Nos. 5,693,761, 6,632,927, and 6,639,055). One method to analyze these factors is through the use of three-dimensional models of the nonhuman and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, e.g., the analysis of residues that influence the ability of the candidate immunoglobulin to bind its antigen. In this way, nonhuman residues can be selected and substituted for human variable region residues in order to achieve the desired antibody characteristic, such as increased affinity for the target antigen(s).

Methods for making fully human antibodies have been described in the art. By way of example, a method for producing an anti-GRP78 antibody or antigen-binding fragment thereof comprises the steps of synthesizing a library of human antibodies on phage, screening the library with GRP78 or an antibody-binding portion thereof, isolating phage that bind GRP78, and obtaining the antibody from the phage. By way of another example, one method for preparing the library of antibodies for use in phage display techniques comprises the steps of immunizing a non-human animal comprising human immunoglobulin loci with GRP78 or an antigenic portion thereof to create an immune response, extracting antibody-producing cells from the immunized animal; isolating RNA encoding heavy and light chains of antibodies of the invention from the extracted cells, reverse transcribing the RNA to produce cDNA, amplifying the cDNA using primers, and inserting the cDNA into a phage display vector such that antibodies are expressed on the phage. Recombinant anti-GRP78 antibodies of the invention may be obtained in this way.

Recombinant human anti-GRP78 antibodies of the invention can also be isolated by screening a recombinant combinatorial antibody library. Preferably the library is a scFv phage display library, generated using human $V_L$ and $V_H$ cDNAs prepared from mRNA isolated from B cells. Methods for preparing and screening such libraries are known in the art. Kits for generating phage display libraries are commercially available (e.g., the Pharmacia Recombinant Phage Antibody System, catalog no. 27-9400-01; and the Stratagene SurfZAP™ phage display kit, catalog no. 240612). There also are other methods and reagents that can be used in generating and screening antibody display libraries (see, e.g., U.S. Pat. No. 5,223,409; PCT Publication Nos.

WO 92/18619, WO 91/17271, WO 92/20791, WO 92/15679, WO 93/01288, WO 92/01047, WO 92/09690; Fuchs et al., Bio/Technology 9:1370-1372 (1991); Hay et al., Hum. Antibod. Hybridomas 3:81-85 (1992); Huse et al., Science 246:1275-1281 (1989); McCafferty et al., Nature 348:552-554 (1990); Griffiths et al., EMBO J. 12:725-734 (1993); Hawkins et al., J. Mol. Biol. 226:889-896 (1992); Clackson et al., Nature 352:624-628 (1991); Gram et al., Proc. Natl. Acad. Sci. USA 89:3576-3580 (1992); Garrad et al., Bio/Technology 9:1373-1377 (1991); Hoogenboom et al., Nuc. Acid Res. 19:4133-4137 (1991); and Barbas et al., Proc. Natl. Acad. Sci. USA 88:7978-7982 (1991), each incorporated herein by reference for purposes of teaching preparation and screening of phase display libraries.

Human antibodies are also produced by immunizing a non-human, transgenic animal comprising within its genome some or all of human immunoglobulin heavy chain and light chain loci with a human IgE antigen, e.g., a XenoMouse™ animal (Abgenix, Inc./Amgen, Inc.—Fremont, Calif.). XenoMouse™ mice are engineered mouse strains that comprise large fragments of human immunoglobulin heavy chain and light chain loci and are deficient in mouse antibody production. See, e.g., Green et al., Nature Genetics 7:13-21 (1994) and U.S. Pat. Nos. 5,916,771, 5,939,598, 5,985,615, 5,998,209, 6,075,181, 6,091,001, 6,114,598, 6,130,364, 6,162,963 and 6,150,584. See also WO 91/10741, WO 94/02602, WO 96/34096, WO 96/33735, WO 98/16654, WO 98/24893, WO 98/50433, WO 99/45031, WO 99/53049, WO 00/09560, and WO 00/037504. XenoMouse™ mice produce an adult-like human repertoire of fully human antibodies and generate antigen-specific human antibodies. In some embodiments, the XenoMouse™ mice contain approximately 80% of the human antibody V gene repertoire through introduction of megabase sized, germline configuration fragments of the human heavy chain loci and kappa light chain loci in yeast artificial chromosome (YAC). In other embodiments, Xeno-Mouse™ mice further contain approximately all of the human lambda light chain locus. See Mendez et al., Nature Genetics 15:146-156 (1997), Green and Jakobovits, J. Exp. Med. 188:483-495 (1998), and WO 98/24893 (each incorporated by reference in its entirety for purposes of teaching the preparation of fully human antibodies). In another aspect, the present invention provides a method for making anti-GRP78 antibodies from non-human, non-mouse animals by immunizing non-human transgenic animals that comprise human immunoglobulin loci with an GRP78 antigen. One can produce such animals using the methods described in the above-cited documents.

Identification of Anti-GRP78 Antibodies

The present invention provides monoclonal antibodies that inhibit and neutralize the action of GRP78. In particular, the antibodies of the present invention bind to cell surface GRP78 and inhibit signaling through the PI3K/AKT pathway. The antibodies of the present invention include antibodies that bind to the same epitope as the monoclonal antibody designated MAb159.

Candidate anti-GRP78 antibodies were tested by enzyme linked immunosorbent assay (ELISA), Western immunoblotting, or other immunochemical techniques. Assays performed to characterize the individual antibodies included: 1) ability to promote tumor cell apoptosis and inhibits PI3K signaling; 2) ability to localize to tumor but not normal organs in vivo; 3) ability to inhibit various xenograft tumor growths and tumor metastasis; 4) ability to reduce proliferation, induce apoptosis, impair tumor vasculature, and inhibit PI3K signaling in tumor xenografts; 5) ability to suppress Pten deletion induced leukemogenesis; 6) ability to inhibit tumor metastasis and 7) ability to suppress PTEN deletion induced prostate and uterine cancer progression and leukemogenesis. Experimental details are described in the Examples.

Antibodies of the present invention may also be described or specified in terms of their cross-reactivity. Antibodies that bind GRP78 polypeptides, which have at least 95%, at least 90%, at least 85%, at least 80%, at least 75%, at least 70%, at least 65%, at least 60%, at least 55%, and at least 50% identity (as calculated using methods known in the art and described herein) to human cell surface GRP78 are also included in the present invention.

Further included in the present invention are antibodies that bind to the same epitope as the anti-GRP78 antibodies of the present invention. To determine if an antibody can compete for binding to the same epitope as the epitope bound by the anti-GRP78 antibodies of the present invention, a cross-blocking assay, e.g., a competitive ELISA assay, can be performed. In an exemplary competitive ELISA assay, GRP78 coated on the wells of a microtiter plate is pre-incubated with or without candidate competing antibody and then the biotin-labeled anti-GRP78 antibody of the invention is added. The amount of labeled anti-GRP78 antibody bound to the GRP78 antigen in the wells is measured using avidin-peroxidase conjugate and appropriate substrate. The antibody can be labeled with a radioactive or fluorescent label or some other detectable and measurable label. The amount of labeled anti-GRP78 antibody that bound to the antigen will have an indirect correlation to the ability of the candidate competing antibody (test antibody) to compete for binding to the same epitope, i.e., the greater the affinity of the test antibody for the same epitope, the less labeled antibody will be bound to the antigen-coated wells. A candidate competing antibody is considered an antibody that binds substantially to the same epitope or that competes for binding to the same epitope as an anti-GRP78 antibody of the invention if the candidate antibody can block binding of the GRP78 antibody by at least 20%, preferably by at least 20-50%, even more preferably, by at least 50% as compared to the control performed in parallel in the absence of the candidate competing antibody. It will be understood that variations of this assay can be performed to arrive at the same quantitative value.

In various embodiments, the antibodies or antigen-binding fragments thereof comprise a light chain variable domain comprising a sequence of amino acids that differs from the sequence of a light chain variable domain having the amino acid sequence set forth in SEQ ID NOs: 23, 25, 27 or 29 only at 15, 14, 13, 12, 11, 10, 9, 8, 7, 6, 5, 4, 3, 2, 1 or 0 residues, wherein each such sequence difference is independently either a deletion, insertion, or substitution of one amino acid residue. In other embodiments, the light-chain variable domain comprises a sequence of amino acids that is at least 70%, 75%, 80%, 85%, 90%, 95%, 97%, or 99% identical to the sequence of a light chain variable domain having the amino acid sequence set forth in SEQ ID NOs: 23, 25, 27 or 29. In another embodiment, the light chain variable domain comprises a sequence of amino acids that is encoded by a nucleotide sequence that is at least 70%, 75%, 80%, 85%, 90%, 95%, 97%, or 99% identical to a polynucleotide sequence having the sequence of SEQ ID NO: 24, 26, 28 or 30. In another embodiment, the light chain variable domain comprises a sequence of amino acids that is encoded by a polynucleotide that hybridizes under moderately stringent conditions to the complement of a polynucleotide that encodes a light chain variable domain having the sequence of SEQ ID NO: 24, 26, 28 or 30. In another embodiment, the light chain variable domain comprises a sequence of amino acids that is encoded by a polynucleotide that hybridizes under stringent conditions to the complement of a polynucleotide that encodes a light chain variable domain having the sequence of SEQ ID NO: 24, 26, 28 or 30.

In various embodiments, the antibodies or antigen-binding fragments thereof comprise a heavy chain variable domain comprising a sequence of amino acids that differs from the sequence of a heavy chain variable domain having the amino acid sequence set forth in SEQ ID NOs: 13, 15, 17, 19 and 21 only at 15, 14, 13, 12, 11, 10, 9, 8, 7, 6, 5, 4, 3, 2, 1 or 0 residues, wherein each such sequence difference is independently either a deletion, insertion, or substitution of one amino acid residue. In other embodiments, the heavy-chain variable domain comprises a sequence of amino acids that is at least 70%, 75%, 80%, 85%, 90%, 95%, 97%, or 99% identical to the sequence of a heavy chain variable domain having the amino acid sequence set forth in SEQ ID NOs: 13, 15, 17, 19 or 21. In another embodiment, the heavy chain variable domain comprises a sequence of amino acids that is encoded by a nucleotide sequence that is at least 70%, 75%, 80%, 85%, 90%, 95%, 97%, or 99% identical to a polynucleotide sequence having the sequence of SEQ ID NO: 14, 16, 18, 20 or 22. In another embodiment, the heavy chain variable domain comprises a sequence of amino acids that is encoded by a polynucleotide that hybridizes under moderately stringent conditions to the complement of a polynucleotide that encodes a heavy chain variable domain having the sequence of SEQ ID NO: 14, 16, 18, 20 or 22. In another embodiment, the heavy chain variable domain comprises a sequence of amino acids that is encoded by a polynucleotide that hybridizes under stringent conditions to the complement of a polynucleotide that encodes a heavy chain variable domain having the sequence of SEQ ID NO: 14, 16, 18, 20 or 22.

Antibodies or antigen-binding fragments thereof of the invention can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a IgA-, IgD-, IgE-, IgG- and IgM-type heavy chain constant region. In certain embodiments, the light or heavy chain constant region is a fragment, derivative, variant, or mutein of a naturally occurring constant region.

In various embodiments of the present invention, the antibody or antigen-binding fragment is a murine antibody comprising the heavy chain variable region sequence set forth in SEQ ID NO: 9:

(SEQ ID NO: 9)
QAQLQQPGAELVKPGASVRLSCKASGYTFFSYWMHWVKQRPGQGLEWIGE

INPGNGRTNYNEKFKRKATLTVDKSSSTAYMQLNSLTSEDSAVYYCATLY

YYDGTYDYWGQGTTLTVSS and the light chain variable region sequence set forth in SEQ ID NO: 11:

(SEQ ID NO: 11)
DIVMTQSHKFMSTSVGDRVSVTCKASQNVGTDVAWYQQKPGQSPKALIYW

ASNRFTGVPDRFTGSGSGTDFTLTINNVQSEDLVDYFCQQYSSSPWTFGG

GTKLEIK

In various embodiments the antibody is a humanized antibody which comprises the heavy chain variable region having the amino acid sequence set forth in SEQ ID NO: 21:

(SEQ ID NO: 21)
QAQLVQSGAEVKKPGASVKVSCKASGYTFTSYWMHWVRQAPGQGLEWIGE

INPGNGRTNYNEKFKRRVTITVDKSASTAYMELSSLRSEDTAVYYCATLY

YYDGTYDYWGQGTTVTVSS and the light chain variable region having the amino acid sequence set forth in SEQ ID NO: 23:

(SEQ ID NO: 23)
DIVMTQSPSFLSASVGDRVTITCKASQNVGTDVAWYQQKPGKAPKALIYW

ASNRFTGVPDRFTGSGSGTDFTLTISSLQSEDVADYFCQQYSSSPWTFGG

GTKVEIK

In certain alternative embodiments, the antibody is an antibody comprising a heavy chain and a light chain, wherein heavy chain comprises a heavy chain variable region, and wherein the heavy chain variable region comprises a sequence that has at least about 80%, at least about 85%, at least about 90%, 91%, 92%, 93%, 94%, 95%, 96%, 97%, 98%, or at least about 99% identity to the amino acid sequence as set forth in SEQ ID NO: 21, or its corresponding polynucleotide sequence SEQ ID NO: 22:

(SEQ ID NO: 22)
Caggcccagctggtgcagtctggcgccgaggtgaagaaacctggcgcctc cgtgaaggtgtcctgcaaggcctccggctaaccttcaccagctactggat gcactgggtgcggcaggcccccaggccagggactggaatggatcggcgaga tcaaccccggcaacggccggaccaactacaacgagaagttcaagcggaga gtgaccatcaccgtggacaagtccgcctccaccgcctacatggaactgtc ctccctgcggagcgaggacaccgeegtgtactactgcgccaccctgtact actacgacggcacctacgactactggggccagggcaccaccgtgaccgtg tctagc and wherein the light chain comprises a light chain variable region, and wherein the light chain variable region comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 23, or its corresponding polynucleotide sequence SEQ ID NO: 24:

(SEQ ID NO: 24)
gacatcgtgatgacccagtcccccagcttcctgtccgcctccgtgggc gacagagtgaccatcacatgcaaggcctcccagaacgtgggcaccgac gtggcctggtatcagcagaagcccggcaaggcccccaaggccctgatc tactgggcctccaaccggttcaccggcgtgcccgacagattcaccggc tctggctccggcaccgacttcaccctgaccatctccagcctgcagtcc gaggacgtggccgactacttctgccagcagtactcctccagcccctgg accttcggcggaggcaccaaggtggaaatcaag In various embodiments the antibody is a humanized antibody which comprises the heavy chain variable region having the amino acid sequence set forth in SEQ ID NO: 15:

(SEQ ID NO: 15)
QAQLVQSGAEVKKPGASVKLSCKASGYTFTSYWMHWVKQAPGQGLEWI

GEINPGNGRTNYNEKFKRRATLTVDKSASTAYMELSSLRSEDTAVYYC

ATLYYYDGTY DYWGQGTTVTVSS and the light chain viable region having the amino acid sequence set forth in SEQ ID NO: 27:

(SEQ ID NO: 27)
DIVMTQSPSSLSASVGDRVTITCKASQNVGTDV AWYQQKPGKAPKAL

IYWASNRFTGVPDRFSGSGSGTDFTLTISSLQAEDVADYFCQQYSSSP

WTFGGGTKVEIK

In certain alternative embodiments, the antibody is an antibody comprising a heavy chain and a light chain, wherein heavy chain comprises a heavy chain variable region, and wherein the heavy chain variable region comprises a sequence that has at least about 80%, at least about 85%, at least about 90%, 91%, 92%, 93%, 94%, 95%, 96%, 97%, 98%, or at least about 99% identity to the amino acid sequence as set forth in SEQ ID NO: 15, or its corresponding polynucleotide sequence SEQ ID NO: 16:

(SEQ ID NO: 16)
Caggcccagctggtgcagtctggcgccgaggtgaagaaacctggcgcc tccgtgaagctgtcctgcaaggcctccggctacaccttcaccagctac tggatgcactgggtgaaacaggccccaggccagggactggaatggatc ggcgagatcaacccoggcaacggccggaccaactacaacgagaagttc aagcggagagccaccctgaccgtggacaagtccgcctccaccgcctac atggaactgtcctccctgcggagcgaggacaccgeegtgtactactgc geeaccctgtactactacgacggcacctacgactactggggccagggc accaccgtgaccgtgtctagc and wherein the light chain comprises a light chain variable region, and wherein the light chain variable region comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 27, or its corresponding polynucleotide sequence SEQ ID NO: 28:

(SEQ ID NO: 28)
gacatcgtgatgacccagtcccccagctccctgtccgcctccgtgggc gacagagtgaccatcacatgcaaggcctcccagaacgtgggcaccgac gtggcctggtatcagcagaagcccggcaaggcccccaaggccctgatc tactgggcctccaaccggttcaccggcgtgcccgacagattctccggc tctggctccggcaccgacttcaccctgaccatctccagcctgcaggcc gaggacgtggccgactacttctgccagcagtactcctccagcccctgg accttcggcggaggcaccaaggtggaaatcaag In various embodiments the antibody is a humanized antibody which comprises the heavy chain variable region having the amino acid sequence set forth in SEQ ID NO: 13:

(SEQ ID NO: 13)
QAQLVQSGAELKKPGASVKLSCKASGYTFTSYWMHWVKQAPGQGLEWI

GEINPGNGRTNYNEKFKRRATLTVDKSASTAYMELSSLRSEDSAVYYC

ATLYYYDGTYDYWGQGTTVTVSS and the light chain variable region having the amino acid sequence as set forth in SEQ ID NO: 23 defined above.

In certain alternative embodiments, the antibody is an antibody comprising a heavy chain and a light chain, wherein heavy chain comprises a heavy chain variable region, and wherein the heavy chain variable region comprises a sequence that has at least about 80%, at least about 85%, at least about 90%, 91%, 92%, 93%, 94%, 95%, 96%, 97%, 98%, or at least about 99% identity to the amino acid sequence as set forth in SEQ ID NO: 13, or its corresponding polynucleotide sequence SEQ ID NO: 14:

(SEQ ID NO: 14)
Caggcccagctggtgcagtctggcgeegagctgaagaaacctggcgcc tccgtgaagctgtcctgcaaggcctccggctacaccttcaccagctac tggatgcactgggtgaaacaggccccaggccagggactggaatggatc ggcgagatcaaccccggcaacggccggaccaactacaacgagaagttc aagcggagagccaccctgaccgtggacaagtccgcctccaccgcctac atggaactgtcctccctgcggagcgaggactccgeegtgtactactgc gccaccctgtactactacgacggcacctacgactactggggccagggc accaccgtgaccgtgtctagc and wherein the light chain comprises a light chain variable region, and wherein the light chain variable region comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 23 defined above, or its corresponding polynucleotide sequence SEQ ID NO: 24 defined above.

In various embodiments the antibody is a humanized antibody which comprises the heavy chain variable region having an amino acid sequence as set forth in SEQ ID NO: 17:

(SEQ ID NO: 17)
QAQLVQSGAEVKKPGASVKLSCKASGYTFTSYWMHWVRQAPGQGLEWI

GEINPGNGRTNYNEKFKRRATLTVDKSASTAYMELSSLRSEDTAVYYC

ATLYYYDGTYDYWGQGTTVTVSS and the light chain variable region having an amino acid sequence as set forth in SEQ ID NO: 25:

(SEQ ID NO: 25)
DIVMTQSPSSLSASVGDRVTITCKASQNVGTDVAWYQQKPGKAPKALI

YWASNRFTGVPDRFTGSGSGTDFTLTISSLQAEDVADYFCQQYSSSPW

TFGGGTKVEIK

In certain alternative embodiments, the antibody is an antibody comprising a heavy chain and a light chain, wherein heavy chain comprises a heavy chain variable region, and wherein the heavy chain variable region comprises a sequence that has at least about 80%, at least about 85%, at least about 90%, 91%, 92%, 93%, 94%, 95%, 96%, 97%, 98%, or at least about 99% identity to the amino acid sequence as set forth in any of SEQ ID NO: 17, or its corresponding polynucleotide sequence SEQ ID NO: 18:

(SEQ ID NO: 18)
Caggcccagctggtgcagtctggcgccgaggtgaagaaacctggcgcc tccgtgaagctgtcctgcaaggcctccggctacaccttcaccagctac tggatgcactgggtgcggcaggccccaggccagggactggaatggatc ggcgagatcaacccggcaacggccggaccaactacaacgagaagttc aagcggagagccaccctgaccgtggacaagtccgcctccaccgcctac atggaactgtcctccctgcggagcgaggacaccgeegtgtactactgc gccaccctgtactactacgacggcacctacgactactggggccagggc accaccgtgaccgtgtctagc and wherein the light chain comprises a light chain viable region, and wherein the light chain viable region comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 25, or its corresponding polynucleotide sequence SEQ ID NO: 26:

(SEQ ID NO: 26)
gacatcgtgatgacccagtccccagctccctgtccgcctccgtgggc gacagagtgaccatcacatgcaaggcctcccagaacgtgggcaccgac gtggcctggtatcagcagaagcccggcaaggcccccaaggccctgatc tactgggcctccaaccggttcaccggcgtgcccgacagattcaccggc tctggctccggcaccgacttcaccctgaccatctccagcctgcaggcc gaggacgtggccgactacttctgccagcagtactcctccagcccctgg accttcggcggaggcaccaaggtggaaatcaag In various embodiments the antibody is a humanized antibody which comprises the heavy chain variable region having an amino acid sequence as set forth in SEQ ID NO: 19:

(SEQ ID NO: 19)
QAQLVQSGAEVKKPGASVKVSCKASGYTFTSYWMHWVRQAPGQGLEWI

GEINPGNGRTNYNEKFKRRATITVDKSASTAYMELSSLRSEDTAVYYC

ATLYYYDGTY DYWGQGTTVTVSS and the light chain variable region having an amino acid sequence as set forth in SEQ ID NO: 25 defined above.

In certain alternative embodiments, the antibody is an antibody comprising a heavy chain and a light chain, wherein heavy chain comprises a heavy chain variable region, and wherein the heavy chain variable region comprises a sequence that has at least about 80%, at least about 85%, at least about 90%, 91%, 92%, 93%, 94%, 95%, 96%, 97%, 98%, or at least about 99% identity to the amino acid sequence as set forth in any of SEQ ID NO: 19, or its corresponding polynucleotide sequence SEQ ID NO: 20:

(SEQ ID NO: 20)
caggcccagctggtgcagtctggcgccgaggtgaagaaacctggcgcc tccgtgaaggtgtcctgcaaggcctccggctacaccttcaccagctac tggatgcactgggtgcggcaggccccaggccagggactggaatggatc ggcgagatcaacccggcaacggccggaccaactacaacgagaagttc aagcggagagccaccatcaccgtggacaagtccgcctccaccgcctac atggaactgtcctccctgcggagcgaggacaccgeegtgtactactgc gccaccctgtactactacgacggcacctacgactactggggccagggc accaccgtgaccgtgtctagc and wherein the light chain comprises a light chain variable region, and wherein the light chain variable region comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 25 defined above, or its corresponding polynucleotide sequence SEQ ID NO: 26 defined above.

In various embodiments the antibody is a humanized antibody which comprises the heavy chain variable region having an amino acid sequence as set forth in SEQ ID NO: 19 defined above and the light chain variable region having an amino acid sequence as set forth in SEQ ID NO: 29:

(SEQ ID NO: 29)
DIQMTQSPSSLSASVGDRVTITCKASQNVGTDVAWYQQKPGKAPKALI

YWASNRFTGVPDRFSGSGSGTDFTLTISSLQAEDVADYFCQQYSSSPW

TFGGGTKVEIK

In certain alternative embodiments, the antibody is an antibody comprising a heavy chain and a light chain, wherein heavy chain comprises a heavy chain variable region, and wherein the heavy chain variable region comprises a sequence that has at least about 80%, at least about 85%, at least about 90%, 91%, 92%, 93%, 94%, 95%, 96%, 97%, 98%, or at least about 99% identity to the amino acid sequence as set forth in any of SEQ ID NO: 19 defined above, or its corresponding polynucleotide sequence SEQ ID NO: 20 defined above; and wherein the light chain comprises a light chain variable region, and wherein the light chain variable region comprises a sequence that has at least about 75%, at least about 80%, at least about 85%, at least about 90%, 91%, 92%, 93%, 94%, 95%, 96%, 97%, 98%, or at least about 99% identity to the amino acid sequence as set forth in SEQ ID NO: 29, or its corresponding polynucleotide sequence SEQ ID NO: 30:

(SEQ ID NO: 30)
gacatccagatgacccagtccccagctccctgtccgcctccgtgggc gacagagtgaccatcacatgcaaggcctcccagaacgtgggcaccgac gtggcctggtatcagcagaagcccggcaaggcccccaaggccctgatc tactgggcctccaaccggttcaccggcgtgcccgacagattctccggc tctggctccggcaccgacttcaccctgaccatctccagcctgcaggcc -continued
gaggacgtggccgactacttctgccagcagtactcctccagccctgg accttcggcggaggcaccaaggtggaaatcaag Examples of Humanized Anti-GRP78 Antibodies

| HCVR | LCVR |
|---|---|
| SEQ ID NO: 13 | SEQ ID NO: 23 |
| SEQ ID NO: 13 | SEQ ID NO: 25 |
| SEQ ID NO: 13 | SEQ ID NO: 27 |
| SEQ ID NO: 13 | SEQ ID NO: 29 |
| SEQ ID NO: 15 | SEQ ID NO: 23 |
| SEQ ID NO: 15 | SEQ ID NO: 25 |
| SEQ ID NO: 15 | SEQ ID NO: 27 |
| SEQ ID NO: 15 | SEQ ID NO: 29 |
| SEQ ID NO: 17 | SEQ ID NO: 23 |
| SEQ ID NO: 17 | SEQ ID NO: 25 |
| SEQ ID NO: 17 | SEQ ID NO: 27 |
| SEQ ID NO: 17 | SEQ ID NO: 29 |
| SEQ ID NO: 19 | SEQ ID NO: 23 |
| SEQ ID NO: 19 | SEQ ID NO: 25 |
| SEQ ID NO: 19 | SEQ ID NO: 27 |
| SEQ ID NO: 19 | SEQ ID NO: 29 |
| SEQ ID NO: 21 | SEQ ID NO: 23 |
| SEQ ID NO: 21 | SEQ ID NO: 25 |
| SEQ ID NO: 21 | SEQ ID NO: 27 |
| SEQ ID NO: 21 | SEQ ID NO: 29 |

Diagnostic Uses

Methods for the detection of GFP78 are provided herein, including methods for detecting cells expressing GRP78, such as, e.g., prostate cancer, uterine cancer, breast cancer, myeloid leukemia, lymphatic leukemia, small cell lung cancer, colon cancer, pancreatic cancer, glioma, and head-neck cancer. These methods can include contacting a sample from a subject with an antibody or antigen-binding fragment thereof, as disclosed herein. The methods can be used to detect a primary tumor, or can be used to detect metastases.

In certain embodiments, methods are provided for detecting cancer or confirming the diagnosis of cancer in a subject. The method includes contacting a biological sample from the subject with an isolated antibody or antigen-biding fragment thereof of the invention and detecting binding of the isolated human monoclonal antibody or antigen-binding fragment thereof to the sample. An increase in binding of the isolated human monoclonal antibody or antigen-binding fragment thereof to the sample as compared to binding of the isolated human monoclonal antibody or antigen-binding fragment thereof to a control sample detects cancer in the subject or confirms the diagnosis of cancer in the subject. The control can be a sample from a subject known not to have cancer, or a standard value. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, and spinal fluid.

In one embodiment, a kit is provided for detecting GRP78 in a biological sample, such as a blood sample. Kits for detecting a polypeptide will typically comprise a human antibody that specifically binds GRP78, such as any of the antibodies disclosed herein. In some embodiments, an antibody fragment, such as an Fv fragment is included in the kit. For in vivo uses, the antibody can be a scFv fragment. In a further embodiment, the antibody is labeled (for example, with a fluorescent, radioactive, or an enzymatic label).

In one embodiment, a kit includes instructional materials disclosing means of use of an antibody that specifically binds GRP78. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting GRP78 in a biological sample generally includes the steps of contacting the biological sample with an antibody which specifically reacts, under immunologically reactive conditions, to GRP78. The antibody is allowed to specifically bind under immunologically reactive conditions to form an immune complex, and the presence of the immune complex (bound antibody) is detected directly or indirectly.

In certain embodiments, the antibodies or antigen-binding fragments can be labeled or unlabeled for diagnostic purposes. Typically, diagnostic assays entail detecting the formation of a complex resulting from the binding of an antibody to GRP78. The antibodies can be directly labeled. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the antibodies can be used in assays, such as agglutination assays. Unlabeled antibodies can also be used in combination with another (one or more) suitable reagent which can be used to detect antibody, such as a labeled antibody (e.g., a second antibody) reactive with the first antibody (e.g., anti-idiotype antibodies or other antibodies that are specific for the unlabeled immunoglobulin) or other suitable reagent (e.g., labeled protein A).

The antibody or antigen-binding fragment provided herein may also be used in a method of detecting the susceptibility of a mammal to certain diseases. To illustrate, the method can be used to detect the susceptibility of a mammal to diseases which progress based on the amount of GRP78 present on cells and/or the number of GRP78-positive cells in a mammal. In one embodiment, the application provides a method of detecting susceptibility of a mammal to a tumor. In this embodiment, a sample to be tested is contacted with an antibody which binds to a GRP78 or portion thereof under conditions appropriate for binding of said antibody thereto, wherein the sample comprises cells which express GRP78 in normal individuals. The binding of antibody and/or amount of binding is detected, which indicates the susceptibility of the individual to a tumor, wherein higher levels of receptor correlate with increased susceptibility of the individual to a tumor.

In certain embodiments, the antibodies or antigen-binding fragments described herein can be used for in vivo imaging, e.g., MAb159 specifically recognizes surface GRP78, and thus can be used to image the tumor for personalized medicine and determine whether the amount of surface GRP78 in the tumor predicts disease progression and response to therapy.

In certain embodiments, the antibodies or antigen-binding fragments are attached to a label that is able to be detected (e.g., the label can be a radioisotope, fluorescent compound, enzyme or enzyme co-factor). The active moiety may be a radioactive agent, such as: radioactive heavy metals such as iron chelates, radioactive chelates of gadolinium or manganese, positron emitters of oxygen, nitrogen, iron, carbon, or gallium, $^{43}$K, $^{52}$Fe, $^{57}$Co, $^{67}$Cu, $^{67}$Ga, $^{68}$Ga, $^{123}$I, $^{125}$I, $^{131}$I, $^{132}$I, or $^{99}$Tc. A binding agent affixed to such a moiety may be used as an imaging agent and is administered in an amount effective for diagnostic use in a mammal such as a human and the localization and accumulation of the imaging agent is then detected. The localization and accumulation of the imaging agent may be detected by radioscintigraphy, nuclear magnetic resonance imaging, computed tomography or positron emission tomography.

Immunoscintigraphy using antibodies or antigen-binding fragments directed at GRP78 may be used to detect and/or diagnose cancers and vasculature. For example, monoclonal antibodies against the GRP78 marker labeled with $^{99}$Technetium, $^{111}$Indium, or $^{125}$Iodine may be effectively used for such imaging. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety. Typically 0.1-100 millicuries per dose of imaging agent, or 1-10 millicuries, or 2-5 millicuries are administered. Thus, the compositions disclosed are useful as imaging agents comprising a targeting moiety conjugated to a radioactive moiety comprise 0.1-100 millicuries, in some embodiments 1-10 millicuries, in some embodiments 2-5 millicuries, in some embodiments 1-5 millicuries.

Therapeutic Uses

In certain embodiments, the present application provides methods of inhibiting or reducing tumor growth and methods of treating an individual suffering from cancer. These methods involve administering to the individual a therapeutically effective amount of an antibody or antigen-binding fragment as described above. These methods are particularly aimed at therapeutic and prophylactic treatments of animals, and more particularly, humans.

In certain embodiments, the present application provides methods for promoting apoptosis comprising contacting cells with an effective amount of an antibody or antigen-binding fragment. In some embodiments, the cells are endothelial cells.

The present invention provides for a method of treating cancer cells in a patient, comprising administering to said patient a therapeutically effective amount (either as monotherapy or in a combination therapy regimen) of an antibody or antigen-binding fragment thereof of the present invention in pharmaceutically acceptable carrier, wherein such administration promotes growth inhibition and/or proliferation of a cancer cell. Specifically, an antibody or antigen-binding fragment thereof of the present invention is useful in treating disorders characterized as cancer. Such disorders include, but are not limited to solid tumors, such as cancers of the breast, respiratory tract, brain, reproductive organs, digestive tract, urinary tract, eye, liver, skin, head and neck, thyroid, parathyroid and their distant metastases, lymphomas, sarcomas, multiple myeloma and leukemias. Examples of breast cancer include, but are not limited to invasive ductal carcinoma, invasive lobular carcinoma, ductal carcinoma in situ, and lobular carcinoma in situ. Examples of cancers of the respiratory tract include, but are not limited to small-cell and non-small-cell lung carcinoma, as well as bronchial adenoma and pleuropulmonary blastoma. Examples of brain cancers include, but are not limited to brain stem and hypophtalmic glioma, cerebellar and cerebral astrocytoma, medulloblastoma, ependymoma, as well as neuroectodermal and pineal tumor. Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus. Tumors of the digestive tract include, but are not limited to anal, colon, colorectal, esophageal, gallbladder, gastric, pancreatic, rectal, small-intestine, and salivary gland cancers. Tumors of the urinary tract include, but are not limited to bladder, penile, kidney, renal pelvis, ureter, and urethral cancers. Eye cancers include, but are not limited to intraocular melanoma and retinoblastoma. Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma. Skin cancers include, but are not limited to squamous cell carcinoma, Kaposi's sarcoma, malignant melanoma, Merkel cell skin cancer, and non-melanoma skin cancer. Head-and-neck cancers include, but are not limited to nasopharyngeal cancer, and lip and oral cavity cancer. Lymphomas include, but are not limited to AIDS-related lymphoma, non-Hodgkin's lymphoma, cutaneous T-cell lymphoma, Hodgkin's disease, and lymphoma of the central nervous system. Sarcomas include, but are not limited to sarcoma of the soft tissue, osteosarcoma, malignant fibrous histiocytoma, lymphosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia. In certain embodiments, the cancer will be a cancer with high PI3K activity, e.g., prostate cancer, uterine cancer, breast cancer, myeloid leukemia, lymphatic leukemia, small cell lung cancer, colon cancer, pancreatic cancer, glioma, and head-neck cancer.

The present application provides for a method of inhibiting the growth of cancer cells in a subject comprising administering an effective amount of an antibody or antigen-binding fragment into the subject. The modulation may reduce or prevent the growth of the cancer cells of said subject, such as for example, by at least 10%, at least 25%, at least 50%, at least 75%, or at least 90%. As a result, where the cancer is a solid tumor, the modulation may reduce the size of the solid tumor by at least 10%, at least 25%, at least 50%, at least 75%, or at least 90%.

The inhibition of the cancer cell proliferation can be measured by cell-based assays, such as bromodeoxyuridine (BRDU) incorporation (Hoshino et al., Int. J. Cancer 38, 369 (1986); Campana et al., J. Immunol. Meth. 107:79 (1988)); [.sup.3H]-thymidine incorporation (Chen, J., Oncogene 13:1395-403 (1996); Jeoung, J., J. Biol. Chem. 270:18367-73 (1995); the dye Alamar Blue (available from Biosource International) (Voytik-Harbin et al., In Vitro Cell Dev Biol Anim 34:239-46 (1998)). The anchorage independent growth of cancer cells is assessed by colony formation assay in soft agar, such as by counting the number of cancer cell colonies formed on top of the soft agar (see Examples and Sambrook et al., Molecular Cloning, Cold Spring Harbor, 1989).

The inhibition of cancer cell growth in a subject may be assessed by monitoring the cancer growth in a subject, for example in an animal model or in human subjects. One exemplary monitoring method is tumorigenicity assays. In one example, a xenograft comprises human cells from a pre-existing tumor or from a tumor cell line. Tumor xenograft assays are known in the art and described herein (see, e.g., Ogawa et al., Oncogene 19:6043-6052 (2000)). In another embodiment, tumorigenicity is monitored using the hollow fiber assay, which is described in U.S. Pat. No. 5,698,413, which is incorporated herein by reference in its entirety.

The percentage of the inhibition is calculated by comparing the cancer cell proliferation, anchorage independent growth, or cancer cell growth under modulator treatment with that under negative control condition (typically without modulator treatment). For example, where the number of cancer cells or cancer cell colonies (colony formation assay), or PRDU or [$^3$H]-thymidine incorporation is A (under the treatment of modulators) and C (under negative control condition), the percentage of inhibition would be (C-A)/C× 100%.

In certain embodiments, the subject methods disclosed can be used alone. Alternatively, the subject methods may be used in combination with other conventional anti-cancer therapeutic approaches directed to treatment or prevention of proliferative disorders (e.g., tumor). For example, such methods can be used in prophylactic cancer prevention, prevention of cancer recurrence and metastases after surgery, and as an adjuvant of other conventional cancer therapy. The present application recognizes that the effectiveness of conventional cancer therapies (e.g., chemotherapy, radiation therapy, phototherapy, immunotherapy, and surgery) can be enhanced through the use of the antibody or antigen-binding fragment.

A wide array of conventional compounds have been shown to have anti-neoplastic activities. These compounds have been used as pharmaceutical agents in chemotherapy to shrink solid tumors, prevent metastases and further growth, or decrease the number of malignant T-cells in leukemic or bone marrow malignancies. Although chemotherapy has been effective in treating various types of malignancies, many anti-neoplastic compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments.

When the antibody or antigen-binding fragment disclosed herein is administered in combination with another conventional anti-neoplastic agent, either concomitantly or sequentially, such antibody or antigen-binding fragment may enhance the therapeutic effect of the anti-neoplastic agent or overcome cellular resistance to such anti-neoplastic agent. This allows decrease of dosage of an anti-neoplastic agent, thereby reducing the undesirable side effects, or restores the effectiveness of an anti-neoplastic agent in resistant T-cells.

Pharmaceutical compounds that may be used for combinatory anti-tumor therapy include, merely to illustrate: aminoglutethimide, amsacrine, anastrozole, asparaginase, beg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic anti-tumor compounds may be categorized by their mechanism of action into, for example, following groups: anti-metabolites/anti-cancer agents, such as pyrimidine analogs (5-fluorouracil, floxmidine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

The present antibodies and antigen-binding fragments thereof can be utilized to directly kill or ablate cancerous cells in vivo. Direct killing involves administering the antibodies (which are optionally fused to a cytotoxic drug) to a subject requiring such treatment. In some embodiments, the cancer comprises cancer cells expressing GRP78 at a higher level than noncancerous cells of a comparable tissue. Since the antibodies recognize GRP78 on cancer cells, any such cells to which the antibodies bind are destroyed. Where the antibodies are used alone to kill or ablate cancer cells, such killing or ablation can be effected by initiating endogenous host immune functions, such as CDC and/or ADCC. Assays for determining whether an antibody kills cells in this manner are within the purview of those skilled in the art.

Pharmaceutical Compositions

In one aspect, the present invention provides a pharmaceutical composition comprising an antibody or antigen-binding fragment thereof as described above. The pharmaceutical compositions, methods and uses of the invention thus also encompass embodiments of combinations (co-administration) with other active agents, as detailed below.

Generally, the antibodies of the invention or portions thereof are suitable to be administered as a formulation in association with one or more pharmaceutically acceptable excipient(s). The term 'excipient' is used herein to describe any ingredient other than the compound(s) of the invention. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody. Pharmaceutical compositions of the present invention and methods for their preparation will be readily apparent to those skilled in the art. Such compositions and methods for their preparation may be found, for example, in Remington's Pharmaceutical Sciences, 19th Edition (Mack Publishing Company, 1995). Pharmaceutical compositions are preferably manufactured under GMP conditions.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Any method for administering peptides, proteins or antibodies accepted in the art may suitably be employed for the antibodies and portions of the invention.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. Various embodiments include the intravenous and the subcutaneous routes.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

For example, in one aspect, sterile injectable solutions can be prepared by incorporating the anti-GRP78 antibody in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibodies of the invention can also be administered intranasally or by inhalation, typically in the form of a dry powder (either alone, as a mixture, or as a mixed component particle, for example, mixed with a suitable pharmaceutically acceptable excipient) from a dry powder inhaler, as an aerosol spray from a pressurised container, pump, spray, atomiser (preferably an atomiser using electrohydrodynamics to produce a fine mist), or nebuliser, with or without the use of a suitable propellant, or as nasal drops.

The pressurised container, pump, spray, atomizer, or nebuliser generally contains a solution or suspension of an antibody of the invention comprising, for example, a suitable agent for dispersing, solubilising, or extending release of the active, a propellant(s) as solvent.

Prior to use in a dry powder or suspension formulation, the drug product is generally micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules, blisters and cartridges for use in an inhaler or insufflator may be formulated to contain a powder mix of the compound of the invention, a suitable powder base and a performance modifier.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" of an antibody of the invention. The overall daily dose will typically be administered in a single dose or, more usually, as divided doses throughout the day.

The antibodies and antibody portions of the invention may also be formulated for an oral route administration. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

As used herein, the terms "co-administration", "co-administered" and "in combination with", referring to the antibodies of the invention and one or more other therapeutic agents, is intended to mean, and does refer to and include the following: simultaneous administration of such combination of antibody (antibodies) of the invention and therapeutic agent(s) to a patient in need of treatment, when such components are formulated together into a single dosage form which releases said components at substantially the same time to said patient; substantially simultaneous administration of such combination of antibody (antibodies) of the invention and therapeutic agent(s) to a patient in need of treatment, when such components are formulated apart from each other into separate dosage forms which are taken at substantially the same time by said patient, whereupon said components are released at substantially the same time to said patient; sequential administration of such combination of antibody (antibodies) of the invention and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of antibody (antibodies) of the invention and therapeutic agent(s) to a patient in need of treatment, when such components are formulated together into a single dosage form which releases said components in a controlled manner whereupon they are concurrently, consecutively, and/or overlappingly released at the same and/or different times to said patient, where each part may be administered by either the same or a different route.

"Therapeutically effective amount" refers to that amount of the therapeutic agent being administered which will relieve to some extent one or more of the symptoms of the disorder being treated.

Dosage regimens may be adjusted to provide the optimum desired response. For example, a single bolus may be administered, several divided doses may be administered over time or the dose may be proportionally reduced or increased as indicated by the therapeutic situation. It is especially advantageous to formulate parenteral compositions in dosage unit form for ease of administration and uniformity of dosage. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier. The specification for the dosage unit forms of the invention are generally dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this invention may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens are well-known in the relevant art and would be understood to be encompassed by the skilled artisan once provided the teachings disclosed herein.

For administration to human subjects, the total monthly dose of the antibodies or antibody portion of the invention is typically in the range 0.5-1200 mg per patient, depending, of course, on the mode of administration. For example, an intravenous monthly dose may require about 1-1000 mg/patient. The total monthly dose may be administered in single or divided doses and may, at the physician's discretion, fall outside of the typical range given herein.

An exemplary, non-limiting range for a therapeutically or prophylactically effective amount of an antibody or antibody portion of the invention is 1-1000 mg/patient/month. In one embodiment, the antibody or portion thereof of the invention may be administered at about 1-200 or 1-150 mg/patient/month.

Immunoconjugates

The application further provides immunoconjugates comprising an antibody or antigen-binding fragment thereof of the present invention conjugated (or linked) directly or indirectly to an effector molecule. In this regard, the term "conjugated" or "linked" refers to making two polypeptides into one contiguous polypeptide molecule. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. In certain embodiments, an antibody or antigen-binding fragment is joined to an effector molecule. In other embodiments, an antibody or antigen-binding fragment joined to an effector molecule is further joined to a lipid, a protein or peptide to increase its half-life in the body.

Accordingly in various embodiments, the antibodies of the present disclosure may be used to deliver a variety of effector molecules.

The effector molecule can be a detectable label, an immunotoxin, cytokine, chemokine, therapeutic agent, or chemotherapeutic agent.

Specific, non-limiting examples of immunotoxins include, but are not limited to, abrin, ricin, Pseudomonas exotoxin (PE, such as PE35, PE37, PE38, and PE40), diphtheria toxin (DT), botulinum toxin, cholix toxin, or modified toxins thereof, or other toxic agents that directly or indirectly inhibit cell growth or kill cells.

A "cytokine" is class of proteins or peptides released by one cell population which act on another cell as intercellular mediators. Cytokines can act as an immune-modulating agent. Examples of cytokines include lymphokines, monokines, growth factors and traditional polypeptide hormones. Thus, embodiments may utilize an interferon (e.g., IFN-α, IFN-β, and IFN-γ); tumor necrosis factor super family (TNFSF) member; human growth hormone; thyroxine; insulin; proinsulin; relaxin; prorelaxin; follicle stimulating hormone (FSH); thyroid stimulating hormone (TSH); luteinizing hormone (LH); hepatic growth factor; prostaglandin, fibroblast growth factor; prolactin; placental lactogen, OB protein; TNF-α; TNF-β; integrin; thrombopoietin (TPO); a nerve growth factor such as NGF-β; platelet-growth factor; TGF-α; TGF-β; insulin-like growth factor-I and -II; erythropoietin (EPO); colony stimulating factors (CSFs) such as macrophage-CSF (M-CSF); granulocyte-macrophage-CSF (GM-CSF); and granulocyte-CSF (G-CSF); an interleukin (IL-1 to IL-21), kit-ligand or FLT-3, angiostatin, thrombospondin, or endostatin. These cytokine include proteins from natural sources or from recombinant cell culture and biologically active equivalents of the native sequence cytokines.

Chemokines can also be conjugated to the antibodies disclosed herein. Chemokines are a superfamily of small (approximately about 4 to about 14 kDa), inducible and secreted pro-inflammatory cytokines that act primarily as chemoattractants and activators of specific leukocyte cell subtypes. Chemokine production is induced by inflammatory cytokines, growth factors and pathogenic stimuli. The chemokine proteins are divided into subfamilies (alpha, beta, and delta) based on conserved amino acid sequence motifs and are classified into four highly conserved groups—CXC, CC, C and CX3C, based on the position of the first two cysteines that are adjacent to the amino terminus. To date, more than 50 chemokines have been discovered and there are at least 18 human seven-transmembrane-domain (7TM) chemokine receptors. Chemokines of use include, but are not limited to, RANTES, MCAP, MCP-1, and fractalkine.

The therapeutic agent can be a chemotherapeutic agent. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2.sup.nd ed., ©2000 Churchill Livingstone, Inc; Baltzer L., Berkery R. (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). Useful chemotherapeutic agents for the preparation of immunoconjugates include auristatin, dolastatin, MMAE, MMAF, AFP, AEB, doxorubicin, daunorubicin, methotrexate, melphalan, chlorambucil, vinca alkaloids, 5-fluorouridine, mitomycin-C, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, procarbazine, topotecan, nitrogen mustards, cytoxan, etoposide, BCNU, irinotecan, camptothecins, bleomycin, idarubicin, dactinomycin, plicamycin, mitoxantrone, asparaginase, vinblastine, vincristine, vinorelbine, paclitaxel, and docetaxel and salts, solvents and derivatives thereof. In certain embodiments, the chemotherapeutic agent is auristatin E (also known in the art as dolastatin-10) or a derivative thereof as well as pharmaceutically salts or solvates thereof. Typical auristatin derivatives include AEB, AEVB, AFP, MMAF, and MMAE. The synthesis and structure of auristatin E and its derivatives, as well as linkers, are described in, e.g., U.S. Patent Application Publication No. 20030083263; U.S. Patent Application Publication No. 20050238629; and U.S. Pat. No. 6,884,869 (each of which is incorporated by reference herein in its entirety).

The effector molecules can be linked to an antibody or antigen-binding fragment of the present invention using any number of means known to those of skill in the art. Both covalent and noncovalent attachment means may be used. The procedure for attaching an effector molecule to an antibody varies according to the chemical structure of the effector molecule. Polypeptides typically contain a variety of functional groups; such as carboxylic acid (COOH), free amine ($-NH_2$) or sulthydryl ($-SH$) groups, which are available for reaction with a suitable functional group on an antibody to result in the binding of the effector molecule. Alternatively, the antibody is derivatized to expose or attach additional reactive functional groups. The derivatization may involve attachment of any of a number of linker molecules such as those available from Pierce Chemical Company, Rockford, Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

Procedures for conjugating the antibodies with the effector molecules have been previously described and are within the purview of one skilled in the art. For example, procedures for preparing enzymatically active polypeptides of the immunotoxins are described in WO84/03508 and WO85/03508, which are hereby incorporated by reference for purposes of their specific teachings thereof. Other techniques are described in Shih et al., Int. J. Cancer 41:832-839 (1988); Shih et al., Int. J. Cancer 46: 1101-1106 (1990); Shih et al., U.S. Pat. No. 5,057,313; Shih Cancer Res. 51:4192, International Publication WO 02/088172; U.S. Pat. No. 6,884,869; International Patent Publication WO 2005/081711; U.S. Published Application 2003-0130189 A; and US Patent Application No. 20080305044, each of which is incorporated by reference herein for the purpose of teaching such techniques.

An immunoconjugate of the present invention retains the immunoreactivity of the antibody or antigen-binding fragment, e.g., the antibody or antigen-binding fragment has approximately the same, or only slightly reduced, ability to bind the antigen after conjugation as before conjugation. As used herein, an immunoconjugate is also referred to as an antibody drug conjugate (ADC).

Polynucleotides and Antibody Expression

The application further provides polynucleotides comprising a nucleotide sequence encoding an anti-GRP78 antibody or antigen-binding fragments thereof. Because of the degeneracy of the genetic code, a variety of nucleic acid sequences encode each antibody amino acid sequence. The application further provides polynucleotides that hybridize under stringent or lower stringency hybridization conditions, e.g., as defined herein, to polynucleotides that encode an antibody that binds to hGRP78.

Stringent hybridization conditions include, but are not limited to, hybridization to filter-bound DNA in 6×SSC at about 45° C. followed by one or more washes in 0.2×SSC/0.1% SDS at about 50-65° C., highly stringent conditions such as hybridization to filter-bound DNA in 6×SSC at about 45° C. followed by one or more washes in 0.1×SSC/0.2% SDS at about 60° C., or any other stringent hybridization conditions known to those skilled in the art (see, for example, Ausubel, F. M. et al., eds. 1989 Current Protocols in Molecular Biology, vol. 1, Green Publishing Associates, Inc. and John Wiley and Sons, Inc., NY at pages 6.3.1 to 6.3.6 and 2.10.3).

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR. In one embodiment, the codons that are used comprise those that are typical for human or mouse (see, e.g., Nakamura, Y., Nucleic Acids Res. 28: 292 (2000)).

A polynucleotide encoding an antibody may also be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably polyA+ RNA, isolated from, any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

The present invention is also directed to host cells that express a GRP78 polypeptide and/or the anti-GRP78 antibodies of the invention. A wide variety of host expression systems known in the art can be used to express an antibody of the present invention including prokaryotic (bacterial) and eukaryotic expression systems (such as yeast, baculovirus, plant, mammalian and other animal cells, transgenic animals, and hybridoma cells), as well as phage display expression systems.

An antibody of the invention can be prepared by recombinant expression of immunoglobulin light and heavy chain genes in a host cell. To express an antibody recombinantly, a host cell is transformed, transduced, infected or the like with one or more recombinant expression vectors carrying DNA fragments encoding the immunoglobulin light and/or heavy chains of the antibody such that the light and/or heavy chains are expressed in the host cell. The heavy chain and the light chain may be expressed independently from different promoters to which they are operably-linked in one vector or, alternatively, the heavy chain and the light chain may be expressed independently from different promoters to which they are operably-linked in two vectors one expressing the heavy chain and one expressing the light chain. Optionally, the heavy chain and light chain may be expressed in different host cells.

Additionally, the recombinant expression vector can encode a signal peptide that facilitates secretion of the antibody light and/or heavy chain from a host cell. The antibody light and/or heavy chain gene can be cloned into the vector such that the signal peptide is operably-linked in-frame to the amino terminus of the antibody chain gene. The signal peptide can be an immunoglobulin signal peptide or a heterologous signal peptide. Preferably, the recombinant antibodies are secreted into the medium in which the host cells are cultured, from which the antibodies can be recovered or purified.

An isolated DNA encoding a HCVR can be converted to a full-length heavy chain gene by operably-linking the HCVR-encoding DNA to another DNA molecule encoding heavy chain constant regions. The sequences of human, as well as other mammalian, heavy chain constant region genes are known in the art. DNA fragments encompassing these regions can be obtained e.g., by standard PCR amplification. The heavy chain constant region can be of any type, (e.g., IgG, IgA, IgE, IgM or IgD), class (e.g., $IgG_1$, $IgG_2$, $IgG_3$ and $IgG_4$) or subclass constant region and any allotypic variant thereof as described in Kabat (supra).

An isolated DNA encoding a LCVR region may be converted to a full-length light chain gene (as well as to a Fab light chain gene) by operably linking the LCVR-encoding DNA to another DNA molecule encoding a light chain constant region. The sequences of human, as well as other mammalian, light chain constant region genes are known in the art. DNA fragments encompassing these regions can be obtained by standard PCR amplification. The light chain constant region can be a kappa or lambda constant region.

In addition to the antibody heavy and/or light chain gene(s), a recombinant expression vector of the invention carries regulatory sequences that control the expression of the antibody chain gene(s) in a host cell. The term "regulatory sequence" is intended to include promoters, enhancers and other expression control elements (e.g., polyadenylation signals), as needed, that control the transcription or translation of the antibody chain gene(s). The design of the expression vector, including the selection of regulatory sequences may depend on such factors as the choice of the host cell to be transformed, the level of expression of protein desired. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and/or polyoma virus.

Additionally, the recombinant expression vectors of the invention may can-y additional sequences, such as sequences that regulate replication of the vector in host cells (e.g., origins of replication) and one or more selectable marker genes. The selectable marker gene facilitates selection of host cells into which the vector has been introduced. For example, typically the selectable marker gene confers resistance to drugs, such as G418, hygromycin, or methotrexate, on a host cell into which the vector has been introduced. Preferred selectable marker genes include the dihydrofolate reductase (dhfr) gene (for use in dhfr-minus host cells with methotrexate selection/amplification), the neo gene (for G418 selection), and glutamine synthetase (GS) in a GS-negative cell line (such as NSO) for selection/amplification.

For expression of the light and/or heavy chains, the expression vector(s) encoding the heavy and/or light chains is introduced into a host cell by standard techniques e.g. electroporation, calcium phosphate precipitation, DEAE-dextran transfection, transduction, infection and the like. Although it is theoretically possible to express the antibodies of the invention in either prokaryotic or eukaryotic host cells, eukaryotic cells are preferred, and most preferably mammalian host cells, because such cells are more likely to assemble and secrete a properly folded and immunologically active antibody. Preferred mammalian host cells for expressing the recombinant antibodies of the invention include Chinese Hamster Ovary (CHO cells) [including dhfr minus CHO cells, as described in Urlaub and Chasin, Proc. Natl. Acad. Sci. USA 77:4216-20, 1980, used with a DHFR selectable marker, e.g. as described in Kaufman and Sharp, J. Mol. Biol. 159:601-21, 1982], NSO myeloma cells, COS cells, and SP2/0 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown under appropriate conditions known in the art. Antibodies can be recovered from the host cell and/or the culture medium using standard purification methods.

Host cells can also be used to produce portions, or fragments, of intact antibodies, e.g., Fab fragments or scFv molecules by techniques that are conventional. For example, it may be desirable to transfect a host cell with DNA encoding either the light chain or the heavy chain of an antibody of this invention. Recombinant DNA technology may also be used to remove some or all the DNA encoding either or both of the light and heavy chains that is not necessary for binding to human GRP78. The molecules expressed from such truncated DNA molecules are also encompassed by the antibodies of the invention.

The invention provides a host cell comprising a nucleic acid molecule of the present invention. Preferably a host cell of the invention comprises one or more vectors or constructs comprising a nucleic acid molecule of the present invention. For example, a host cell of the invention is a cell into which a vector of the invention has been introduced, said vector comprising a polynucleotide encoding a LCVR of an antibody of the invention and/or a polynucleotide encoding a HCVR of the invention. The invention also provides a host cell into which two vectors of the invention have been introduced; one comprising a polynucleotide encoding a LCVR of an antibody of the invention and one comprising a polynucleotide encoding a HCVR present in an antibody of the invention and each operably-linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes.

Once expressed, the intact antibodies, individual light and heavy chains, or other immunoglobulin forms of the present invention can be purified according to standard procedures of the art, including ammonium sulfate precipitation, ion exchange, affinity (e.g., Protein A), reverse phase, hydrophobic interaction column chromatography, hydroxyapatite chromatography, gel electrophoresis, and the like. Standard procedures for purification of therapeutic antibodies are described, for example, by Feng L 1, Joe X. Zhou, Xiaoming Yang, Tim Tressel, and Brian Lee in an article entitled "Current Therapeutic Antibody Production and Process Optimization" (BioProcessing Journal, September/October 2005)(incorporated by reference in its entirety for purposes of teaching purification of therapeutic antibodies). Additionally, standard techniques for removing viruses from recombinantly expressed antibody preparations are also known in the art (see, for example, Gerd Kem and Mani Krishnan, "Viral Removal by Filtration: Points to Consider" (Biopharm International, October 2006)). The effectiveness of filtration to remove viruses from preparations of therapeutic antibodies is known to be at least in part dependent on the concentration of protein and/or the antibody in the solution to be filtered. The purification process for antibodies of the present invention may include a step of filtering to remove viruses from the mainstream of one or more chromatography operations. Preferably, prior to filtering through a pharmaceutical grade nanofilter to remove viruses, a chromatography mainstream containing an antibody of the present invention is diluted or concentrated to give total protein and/or total antibody concentration of about 1 g/L to about 3 g/L. Even more preferably, the nanofilter is a DV20 nanofilter (e.g., Pall Corporation; East Hills, N.Y.). Substantially pure immunoglobulins of at least about 90%, about 92%, about 94% or about 96% homogeneity are preferred, and about 98 to about 99% or more homogeneity most preferred, for pharmaceutical uses. Once purified, partially or to homogeneity as desired, the sterile antibodies may then be used therapeutically, as directed herein.

In view of the aforementioned discussion, the present invention is further directed to an antibody obtainable by a process comprising the steps of culturing a host cell including, but not limited to a mammalian, plant, bacterial, transgenic animal, or transgenic plant cell which has been transformed by a polynucleotide or a vector comprising nucleic acid molecules encoding antibodies of the invention so that the nucleic acid is expressed and, optionally, recovering the antibody from the host cell culture medium.

In certain aspects, the present application provides hybridoma cell lines, as well as to the monoclonal antibodies produced by these hybridoma cell lines. The cell lines disclosed have uses other than for the production of the monoclonal antibodies. For example, the cell lines can be fused with other cells (such as suitably drug-marked human myeloma, mouse myeloma, human-mouse heteromyeloma or human lymphoblastoid cells) to produce additional hybridomas, and thus provide for the transfer of the genes encoding the monoclonal antibodies. In addition, the cell lines can be used as a source of nucleic acids encoding the anti-GRP78 immunoglobulin chains, which can be isolated and expressed (e.g., upon transfer to other cells using any suitable technique (see e.g., Cabilly et al., U.S. Pat. No. 4,816,567; Winter, U.S. Pat. No. 5,225,539)). For instance, clones comprising a rearranged anti-GRP78 light or heavy chain can be isolated (e.g., by PCR) or cDNA libraries can be prepared from mRNA isolated from the cell lines, and cDNA clones encoding an anti-GRP78 immunoglobulin chain can be isolated. Thus, nucleic acids encoding the heavy and/or light chains of the antibodies or portions thereof can be obtained and used in accordance with recombinant DNA techniques for the production of the specific immunoglobulin, immunoglobulin chain, or variants thereof (e.g., humanized immunoglobulins) in a variety of host T-cells or in an in vitro translation system. For example, the nucleic acids, including cDNAs, or derivatives thereof encoding variants such as a humanized immunoglobulin or immunoglobulin chain, can be placed into suitable prokaryotic or eukaryotic vectors (e.g., expression vectors) and introduced into a suitable host T-cell by an appropriate method (e.g., transformation, transfection, electroporation, infection), such that the nucleic acid is operably linked to one or more expression control elements (e.g., in the vector or integrated into the host T-cell genome). For production, host T-cells can be maintained under conditions suitable for expression (e.g., in the presence of inducer, suitable media supplemented with appropriate salts, growth factors, antibiotic, nutritional supplements, etc.), whereby the encoded polypeptide is produced. If desired, the encoded protein can be recovered and/or isolated (e.g., from the host T-cells or medium). It will be appreciated that the method of production encompasses expression in a host T-cell of a transgenic animal (see e.g., WO 92/03918, GenPharm International, published Mar. 19, 1992)(incorporated by reference in its entirety).

The following examples are offered to more fully illustrate the invention, but are not construed as limiting the scope thereof.

EXAMPLE 1

Generation of Monoclonal Antibodies Targeting Specifically to Surface GRP78

Human GRP78 (amino acids 1-650; without KDEL motif (SEQ ID NO: 33)) and with hexahistidine tag (SEQ ID NO: 33) on C-tenninus (designated as GRP78-His) was constructed, transiently expressed in 293T cells, purified through nickel-NTA column (Biorad, Hercules, Calif.) and used as an immunogen. Estimated purity of GRP78-His was higher than 95% based on SDS-PAGE Coomassie staining (FIG. 1A).

Female Swiss Webster mice were immunized three times (every second week) intraperitoneally (i.p.) with 50 µg of GRP78-His per mouse. Antigen was injected as 1:1 mixture with Complete Freund's Adjuvant (Sigma, St. Louis, Mo.) in the first immunization, and with Incomplete Freund's Adjuvant (Sigma, St. Louis, Mo.) in the second and third doses. Mice were given a final boost with 20 µg of GRP78-His through tail-vein injection, and splenocytes were harvested 4 days later for fusion with myeloma cell line NSO from ATCC (Allendale, N.J.). Hybridoma supernatants were screened for antibodies that immunoprecipitate GRP78 (without KDEL (SEQ ID NO: 33)) fused to alkaline phosphatase (AP). Selected monoclonal antibodies (MAb) were produced in BD CELLine cultivation system (BD Biosciences, Bedford, Mass.) following manufacturer's protocol. MAbs were purified with protein G affinity chromatography.

Estimated purity of MAbs was higher than 95% based on HPLC analysis and SDS-PAGE Coomassie staining.

One of the purified murine monoclonal antibodies, designated MAb159, was selected for further analysis. MAb159 comprises the heavy chain variable region sequence set forth in SEQ ID NO: 9 and the light chain variable region sequence set forth in SEQ ID NO: 11. The heavy chain variable region and the light chain variable region of MAb 159 are encoded by the nucleic acid sequences set forth in SEQ ID NOs: 10 and 12, respectively.

EXAMPLE 2

Characterization of Monoclonal Antibodies Targeting Surface GRP78

A. Binding Affinity

Figure 1B:
FIG. 1B depicts the result of the Scatchard assay to determine the affinity of MAb159 to GRP78.

The binding affinity of MAb159 to antigen was determined by Scatchard assay as described previously (Krasnoperov et al., Am. J. Pathol., 2010). MAb159 has high affinity to human GRP78 ($K_D$=1.7 nM) (FIG. 1B).

B. Binding Specificity

Breast carcinoma MCF7 cells were treated with 300 nM thapsigarin or DMSO for 16 hours and the whole cell lysates were subjected to Western blotting using MAb159 (signal in red) and HSP70 antibody (signal in green). 20 µg of whole-cell lysates were run on 4-20% Trisglycine gradient gel (Biorad, Hercules, Calif.) and transferred onto nitrocellulose membrane (BioRad, Hercules, Calif.). The same membrane was used for both antibodies. The membrane was blocked with 5% non-fat dry milk in TBS and 0.05% Tween-20 (TBST) for 40 min, and then incubated with 1 µg/ml primary antibody at 4° C. overnight. Membrane was washed three times for 10 min each and incubated with secondary HRP-labeled or IRDye labeled secondary antibody for 40 min. After three times wash with TBST, HRP signal was detected using Femto Maximum Sensitivity chemiluminescent substrate from Thermo Scientific, and IRDye signal was detected by Odyssey (LICOR, Lincoln, Nebr.). MAb159 only recognized GRP78, which was significantly induced after thapsigarin treatment, and MAb159 had no cross-reactivity to GRP78's closet paralogue, HSP70 (data not shown).

C. Binding Specificity (Cancer Cells Vs. Normal Cells)

Figure 1C:
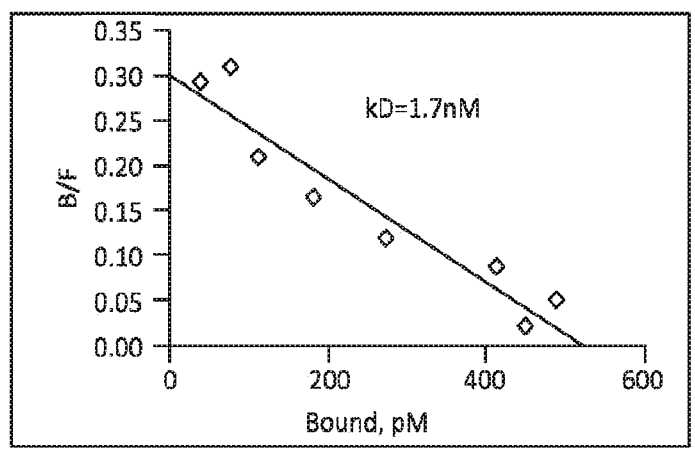
FIG. 1C shows images of various live cells that were incubated with MAb159 at 4° C. Normal human dermal fibroblast (NHFD) cells (top left), C4-2B cells (prostate cancer)(top right), MCF7 cells (bottom left), and glucose starved MCF7 cells (bottom right) were evaluated. Surface GRP78 staining is shown in green. Nuclei were counterstained with DAPI (blue).

Normal cells and various cancer cells were incubated with MAb159 at 4° C. Nuclei were counterstained with DAPI (blue). Surface GRP78 staining (green) can be seen on the surface of cancer cells C4-2B (a prostate cancer cell) and MCF7 (breast carcinoma cells)), but not on normal human dermal fibroblasts (NHFD) (FIG. 1C). Glucose starvation for 2 days significantly increased the level of surface GRP78 on MCF7 cells (FIG. 1C, bottom left). This is consistent with the previous findings that surface GRP78 is only present on cancer cell and its amount significantly increases when the cell is under stress (Ni et al., Biochem., J., 2:181-188, 2011; Zhang et al., J. Biol. Chem., 20:15065-15075, 2010).

D. Binding Specificity (Human GRP78 vs. Mouse GRP78)

Figure 7A:
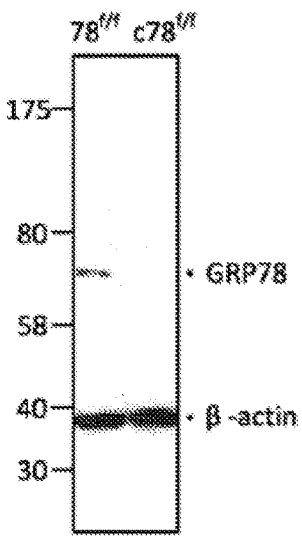
FIG. 7A is an immunoblot showing that MAb159 recognized the GRP78 protein band in mouse embryo fibroblast (MEF) lysates prepared from Grp78 floxed/floxed mice. The GRP78 band was absent in the c78f/f MEFs where the Grp78 alleles were deleted by treatment of the MEFs with adenovirus expressing the cre-recombinase. The blot was reprobed with anti b-actin antibody to confirm equivalent protein loading in both lanes.

Mouse GRP78 is 99% conserved in amino acids with human GRP78. As depicted in FIG. 7A, MAb159 in immunoblot assays recognized the GRP78 protein band in mouse embryo fibroblast (MEF) lysates prepared from the Grp78 floxed/floxed mice. The GRP78 band was absent in the c78f/fMEFs where the Grp78 alleles were deleted by treatment of the MEFs with adenovirus expressing the cre-recombinase. The blot was reprobed with anti-β-actin antibody to confirm equivalent protein loading in both lanes. These results also show that MAb159 only immunoreacted with GRP78 in mouse protein lysates, confirming its specificity. (FIG. 7A)

E. Antibody Endocytosis

MAb159 was biotinylated with EZ-link biotin hydrazide from Thermo Scientific (Rockford, Ill.) following manufacturer's procedure. Glucose starved (2 days) MCF7 cells were treated with 10 µg/mL biotinylated MAb159 for 1 hour at 37° C. or at 4° C. The cells were then fixed with 4% paraformaldehyde for 20 min and washed with PBS for 3 times. Cells were permeabilized with 0.1% Triton X-100 and washed with PBS for 3 times. Subsequently cells were stained with streptavidin-FITC (Invitrogen) for 30 min at room temperature. Images were taken with a 100x objective on a Zeiss LSM 510 confocal microscope. When incubated with cells at normal growth temperature (37° C.), MAb159 underwent endocytosis and was localized to the intracellular endosomes (green) compared to fine ring like appearance at the cell surface at 4° C. which prevents endocytosis, i.e., endocytosis was observed only at 37° C.

EXAMPLE 3

Surface GRP78 Expression in Cancer Cells and Cancer Stem Cells

Utilizing the high specificity of MAb 159 and flow cytometry techniques described in Materials and Methods section below, we examined the expression of surface GRP78 in primary tumors and tumor cell lines. Cell surface GRP78 level was strikingly high (12-98%, median 52%) in freshly collected whole blood cells from 15 cases of chronic lymphocytic leukemia (CLL). Single cell suspension prepared from freshly collected breast cancer tissue and a cohort of human small cell lung carcinoma cells also showed substantial percent of cells with cell surface GRP78 (8 to 34% and 34-67%, respectively)(Table 1). In a collection of prostate cell lines, surface GRP78 level was hardly detectable in BPH (a benign hyperplastic prostatic epithelial cell line), but high in human prostate cancer cell line LNCaP and C4-2B and as well as two primary cell lines established from PTEN deficient mice CE1 and E2. Cancer cell lines such as HT29, Colo205, A549, and MCF7 also show surface GRP78 expression (data not shown).

TABLE 1

Expression of GRP78 on the Surface of Tumor Cells

| Cell | | Surface GRP78 positive percentage (%): Range (mean) |
|---|---|---|
| Primary CLL (15) | | 12-98 (52) |
| Primary Breast Cancer (3) | | 8-34 (22) |
| SCLC cell lines (4) | | 34-67 (54) |
| BPH | Non-cancerous prostate cell | 1.2 |
| LNCap | Human prostate cancer cell | 35.7 |
| C4-2B | | 72.3 |
| CE1 | House prostate cancer cell | 14.8 25.6 |

Surface CRP78 positive percentage was determined with flow cytometry. CLL, Chronic lymphocytic leukemia; SCLC, small cell lung carcinoma. C4-2B is an androgen independent clone derived from LNCap, E2 and CE1 are cell lines established from prostate specific PTEN knockout mice.

Figure 7B:
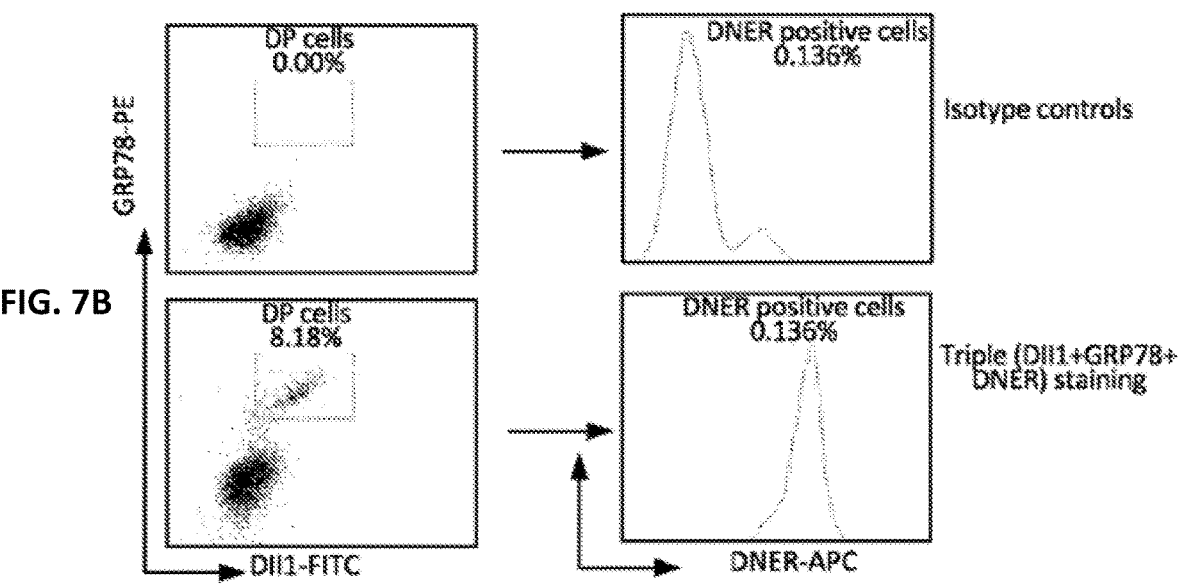
FIG. 7B shows the results of flow cytometry analysis where surface GRP78 is shown to co-express with Dll1 and DNER, two breast cancer stem cell markers. In the analysis, cells expressing both GRP78 and Dll1 were first isolated and then gated for DNER expression.

As tumor stem cells have also been shown to have cell surface GRP78 such as head-neck squamous cell carcinoma (Miharada et al., Cell. Stem Cell., 4:330-344, 2011), the present inventors examined the expression of cell surface GRP78 in triple negative (estrogen receptor, progesterone receptor, and Her2 negative) breast cancer stem-like cells shown to co-express DU I/DNER (Pece et al., Cell, I:62-73, 2010). Primary triple negative breast tumor tissue was processed for flow cytometry. Cells expressing both GRP78 and DU I were first isolated and then gated for DNER expression. In our analysis DU I and surface GRP78 were co-expressed and 80% of these double positive cells were also DNER positive (FIG. 7B), suggesting the concentration of surface GRP78 on cancer stem-like cells in triple negative breast cancer.

Figure 7C:
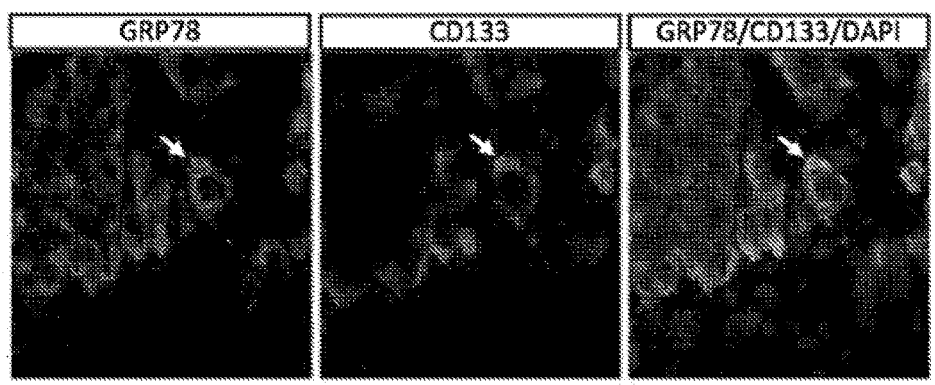
FIG. 7C shows stained images of primary head and neck tumor tissue was stained with MAb159 (green) and stem cell marker CD133 (red) antibodies. Arrow points out the co-localization of surface GRP78 and CD133. No permeabilization agent was used in the staining procedure. Nuclei were stained with DAPI (blue).
Figure 8A:
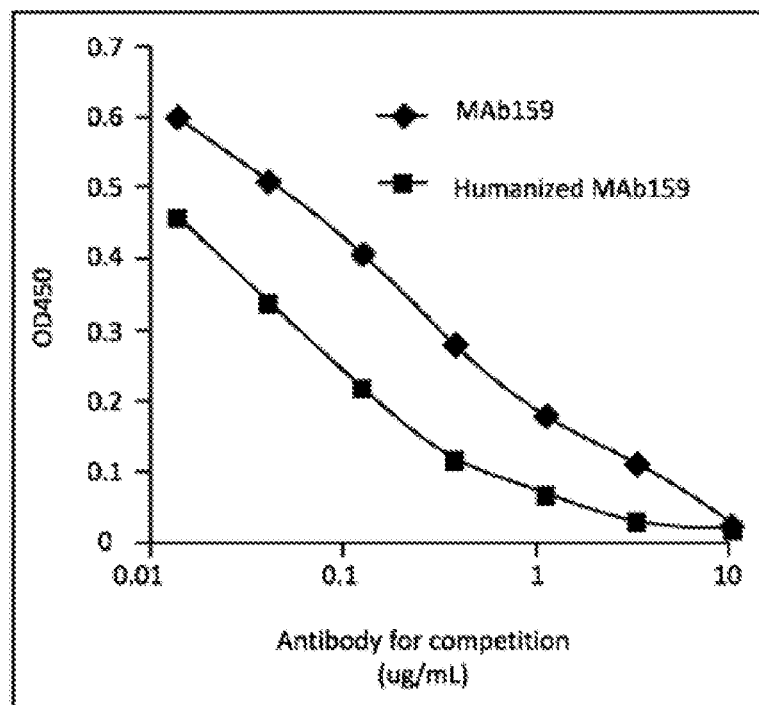
FIG. 8A shows a comparison of the affinity of MAb159 vs. humanized MAb159 in a competition ELISA. A dilution series of murine MAb159 and humanized MAb159 were tested against a fixed concentration of biotinylated murine MAb159 for binding to GRP78-His. The graph shows the binding of biotinylated MAb159 decreases with increasing amounts of both murine and humanized MAb159. Humanized MAb159 shows slightly better affinity for GRP78 than murine MAb159.
Figure 8B:
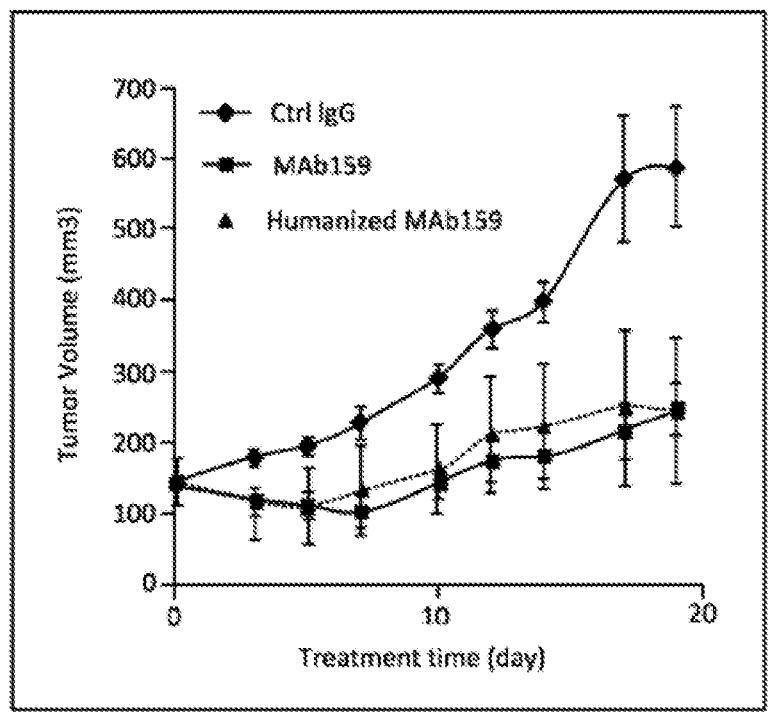
FIG. 8B shows a comparison of the anti-tumor activity of MAb159 and humanized MAb159A549 xenograft tumors were treated with normal mouse IgG, murine MAb159, and humanized MAb159 (n=8). Antibodies were administered at 10 mg/kg, 2 times a week. Data are presented as mean±SEM. Double asterisks indicate $P<0.005$, as determined by an unpaired 2-tail student T-test.

Primary head and neck tumor tissue was stained with MAb159 (green) and stem cell marker CD133 (red) antibodies. Arrow points out the co-localization of surface GRP78 and CD133. No permeabilization agent was used in the staining procedure. Nuclei were stained with DAPI (blue). Similarly, in head and neck primary tumor cells, surface GRP78 co-localized with stem like cell marker CD133 (FIG. 7C).

EXAMPLE 4

MAb159 Promotes Tumor Cell Apoptosis and Inhibits P13K Signaling

The effect of MAb159 on tumor cells was first tested in vitro. Cells were isolated as described above and seeded in 96-well plates at a density of $1\times10^4$ cells/well in a total volume of 100 μL. Quadruplet wells were treated with MAb159 (20 or 100 μg/mL) or 100 μg/mL normal mouse IgG (Rockland) for 3 days. 10 μL Alamar Blue (Invitrogen, Carlsbad, Calif.) was subsequently added to each well, incubated for 4 hours at 37° C., and fluorescent intensity was measured following manufacturer's instructions. When whole blood cells from patients with CLL (same as those identified in Table 1) were incubated with MAb159 or control IgG for 3 days, MAb159 treatment caused significant loss of cell viability while control IgG had no toxicity (data not shown).

Figure 13A:
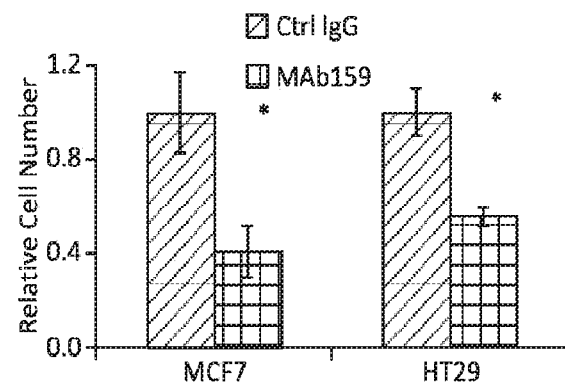
FIG. 13A shows that MAb159 reduced the viable cell number of glucose starved HT29 and MCF7 (determined by MTT assay) (top bar graph*=MAb159) and that MAb159 triggers apoptosis in glucose starved MCF7 cells determined by TUNEL assay (bottom blots). TUNEL signal is shown in green and nuclei are in blue. Data presented as mean±standard error.
Figure 13A:
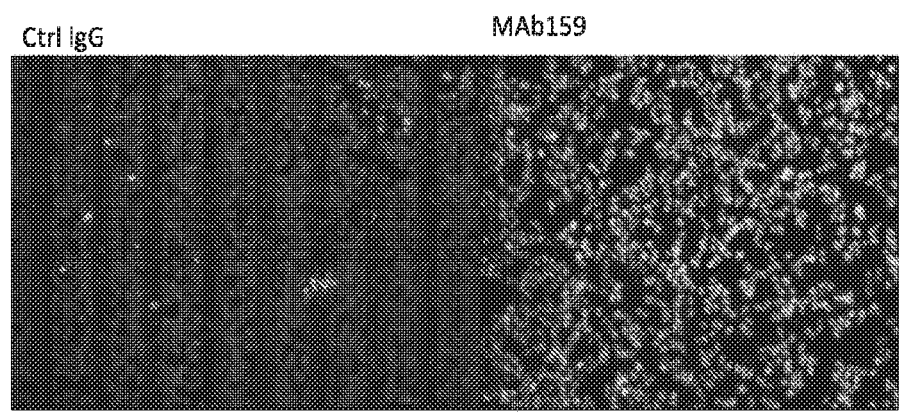
Figure 13B:
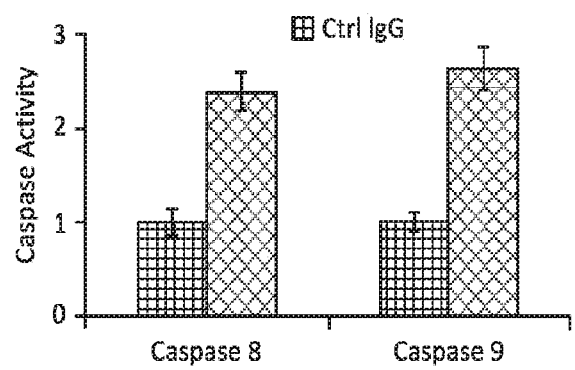
FIG. 13B shows that MAb159 induces caspase 8 and 9 activity as determined with a colorimetric assay kit. Data presented as mean±standard error.

We also tested the toxicity of the antibody in glucose starved HT29 and MCF7 cell lines with the expectation of increased efficacy of the antibody. For this analysis, cancer cells were seeded in 24-well plates at a density of $2\times10^4$ cells/well in a total volume of 500 μL. One day later, the medium was changed to growth medium without glucose. Triplicate wells were treated with 50 μg/mL MAb159 or control mouse IgG (Rockland, Gilbertsville, Pa.). 5 days after treatment, cell viability was assessed using 3-(4,5-dimethylthiazol-2-yl)-2,5-diphenyltetrazolium bromide (MTT) as described previously (Kumar, Singh, et al, 2006). MAb159 reduced (greater than 50%) the cell viability of colon and breast carcinoma cell lines HT29 and MCF7 under these culture conditions (FIG. 13A, top bar graph). We also wished to determine if the apoptosis is triggered at the cell surface. For this analysis, cells were processed for apoptosis analysis with caspase-8/9 colorimetric assay kit (R&D systems, Minneapolis, Minn.) and TdT-mediated dUTP nick-end labeling (TUNEL) assay kit (Promega, Madison, Wis.) following manufacturer's instructions. We then measured the levels of activated caspase 8 and caspase 9, which represent the activation of extrinsic and intrinsic apoptotic pathways, respectively. We further observed that MAb159 activated both caspase 8 and caspase 9, which represents extrinsic and intrinsic apoptotic pathways, respectively (FIG. 13B). This suggests that at least in part the loss of cell viability was initiated at the cell surface. Reduced viability may be caused by increased apoptosis in glucose starved MCF7 cells as determined by TUNEL assay (FIG. 13A, bottom blots).

Figure 2A:
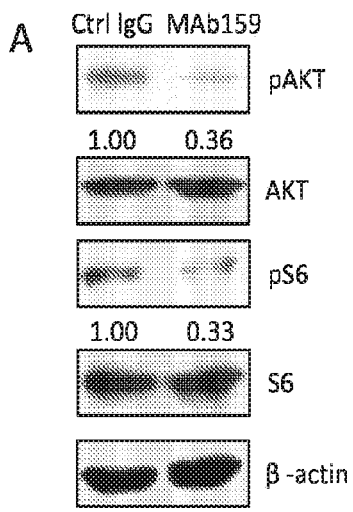
FIG. 2A shows a Western blot of glucose starved HT29 cells treated with 50 µg/mL MAb159 and then whole cell lysates subjected to Western blotting using MAb159 and control IgG antibody. Image J (NIH) was used for quantification of relative pAKT and pS6 level.

PI3K signaling pathway regulates many biological events in the cells including cell survival, and GRP78 has previously been shown to modulate PI3K activity. We thus examined whether cell surface GRP78 expressing tumor cells treated with MAb159 have alterations in PI3K activity as measured by the changes in phosphorylated AKT and S6 levels. For this analysis, glucose starved HT29 cells were incubated with 50 μg/mL MAb159 and whole cell lysates subjected to Western blot analysis using MAb159 and control IgG as described previously herein. Image J (NIH) was used for quantification of relative pKAT and pS6 level. We indeed found that both phosphorylated AKT and S6 levels were reduced in MAb159 treated cells compared to the controls (FIG. 2A). The above results indicate that MAb159 inhibits PI3K pathway.

EXAMPLE 5

Surface GRP78 Interacts with p85 Subunit of PI3K

Figure 2B:
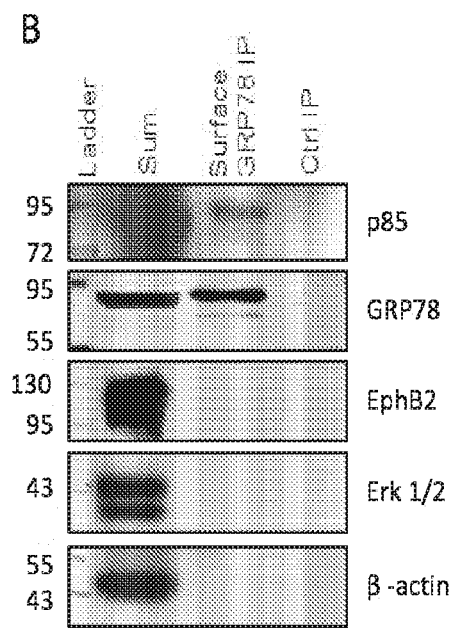
FIG. 2B shows a Western blot of a biotinylation-immunoprecipitation (IP) analysis where the interaction of surface GRP78 with p85, but not EphB2, Erk1/2, or beta-actin was detected. In the analysis, Flag tagged GRP78 (without KDEL (SEQ ID NO: 33)) was overexpressed in 293T cells, followed by surface protein biotinylation and IP. GRP78 IP and control IP were performed with a Flag antibody conjugated agarose beads and a mouse IgG conjugated agarose beads, respectively. "Sum" is the initial cell lysate.
Figure 2C:
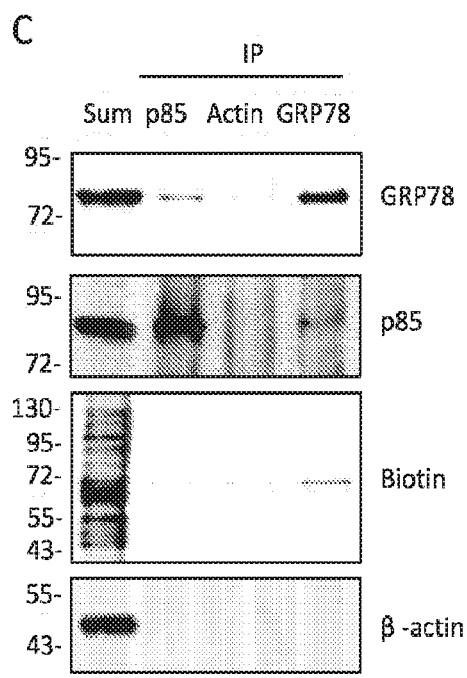
FIG. 2C shows a Western blot of a biotinylation-immunoprecipitation (IP) analysis (same as that used in FIG. 2B) where the interaction of endogenous surface GRP78 with p85 was detected in 293T cells treated with thapsigargin. IP was performed with protein G conjugated agarose and three mouse monoclonal antibodies.

In view of our findings in Example 4 that targeting cell surface GRP78 modulates PI3K signal, we wished to determine whether there is a direct interaction between cell surface GRP78 and PI3K components. For this analysis, we overexpressed a FLAG tagged GRP78 (without KDEL (SEQ ID NO: 33)), which has increased translocation to the cell surface (Zhang et al., J. Biol. Chem., 20:15065-15075, 2010), labeled the cell surface proteins with biotin and purified the biotin labeled proteins on monomeric avid beads. GRP78 was immunoprecipitated from this pool of surface proteins and its interacting partners were detected by Western blotting. Specifically, 293T cells growing on 10 cm dish were transfected with Flag tagged GRP78 (without KDEL (SEQ ID NO: 33)) alone or co-transfected with a human EphB2 full length expression vector. Three days after transfection, cells were rinsed with ice cold PBS twice and incubated with 0.5 mg/mL EZ-link Sulfo-NHS-LC-Biotin (Thermo scientific) with gentle shake at 4° C. for 30 min. Tris-HCl (pH 7.5) was added to a final concentration of 100 nM to stop the biotinylation reaction. The cells were rinsed with ice cold PBS twice and then lysed with lysis buffer (PBS, 2 mM NaF, 1 mM $Na_3VO_4$, 1× protease inhibitor cocktail, and 1% Triton X-100). The biotinylated surface proteins were purified with monomeric avidin-agarose beads (Thermo scientific, Rockford, Ill.) following manufacturer's instructions. The eluted biotinylated proteins were further incubated with beads conjugated with anti-Flag antibody M2 (Sigma, St. Louis, Mo.) at 4° C. overnight to pull down Flag-tagged GRP78. Beads were then washed two times with lysis buffer and the bound proteins were eluted with Laemmli SDS buffer (BioRad, Hercules, Calif.) supplemented with 50 mM dithiothreitol, followed by incubation for 5 min at 95° C. The negative control for IP was beads conjugated with normal mouse IgG from Rockland. In the study to see endogenous interaction of p85 and surface GRP78, before biotin labeling, 293T cells were treated with 300 nM thapsigargin for 16 hours instead. The immunoprecipitation was performed with protein G beads (Genescript, Piscataway, N.J.) and p85, GRP78, and beta-actin antibodies (all mouse IgG 1, 5 μg per reaction). As seen in FIG. 2B, GRP78 formed complex with p85, the regulatory subunit of PI3K, but not with ERK1/2 or a cell surface specific protein EphB2. We further confirmed this interaction under endogenous expression condition. Surface GRP78 level was first induced with thapsigargin followed by purification of cell surface proteins using biotin-avidin system as before. Co-immunoprecipitation of surface GRP78 and p85 was achieved with either GRP78 antibody or p85 antibody (FIG. 2C). These results provide the first evidence that surface GRP78 binds to PI3K component and suggest surface GRP78 may regulate PI3K signaling through direct complex formation with the PI3K subunits.

EXAMPLE 6

MAb159 Localizes to Tumor but not Normal Organs In Vivo

Figure 3A:
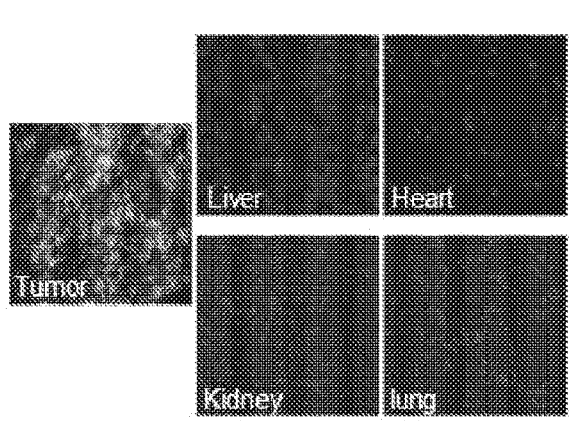
FIG. 3A shows images of tumor and normal organ tissue obtained from two HT29 tumor bearing mice that had been injected i.v. with biotinylated MAb159 (50 µg). Mice were sacrificed six hours after administration, the tissues were harvested, and MAb159 localization assessed. MAb159 localization detected with fluorochrome-conjugated streptavidin is in green. Nuclei were counterstained with DAPI (blue).

For these various studies, xenograft tumors were established as described in the Materials and Methods section below. We sought to determine whether MAb159 preferably localizes to tumor and not normal organs by tracking biotin labeled MAb159 in HT29 xenograft tumor bearing mice. Specifically, biotinylated MAb159 (50 µg) was administrated to two HT29 tumor bearing mice through i.v. injection. Six hours later the mice were sacrificed and the tissues were harvested and imaged for MAb159 localization. For immunofluorescence, fresh frozen tissue embedded in OCT was sectioned at 5 µm and fixed in phosphate-buffered 4% paraformaldehyde and washed in PBS. Sections were then blocked with goat serum and incubated with primary antibody overnight at 4° C. After washing in PBS, antibody binding was localized with fluorochrome-conjugated streptavidin. Nuclei were counterstained with 6-diamidino-2-phenylindole dihydrochloride hydrate (DAPI). Images were obtained with an Nikon Eclipse 80i fluorescence microscope and Meta Morph imaging series system. MAb159 localization was only detected in tumor, and not in the normal organs (including heart, liver, kidney, and lung), with fluorochrome-conjugated streptavidin (shown in green) (FIG. 3A). Nuclei were counterstained with DAPI (blue).

EXAMPLE 7

Affinity, Activity, and Specificity of Humanized MAb159

We next made humanized MAb159 to avoid potential immunogenicity in humans. The humanized MAb159 used for this analysis comprised the heavy chain variable region set forth in SEQ ID NO: 21 and the light chain variable region set forth in SEQ ID NO: 23. This antibody has affinity to GRP7S (FIG. SA) and efficacy in tumor growth inhibition (FIG. SB) comparable to the parental murine antibody.

Figure 3C:
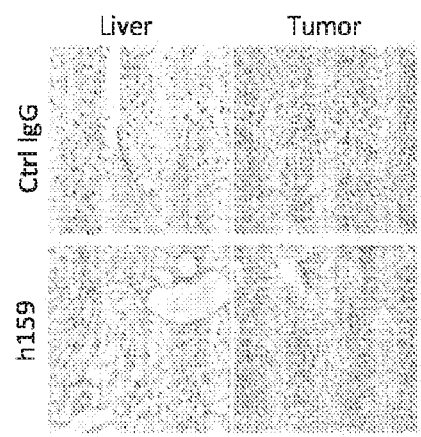
FIG. 3C shows immunohistochemistry analysis performed on the organs shown in FIG. 3B to determine the distribution of humanized MAb159 with a human Fc specific antibody.
Figure 3B:
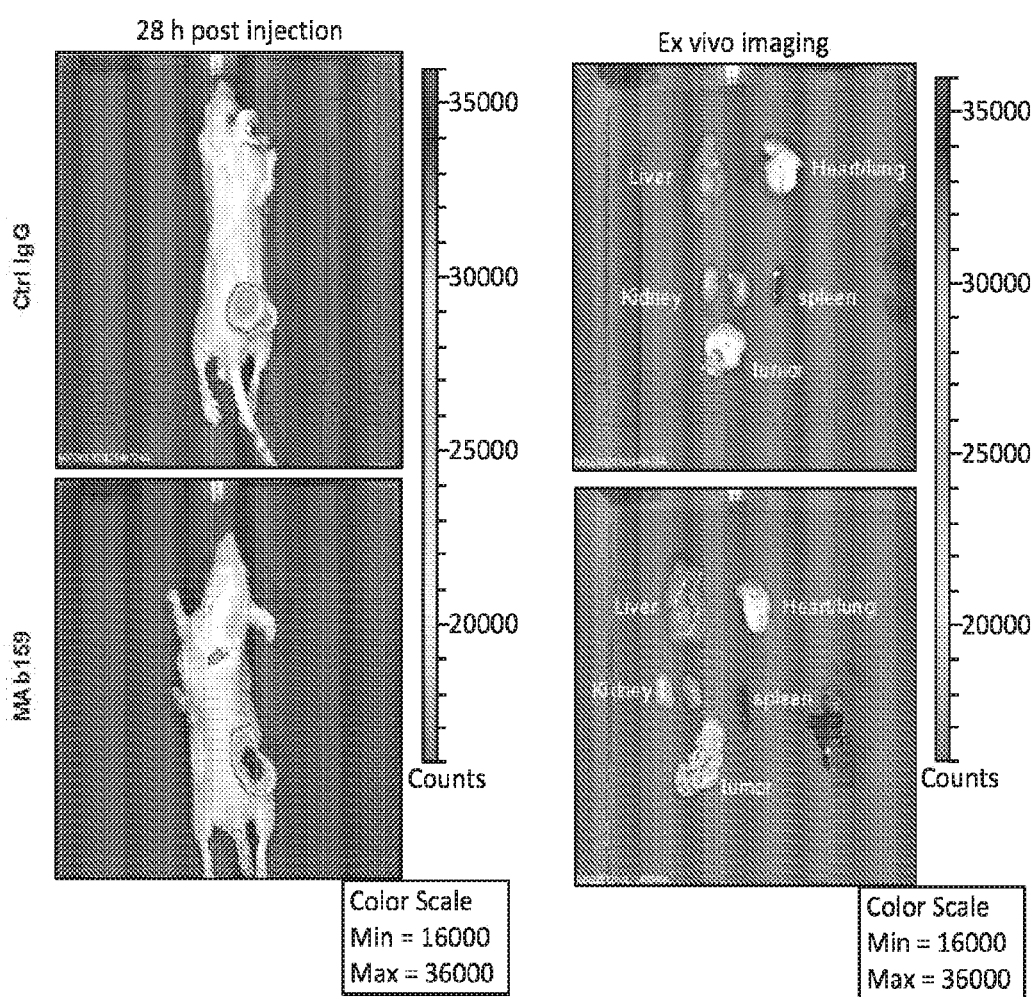
FIG. 3B shows fluorescent whole mouse images of mice that were injected intravenously with 3 mg/kg Cy5.5 conjugated humanized MAb159 or normal human IgG. Images were taken 28 hours after injection (left panel). The mice were subsequently perfused with PBS and formalin, and the organs along with tumors were harvested, and the ex vivo images of the major organs were taken (right panel).

To determine the tumor specific localization of humanized MAb159, we imaged tumor-bearing live mice injected with Cy5.5-labeled humanized Mab 159. For this analysis, xenograft tumors were established as described herein. When the tumor reached about 400 mm³ in volume, the mice (two per group) were put on Teklad Global 1S % Protein Rodent Diet for 3 days and then injected intravenously (i.v.) with 3 mg/kg Cy5.5 labeled antibody (labeled through primary amine). In vivo fluorescence imaging was performed using the Xenogen Lumina XR Imaging System and analyzed using the IVIS Living Imaging 3.0 software (Caliper Life Sciences, Alameda, Calif., USA). A Cy5.5 filter set was used for acquiring the fluorescence of Cy5.5-conjugated antibody. Identical illumination settings (lamp voltage, filters, f/stop, field of views, binning) were used for acquiring all images. Fluorescence emission images were normalized and reported as photons per second per centimeter squared per steradian (p/s/cm2/sr). All near-infrared fluorescence images were acquired using 1 s exposure time (f/stop=4). 28 hours after injection, the mice were perfused with PBS, followed by formalin as described previously (Mitra, Mikolon, et al, 2006). The control IgG used in this study is human IgG purified from normal serum (Rockland). We found that 28 hours after injection, MAb159 preferentially localized to sub-cutaneous H249 tumors but not mouse organs (FIG. 3B, left panel).

At the end of the study, the animals were perfused with PBS followed by formalin, and the organs along with tumors were harvested for an ex vivo imaging with the same settings as the in vivo fluorescence imaging. There was a dramatic difference in the signal intensity in tumor between control IgG and humanized MAb159 (FIG. 3B, right panel). Again, MAb159, but not control IgG, is shown to have specific localization to tumor. The tissues were further subjected to immunohistochemistry analysis using a human Fc specific antibody. For immunohistochemistry, the frozen sections were fixed with 3% formaldehyde for 15 minutes at room temperature, following by two PBS washes. The sections were treated with 3% $H_2O_2$ for 10 min, blocked with goat serum for 1 hour, and incubated with primary antibody for overnight at 4° C. The sections were then washed with PBS and processed with ABC kit (Vector labs, Burlingame, Calif.). The images were obtained with an Olympus BX51 microscope and Image-pro plus 6.0 system. The immunohistochemistry analysis confirmed the specific localization of humanized MAb159, but not control IgG, to tumor (FIG. 3C). Humanized MAb159 is thus shown to specifically localize to tumor, not liver.

EXAMPLE 8

MAb159 Inhibits Various Xenograft Tumor Growths and Tumor Metastasis

The efficacy of MAb159 was further examined in various tumor models. Xenograft tumors were established with human small lung cancer cell H249, non-small cell lung cancer cell A549 and colon cancer cell HT29. Tumors were then treated with 10 mg/kg MAb159 or normal mouse IgG, twice a week. As depicted in FIGS. 4A-4C, MAb159 significantly inhibited tumor progression in both models compared with control (58%, 78% and 50% inhibition, respectively).

To further test if the combination of GRP78 targeted therapy and conventional chemotherapy leads to greater efficacy, we combined MAb159 (10 mg/kg, twice a week) and Irinotecan (18 mg/kg, twice a week) in a colon cancer xenograft model. Colon cancer model was chosen because GRP78 overexpression was reported to be associated with colorectal carcinogenesis (Takahashi, Wang, et al, 2011). As depicted in FIG. 4D, when administrated alone, MAb159 inhibited tumor growth by 54% compared to control group. Irinotecan mono-therapy inhibited tumor growth by 85%. The combination therapy was more effective: it inhibited tumor growth by 95% and caused tumor regression to 47% of the starting tumor volume.

Figure 4E:
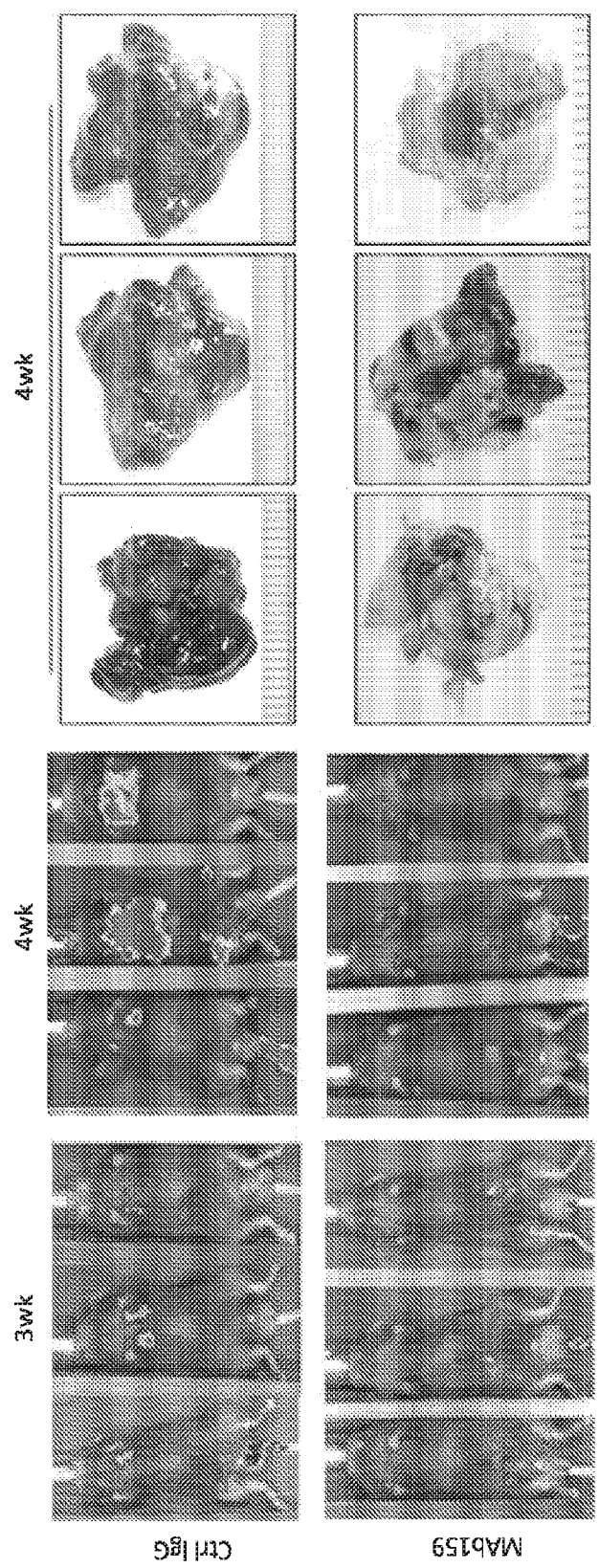
FIG. 4E shows a series of live mouse images showing that treatment using MAb159 (10 mg/kg, twice a week) inhibits the lung metastasis of B16 melanoma cell. Live mouse images taken 3 and 4 weeks after B16 cell injection and Mab159 treatment are shown on the left. The pictures of harvested lungs at the end of the experiment (4 weeks) are shown on the right.

GRP78 also promotes growth of blood vessels in the tumor accompanied by tumor growth and metastasis (Dong et al., Cancer Res., 8:2848-2857, 2011). We thus examined the effect of MAb 159 on the metastatic growth of a syngeneic melanoma cancer cell line. The B 16 lung metastasis model was described previously (Id). Briefly, B16-Fluc-A1 melanoma cells ($5\times10^5$) were injected through the lateral tail vein. The treatment with MAb159 (10 mg/kg, twice a week) started right after the injection of melanoma cells. Lung metastasis was monitored by luminescence imaging (Xenogen) every week starting from week 3. Following sacrifice at week 4, the lungs were removed to visualize the tumors. As depicted in FIG. 4E, left panel, MAb159 treatment significantly reduced the lung tumor formation. Compared to the control group, the lungs from MAb159 treated mice had significantly fewer tumors (FIG. 4E, right panel).

EXAMPLE 9

Figure 5F:
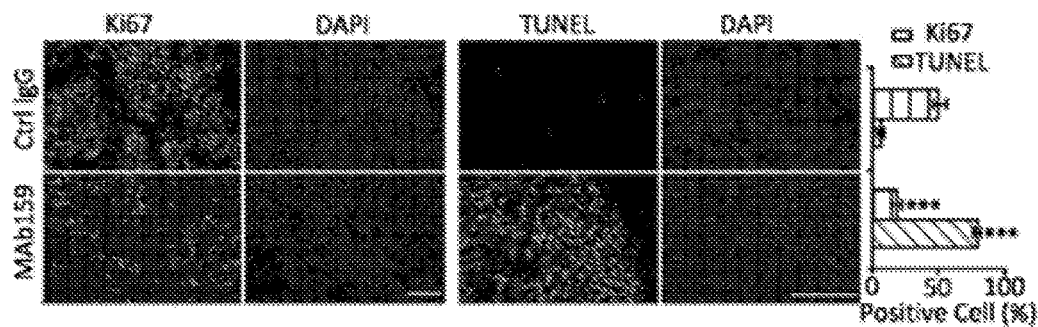
FIGS. 5F-5H are representative immunofluorescence staining pictures of MAb159 treated A549 tumors. MAb159 treatment leads to reduced cell proliferation (Ki67), induced cell apoptosis (TUNEL), impaired vasculature (CD31) and reduced PI3K signaling (phosphorylated S6). Nuclei were counterstained with DAPI (blue).
Figure 5G:
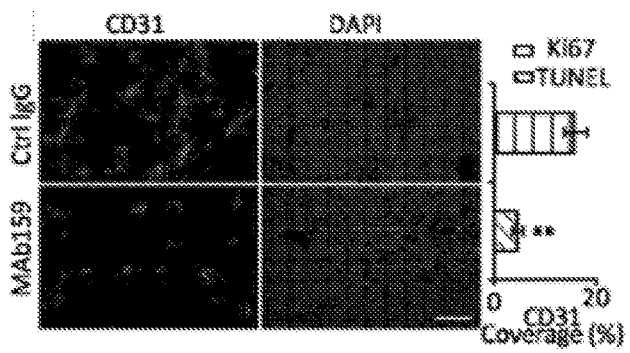
Figure 5H:
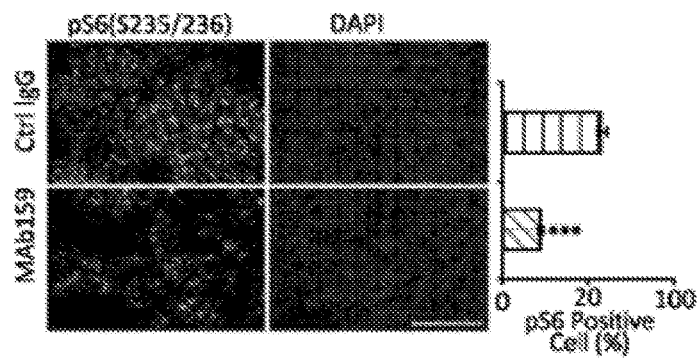
Figure 5I:
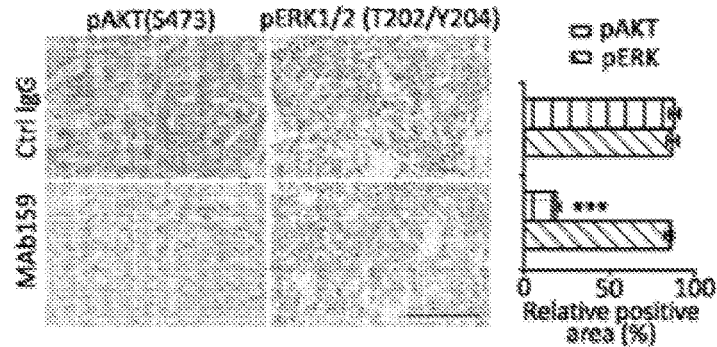
FIG. 5I are representative immunohistochemistry staining pictures of MAb159 treated A549 tumors. MAb159 reduced phosphorylated AKT level, but not phosphorylated MAPK (ERK1/2) level. All quantification data are presented as mean±SEM. Asterisk, double asterisks, and triple asterisks indicate $P<0.05$ and $P<0.02$, and $P<0.001$ respectively, as determined by an unpaired 2-tail student T-test.
Figure 11B:
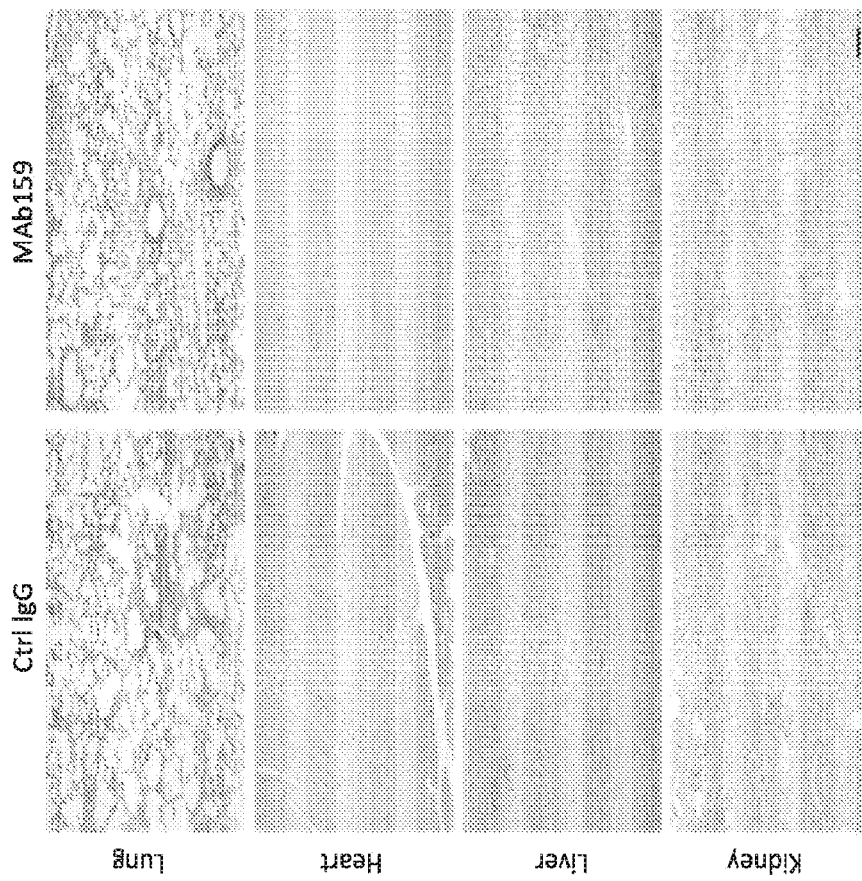
FIG. 11B. H&E staining pictures of the major mice organs in A549 xenograft study shows no apparent toxicity after MAb159 treatment. Scale bar, 100 μm. MAb159 inhibits PI3K signaling in xenograft tumor and shows no toxicity to normal organ.
Figure 11A:
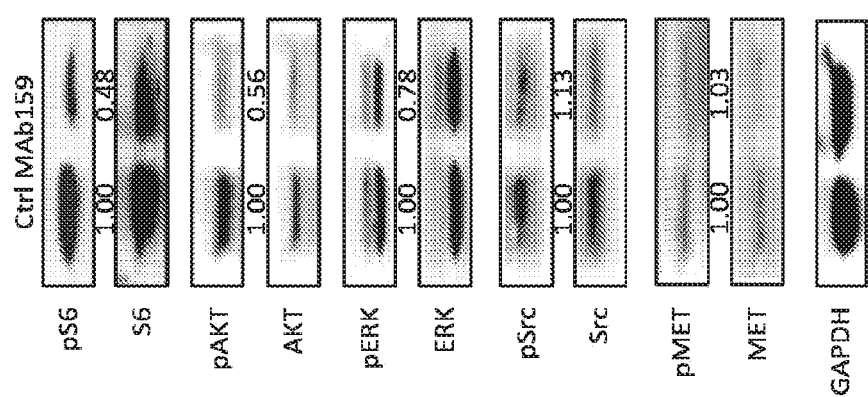
FIG. 11A. The frozen sections of A549 tumors (four tumors from each group) were lysed and combined and the lysates were subjected to Western blotting. Quantification of relative phosphorylated AKT, S6, Erk 1/2, Src, and MET was performed with Odyssey.

MAb159 Reduces Proliferation, Induced Apoptosis, Impairs Tumor Vasculature, and Inhibits PI3K Signaling in Tumor Xenografts At the end of the xenograft experiments, tumors were harvested for analysis. In MAb159 treated group, proliferation index (Ki67 staining) was markedly reduced (FIG. 5F), apoptosis (TUNEL assay) was significantly increased (FIG. 5F), and vessel density (CD31 staining) had a modest decrease (FIG. 5G). MAb159 treatment also led to a marked reduction in phosphorylated S6 and AKT, indicating inhibition of PI3K signaling (FIGS. 5H, 5I and FIG. 11A). However, no significant changes were observed in the level of phosphorylated ERK1/2, c-Met, and Src (FIG. 5G and FIG. 11A) indicating these compensatory pathways often induced with PI3K small molecule inhibitors and responsible for the development of resistance were not altered. In addition it is notable that the systemic administration of the antibody was well tolerated measured by the animal food intake, body weight (data not shown) and microscopic examination of vital organs (FIG. 11B).

EXAMPLE 10

MAb159 is Effective in Suppressing Pten Deletion Induced Leukemogenesis

The studies described above establish that targeting cell surface GRP78 modulates PI3K signaling. We thus tested MAb159 in a constitutive PI3K setting in the Pten knockout spontaneous leukemia model. The Pten (floxed/floxed); Mx-1 cre leukemic model and the protocols for flow cytometry for analysis of leukemic blasts and peripheral blood counts have been described (Wey et al., Blood, 2011). Intraperitoneal administration of polyinosinic-polycytidylic acid (pIpC, 20 μg/gW) was given to 6-8 week old Pten$^{f/f}$; Mxl-Cre mice every other day for a total of 7 doses to induce Cre expression. 10 mg/kg of normal mouse IgG or MAb159 was co-administered with pIpC for these 7 doses. Three days after the last pIpC injection, MAb159 or IgG were administrated for the last time and the mice were analyzed after another three days. As reported previously, inducible knock out of Pten in the hematopoietic system led to development of myeloproliferative disorders and eventual leukemia. As depicted in FIG. 6A, these Pten knockout mice when treated with control IgG had morbid hunched posture, while those treated with MAb159 appeared normal. PTEN deficiency led to significant increase in leukemic blast cells in the bone marrow (BM), as well as increase in spleen weight. As depicted in FIG. 6B, mice treated with MAb159 had a significant reduction in spleen size. As depicted in FIG. 6C, mice treated with MAb159 had restoration of white blood cell, lymphocytes, monocytes, and granulocytes similar to the wild type level in the PTEN deficient mice. The effect on PI3K signaling was measured by the level of phosphorylated AKT with Western blotting (FIG. 6D). Consistent with suppression of AKT activation following inducible heterozygous ablation of Grp78 in the same Pten null model (Id), MAb159 decreased the phosphorylated AKT to normal level in PTEN deficient mice.

EXAMPLE 11

MAb159 Inhibits Tumor Metastasis

Figure 9A:
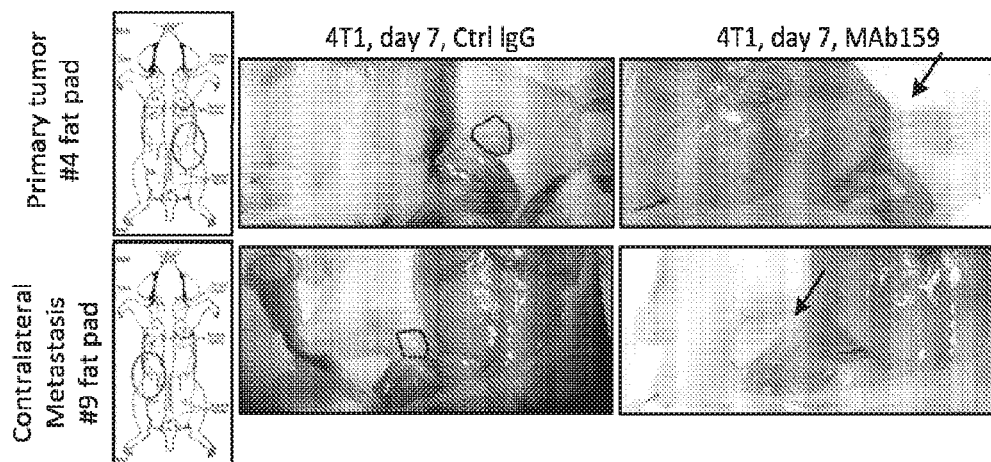
FIG. 9A are pictures of primary 4T1 tumor in fat pad #4 (top) and metastasis in contralateral fat pad #9 (bottom) after 7 days of treatment. Tumor is demarcated by black line and #4 pad is indicated by black arrow.
Figure 9B:
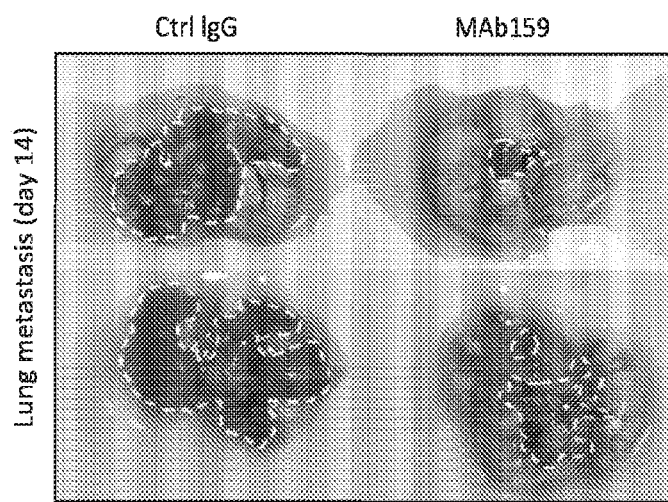
FIG. 9B are representative pictures of lung metastasis in a 4T1 orthotopic breast cancer model. On day 14, MAb159 treatment led to significantly less metastasis compared to control IgG group. Tumor is demarcated by dashed white line.
Figure 10:
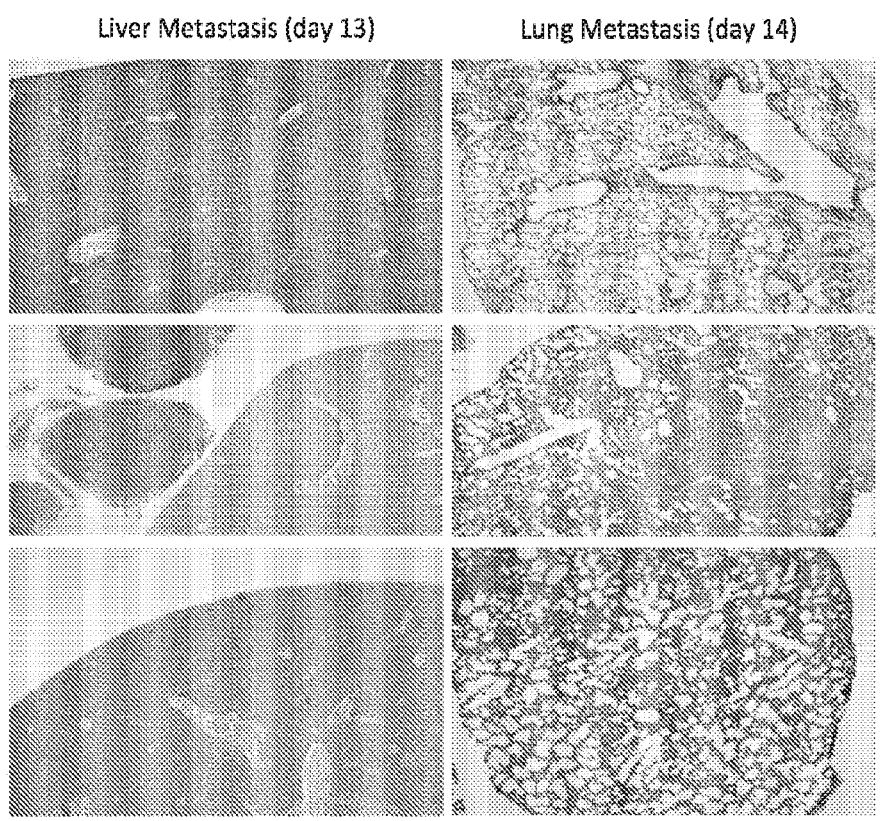
FIG. 10. Histological analysis indicates that MAb159 inhibited lung and liver metastasis in a 4T1 orthotopic breast cancer model. H&E staining pictures of lung and liver from normal mice with no injection of 4T1 cells were shown on top. The middle panels were treated with control IgG, and the bottom panels were treated with MAb159. On day 13, no tumor was seen on the liver of MAb159 treated mice, whereas large tumors were observed on the liver of control group mice (left panel, demarcated with black dotted line). On day 14, large areas of lung were infiltrated with tumor cells in the control group (demarcated with black dotted line), whereas only few tumor cells could be observed in MAb159 treated lungs (right panel).

GRP78 promotes growth of blood vessels in the tumor accompanied by tumor growth and metastasis. As we have shown that cell surface GRP78 is induced in triple negative breast cancer stem-like cells, we tested MAb159 in an orthotopic tumor model using mouse triple negative breast adenocarcinoma cell 4T1. 4T1 cells were implanted into the #4 fat pads of isogenic BALB/c mice, which grew rapidly at the primary site and formed metastases in the contralateral fat pad, lungs, and liver over a period of 2 weeks. Of these mice, half were injected with a bi-weekly dose of MAb159 at 10 mg/kg or saline (control) starting from implantation. After 7 days, MAb159 inhibited primary tumor growth and secondary metastasis to #9 fat pads (FIG. 9A, n=2). After 13 days, several 2-3 mm sized metastatic tumors were present on the livers of control animals (n=3) but not on MAb159-treated mice (n=3). Presence of topical liver metastasis in control animals resulted in focal necrosis of several liver lobes whereas in MAb159-treated animals the liver appeared normal (FIG. 10 left panel and data not shown). The experiment was terminated on day 14. At this stage, in all 3 control mice both primary tumor and #9 fat pad secondary tumors had become large and had invaded through body wall into underlying peritoneal cavity. In comparison, MAb159-treated mice exhibited complete primary tumor regression in 2 out of 3 mice and showed reduced tumor size in the third one. There was no visible contralateral metastasis in any of the MAb159-treated animals. Histological evaluation of lung metastasis showed that the majority of the lung volume of control animals was occupied by metastatic breast cancer that resulted in internal hemorrhaging in 50% of control lungs (FIG. 10 right panel). Lung metastasis was significantly inhibited upon MAb159 treatment (FIG. 9B) and there was no evidence of internal hemorrhaging in any of the M159-treated animals (FIG. 10). Analysis of breast tumor tissues shows that MAb159 significantly reduced pS6 level, suggesting inhibition of PI3K signaling.

We also examined the effect of MAb159 on the metastatic growth of a syngeneic melanoma cancer cell line. B16-Fluc-A1 melanoma cells stably expressing luciferase were injected intravenously. Tumor metastasis and progression in the lungs was monitored live with a whole animal luminescence imaging system. MAb159 treatment significantly reduced the lung tumor formation. At the end of the experiment, lungs were harvested and pigmented tumors were observed on the lung surface. Compared to the control group, the lungs from MAb159 treated mice had significantly fewer tumors.

EXAMPLE 12

Figure 12A:
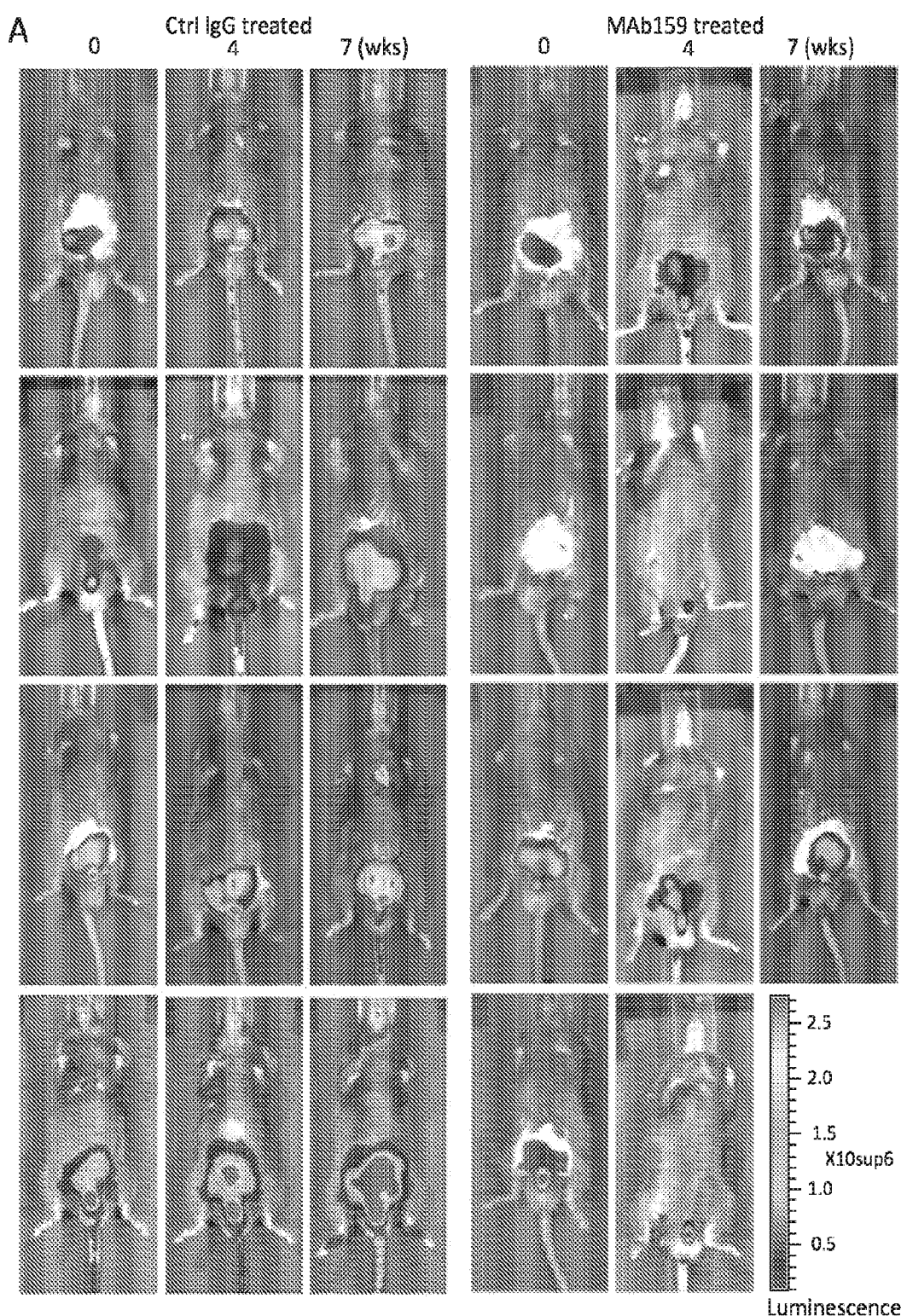
FIG. 12A show live imaging pictures of prostate specific PTEN knockout mice treated with control IgG or MAb159. MAb159 significantly inhibited prostate tumor growth. Same imaging setting was used throughout this study. One MAb159 treated mouse died from anesthesia at week 4.
Figure 12B:
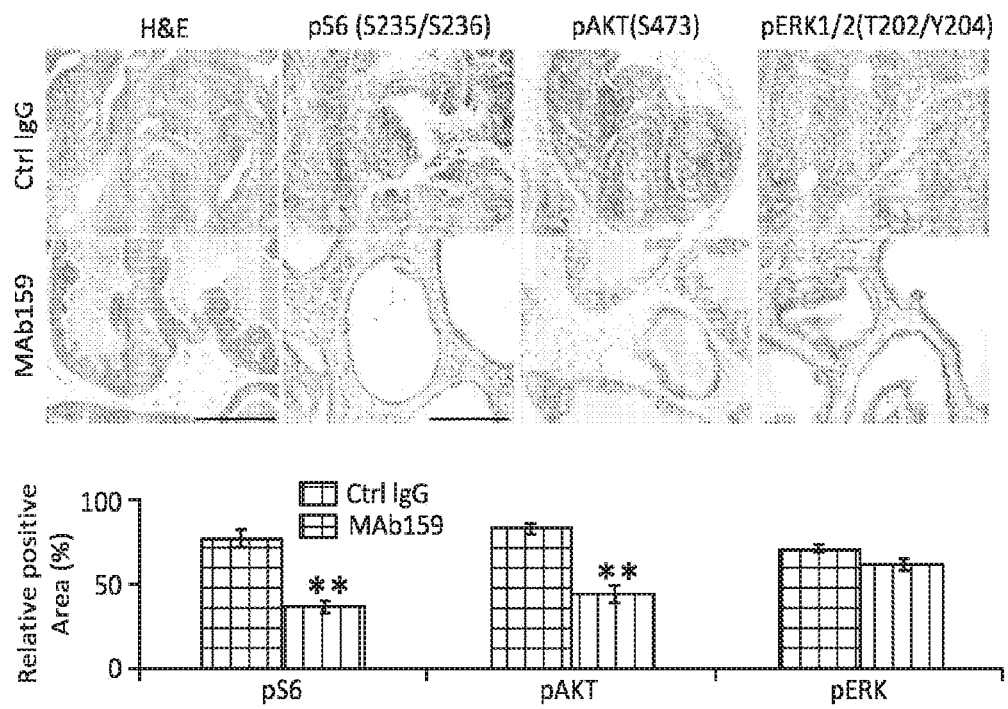
FIG. 12B show hematoxylin and eosin (H&E) stainings of dorsolateral prostate harvested from FIG. 12A are shown on the left. Control IgG treated prostate shows large area of prostatic adenocarcinoma, whereas MAb159 treated prostate only shows mild prostate interepithelial neoplasia. Immunohistochemical stainings of pS6, pAKT, and pERK are shown on the right and corresponding signal quantification is shown below.

MAb159 Suppresses PTEN Deletion Induced Prostate and Uterine Cancer Progression and Leukemogenesis As we have established that targeting cell surface GRP78 modulates PI3K signaling, we tested MAb159 in a constitutive PI3K setting in the PTEN knockout spontaneous tumor models including inducible PTEN knock out in prostate, uterus, and hematopoietic system. In PTEN knockout spontaneous prostate cancer model, PTEN deletion is achieved with induction of Cre under probasin promoter. The luciferase expression is also induced by the same Cre so PTEN deficient prostate cells can be imaged with a luminescence imaging system. Tumor develops in prostate in 2-3 months. Control IgG or MAb159 was given to 2 month old PTEN null mice three times a week at 10 mg/kg dose. Tumor progression was monitored with live animal luminescence imaging. In MAb159 treated group, there was marked tumor regression (FIG. 12A). In contrast, mice in control IgG treated group uniformly progressed. This indicates that MAb159 can cause regression of PTEN deficient prostate cancer. Histological analysis of dorsolateral prostate indicates that control IgG treated prostate had extensive adenocarcinoma (FIG. 12B). In contrast, MAb159 treated prostate only had mild prostate interepithelial neoplasia (FIG. 12B). Further immunohistochemical analysis shows that MAb159 significantly reduced pAKT and pS6 levels, suggesting inhibition of PI3K signaling (FIG. 12B). There was also an insignificant decrease of phosphorylated ERK resulted from MAb159 treatment (FIG. 12B).

Figure 12C:
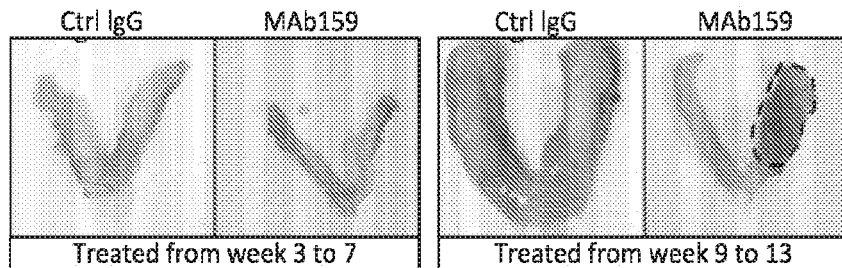
FIG. 12C are representative pictures of uteruses harvested from uterus specific PTEN knockout mice treated with control IgG or MAb159. MAb159 significantly inhibited uterine tumor growth when treatment started from week 3, while it caused uterine tumor regression and necrosis (demarcated with dashed black line) when treatment started from week 9.
Figure 12D:
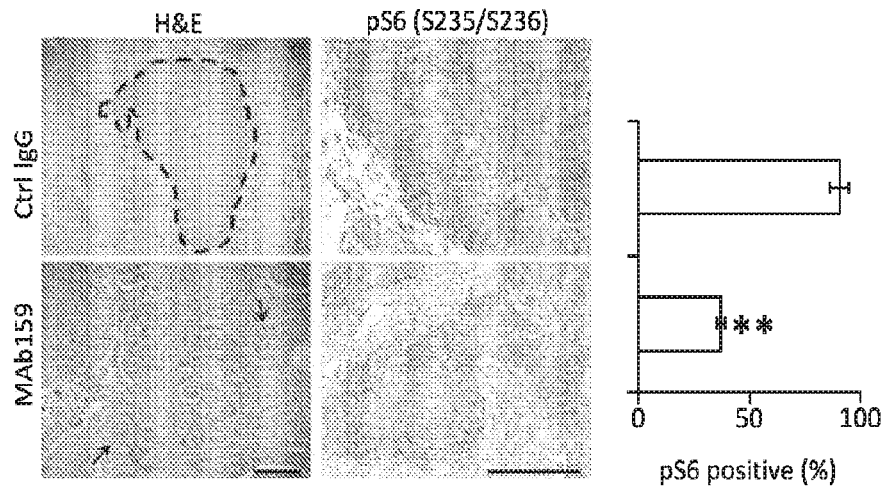
FIG. 12D show H&E staining and immunohistochemical staining of pS6 in uterine tumors harvested from uterus specific PTEN knockout mice treated from week 9 to week 13. In control IgG treated uterus, tumor is large and shows extensive adeno-squamous cancer (demarcated with dashed black line). In contrast, MAb159 treated uterus has normal appearing tissue with only a small island of tumor (indicated by black arrows). Quantification data in FIG. 12B and FIG. 12D are presented as mean±standard error of the mean (SEM) (n=4). Signals were quantified with Image J. Double asterisks indicate P<0.002, as determined by an unpaired 2-tail student T-test. Scale bar, 100 μm.

We also studied the efficacy of MAb159 in a PTEN knockout spontaneous uterine cancer model, in which PTEN deletion is achieved with induction of Cre under progesterone receptor promoter. Mice develop in situ carcinoma as early as ages 3 weeks to 1 month. Control IgG or MAb159 was given to 3 week and 9 week old PTEN null mice three times a week at 20 mg/kg dose for a month. The control IgG treated 3-week mice rapidly developed uterine cancer after one month. In contrast, MAb159 treated 3-week mice had normal uterus (FIG. 12C). As for 9-week mice, MAb159 treatment significantly suppressed the progression of uterine cancer in 9-week mouse and triggered necrosis in uterine tumor (FIG. 12C). Further histological analysis revealed that MAb159 treated uterus had normal appearing tissue with small tumor areas, whereas the control IgG treated uterus had large adeno-squamous tumors (FIG. 12D left panel). This anti-tumor activity of MAb 159 may be through inhibition of PI3K signaling: pS6 level was significantly decreased in MAb159 treated uterus compared to control IgG treated uterus (FIG. 12D).

EXAMPLE 13

Pharmacokinetics and Toxicology Studies of Humanized MAb159

The humanized MAb159 used for this analysis comprised the heavy chain variable region set forth in SEQ ID NO: 21 and the light chain variable region set forth in SEQ ID NO: 23.

A. Pharmacokinetics

A single 10 mg/kg dose of humanized MAb159 was administered i.v. into three C57BL/7 mice and serum samples were collected at 30 min, 4 hours, 1 day, 2 days and 5 days after injection. The serum levels of the antibody were measured with a capture ELISA assay. Briefly, protein A (1 µg/well) was coated on ELISA plate (Thermo Scientific) in PBS overnight at 4° C. Wells were then blocked with 0.5% BSA in PBS, followed by application of serum and 100 ng AP fused GRP78. The bound antibody-antigen complexes were detected with optical reading at 405 nm following application of AP substrate p-Nitrophenyl Phosphate (PNPP). The phalmacokinetics parameters were calculated using a non-compartmental analysis, where Cmax, Tmax, serum half-life and AUC were determined using the trapezoidal rule. This antibody has affinity to GRP78 and efficacy in tumor growth inhibition comparable to the parent murine antibody (data not shown). As depicted in Table 2 below: the mean maximum serum concentration (Cmax) of 61.5 µg/mL was achieved; the mean serum half-life was over 3 days; and an area under curve (AUC) of 4045±1026 µg*hr/mL was achieved.

TABLE 2

| Humanized MAb159 Pharmacokinetics in mouse | |
|---|---|
| Cmax (µg/mL) | 61.5 ± 8.61 |
| Tmax (hours) | 0.5 ± 0 |
| Half-life (hours) | 73.45 ± 9.83 |
| $AUC_{0-120}$ (µg*hr/mL) | 4045.13 ± 1026 |

Cmax, maximum serum concentration; Tmax, time to maximum serum concentration; Half-life, the amount of time it takes for the drug concentration in the blood to decline by half; AUC, area under curve.

B. Toxicology Study

Toxicology study was conducted with C57BL/7 mice, which were injected i.v. twice a week for 5 weeks with PBS, 10 mg/kg humanized MAb159, or 10 mg/kg of an isotype control antibody (n=3). The blood was harvested for Chemistry Panel and Complete Blood Count (CBC) analysis. The major organs (heart, lung, liver, kidney, pancreas, and thymus) were harvested for tissue analysis. At the end of the experiment, animals were anesthetized using isofluorane and euthanized by exsanguination per protocol approved by the University of Southern California IACUC. During necropsy, all animals were subjected to a full gross examination and observations were noted. Blood for hematology and serum chemistry analyses was collected by cardiac puncture from the vena cava. Blood was collected via a single draw and then 0.2-0.5 mL blood was aliquoted into an EDTA tube for hematology and 0.2-0.5 mL blood was placed into a serum separator tube for serum chemistry. Hematology tests included white blood cell count, red blood cell count, platelet count, leukocyte count (basophils, eosinophils, lymphocytes, neutrophils and monocytes), hemoglobin, hematocrit, mean corpuscular hemoglobin (MCH), mean corpuscular hemoglobin concentration (MCHC), mean corpuscular volume (MCV), polychromasia, and blood parasites. Serum chemistry parameters analyzed included albumin, globulin, aspartate transaminase, alanine transaminase, alkaline phosphatase, total bilirubin, blood urea nitrogen, creatinine, phosphorus, calcium, sodium, chloride, cholesterol, and creatinine phosphokinase. Animal spleen, testis, thymus, mesenteric lymph node, pancreas, heart, liver, esophagus, lung, kidney, and bone marrow smears from the femur were collected for histopathology examination. They were fixed immediately using 10% neutral buffered formalin, and were subjected to hematoxylin-eosin staining and microscopic examination. Hematology, serum chemistry and histopathology experiments were performed commercially at Antech Diagnostics (Irvine, Calif.). All results were compiled, analyzed, and statistical analysis was performed using student's T Test and one-way analysis of variance (ANOVA). Overall, there was no significant toxicity found in either the blood or vital organs of humanized MAb159 treated mice (see Table 3 below). The only finding is that there was mild inflammation found in the pancreas of one humanized MAb159 treated mouse, which was also observed in the control antibody treated mice. These results provide good safety and pharmacokinetics data to proceed to human clinical trials.

TABLE 3

Toxicology study of humanized Mab159 in mouse

| Group | CBC | Blood Chemistry Panel | Major Organ Tissue Analysis |
|---|---|---|---|
| PBS | Normal | Normal | Normal |
| Humanized Mab159 | Normal | Normal | Mild neutrophil infiltrate around common pancreatic duct |
| Control IgG | Normal | Normal | Small localized inflammatory lesion in the pancreas |

EXAMPLE 14

Epitope Mapping

GRP78 variants were transiently expressed in 293T cells and the denatured and reduced total whole cell lysates were used for Western blotting with anti-Flag antibody and MAb159. The first and last amino acids are shown for each variant (FIG. 14A). The results of the Western blotting are depicted in FIG. 14B, left and right panel.
Endogenously expressed GRP78 is indicated with black arrows. Based on the results depicted in FIG. 13B, the putative MAb159 epitope is highlighted in the box (FIG. 14C). The underlined residues are the last residue for K633 and T643 variants respectively. A638 is in bold black.

EXAMPLE 15

A MAb159-MMAE Immunoconjugate Causes Cellular Toxicity In Vitro to Cells Expressing Cell Surface GRP78

An immunoconjugate comprising MAb159 and the auristatin derivative MMAE Nere prepared and evaluated as described in the art; see, e.g. Doronina et al, Nature Biotechnology, 2003, 21(7):778-784 (incorporated by reference herein in its entirety for the prnllose of teaching the conjugation and in vitro testing methods). Generally, a protease-cleavable dipeptide linker (Val-Cit) was attached to the N-terminal position of MMAE through a selfimmolative p-aminobenzy lcarbamate spacer. Val-Cit-MMAE has been reported to be stable under physiological conditions but undergoes rapid hydrolysis, leading to the release of MMAE in the presence of lysosomal extracts and human cathepsin B, a tumor-associated lysosomal enzyme. MAb159 was reduced and then alkylated with the maleimido-containing M MAE drug derivative, forming nonaggregated conjugates with about two to four drugs attached per MAb159.

Figure 15:
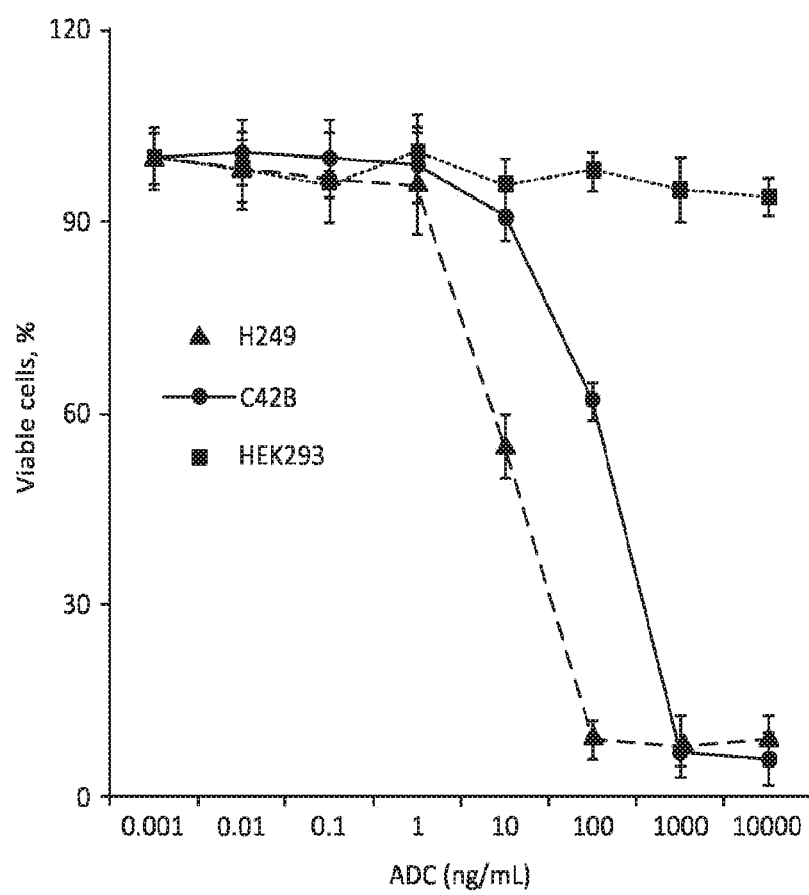
FIG. 15 shows the cytotoxicity of a MAb159-MMAE conjugate in vitro in three different cell lines. The three cell lines were incubated in the presence of MAb159-MMAE and the viability of the cultures was assessed after 3 days using the Alamar Blue assay. Cell lines tested show high GRP78 expression on the cell surface (H249), mid-level GRP78 expression on the cell surface (C42B), or no GRP78 expression on the cell surface (HEK-293). Curves represent dose-dependent cytotoxicity of MAb159-MMAE in the different cell lines. Results are representative of at least two experiments; error bars, SEM.

Three cell lines were incubated in the presence of MAb159-MMAE and the viability of the cultures was assessed after 3 days using the Alamar Blue assay. The cell lines tested show high GRP78 expression on the cell surface (H249), mid-level GRP78 expression on the cell surface (C42B), or no GRP78 expression on the cell surface (HEK-293). As depicted in FIG. 15, MAb159-MMAE retains binding and causes cellular toxicity to cells expressing cell surface GRP78.

The present inventors thus describe herein the generation and selection of monoclonal antibodies (e.g., MAb159) against human GRP78 that have therapeutic potential. For example, we demonstrate that MAb159 specifically binds to GRP78, induces GRP78 endocytosis, and promotes apoptosis. Furthermore, we demonstrate that cell surface GRP78 forms complex with PI3K, and MAb159 can inhibit PI3K/ AKT signaling. In human cancer xenograft models, MAb159 was specifically localized to tumor cell. The tumors treated with MAb159 showed marked reduction in tumor cell proliferation, enhanced tumor cell death, reduced tumor blood vessel density, reduced phosphorylated AKT/ S6 level and without any compensatory upregulation of MAPK signaling. Furthermore, AKT activation and leukemogenesis induced by Pten deletion was blocked by MAb159. In a mouse toxicology study, MAb159 showed no evidence of toxicity to the mice vital organs. This antibody opens up a unique opportunity to study both the biology of cell surface GRP78 and its therapeutic potential.

Another potential application of MAb159 lies in its ability to be used for in vivo imaging. MAb159 specifically recognizes surface GRP78, and thus can be used to image the tumor for personalized medicine and determine whether the amount of surface GRP78 in the tumor predicts disease progression and response to therapy. Clinical trials will incorporate patient imaging as a screening process for inclusion of study subjects. This is particular important in cell surface GRP78 targeted therapy, due to the difficulty in analyzing archival tumor samples with immunostaining since intracellular GRP78 will interfere with such analysis.

Additional Materials and Methods

Antibodies and Other Reagents:

Antibodies against p85 (PI3K regulatory unit, rabbit monoclonal), Akt, phosphorylated Akt (Ser 473), S6, phosphorylated S6, ERK1/2, phosphorylated ERK1/2, Src, phosphorylated Src (Tyr416), GRP78, and phosphorylated GRP78 (Tyr1234/1235) were from Cell Signaling (Danvers, Mass.). Beta-actin and FLAG antibodies were from Sigma (St Louis, Mo.) and GAPDH and p85 (mouse monoclonal) antibody was from Millipore (Temecula, Calif.). Rabbit polyclonal HSP70 antibody was from Santa Cruz (Santa Cruz, Calif.). CD31 antibody was from BD Biosciences (San Jose, Calif.). Ki67 antibody was from Abeam (Cambridge, Mass.). Horse radish peroxidase (HRP) and IRDye conjugated secondary antibodies were from Rockland (Gilbertsville, Pa.).

Cell Culture:

A549, HT29, colo205, LNCap, MCF7, and 293T cell lines were obtained from American Type Culture Collection (Manassas, Va.). C42B cells were kindly provided by Michael Stallcup (USC), and small cell lung carcinoma cells H69, H82, H249, and H345 were kindly provided by Dr. Ravi, Salgia in University of Chicago. The generation of the B 16-Fluc-A1 melanoma cell line has been described ((Dong, Stapleton, et al, 2011). All these cells were propagated in RPMI-1640 supplemented with 10% fetal bovine serum, 100 units/ml of penicillin, and 100 μg/ml streptomycin from Cellgro (Manassas, Va.).

Flow Cytometry:

For adherent cells, cells were washed once with PBS and then dissociated with PBS/0.2% EDTA at 37° C. for about 5 min. After neutralization of EDTA with culture media, cells were centrifuge for 5 min at 1000 rpm. Cells were then washed with cold PBS/0.5% BSA, followed by incubation with 10% normal goat serum for 30 min on ice, and 1 hour with primary antibodies diluted in normal goat serum on ice. Cells were subsequently washed with cold PBS, and incubated with fluorochrome-conjugated secondary antibodies on ice for 30 min. After the final wash with cold PBS, the cell nuclei were stained with DAPI and analyzed with flow cytometer (BD LSR II).

For human blood samples, samples were diluted with 3 volume of PBS and then laid over 2 volume of Ficoll-Paque in a conical tube. The mixture was centrifuged at 400 g for 30 min in a swinging-bucket rotor without brake. The mononuclear cell layer at the inter-phase was carefully transferred to a fresh tube, followed by washing with PBS twice. The pelleted cells were resuspended in PBS/0.5% BSA. The rest of procedure is the same as described above.

For human solid tumor sample, tumor biopsy was mechanically diced using dissecting scissors into small pieces of less than 3 mm in their largest dimension, followed by dGRP78stion with 1 mg/mL collagenase IV (in PBS supplemented with 0.9 mM CaCl$_2$) at 37° C. overnight. Samples were then filtered through a 70 iM nylon cell strainer. The filtrate was centrifuged at 2000 rpm for 5 min, and pelleted cells were resuspended in PBS/0.5% BSA. The rest of procedure is the same as described above.

Morine Tumor Xenograft Models:

HT29, A549, colo205, and CE1 cells were propagated, collected after trypsin dGRP78stion, and resuspended in serum-free medium. Cells ($2 \times 10^6$ were injected subcutaneously bilaterally in the flanks of 8-week-old Balb/C nu/nu mice. Tumor growth was measured 3 times a week and volume was estimated as $0.52 \times a \times b^2$, where a and b are the largest and smallest lengths of the tumor. Once tumors were about 100 mm$^3$ (day 0), animals were distributed into treatment and control groups (n=10 tumors per group) such that the mean tumor volume of each group was comparable and the standard error between groups was minimal. Each group was treated by i.p. injection of antibody two times a week at a dose of 10 mg/kg. At the end of the experiment, mice were sacrificed for tissue analysis. All procedures were approved by Institutional Animal Care and Use Committee and performed in accordance with the Animal Welfare Act regulations.

Surface Protein Biotinylation, Immunoprecipitation and Western Blotting 293T cells growing on 10 cm dish were transfected with Flag tagged GRP78 (without KDEL (SEQ ID NO: 33)) alone or co-transfected with a human EphB2 full length expression vector. 3 days after transfection, cells were rinsed with ice cold PBS twice and incubated with 0.5 mg/rnL EZ-link Sulfo-NHS-LC-Biotin (Thermo scientific) with gentle shake at 4° C. for 30 min. Tris-HCl (pH 7.5) was added to a final concentration of 100 nM to stop the biotinylation reaction. The cells were rinsed with ice cold PBS twice and then lysed with lysis buffer (PBS, 2 mM NaF, 1 mM Na$_3$VO$_4$, 1×protease inhibitor cocktail, and 1% Triton X-100). The biotinylated surface proteins were purified with monomeric avidin-agarose beads (Thermo scientific, Rockford, Ill.) following manufacturer's instructions. The eluted biotinylated proteins were further incubated with beads conjugated with anti-Flag antibody M2 (Sigma, St. Louis, Mo.) at 4° C. overnight to pull down Flag-tagged GRP78. Beads were then washed two times with lysis buffer and the bound proteins were eluted with Laemmli SDS buffer (Bio-Rad, Hercules, Calif.) supplemented with 50 mM dithiothreitol, followed by incubation for 5 min at 95° C. The negative control for IP was beads conjugated with normal mouse IgG from Rockland. In the study to see endogenous interaction of p85 and surface GRP78, before biotin labeling, 293T cells were treated with 300 nM thapsigargin for 16 hours instead. The immunoprecipitation was performed with protein G beads (Genescript, Piscataway, N.J.) and p85, GRP78, and beta-actin antibodies (all mouse IgG 1, 5 µg per reaction). For Western blot, typically 20 µg of whole-cell lysates were run on 4-20% Tris-glycine gradient gel (Biorad, Hercules, Calif.) and transferred onto nitrocellulose membrane (BioRad, Hercules, Calif.). The membrane was blocked with 5% non-fat dry milk in TBS and 0.05% Tween-20 (TBST) for 40 min, and then incubated with 1 µg/ml primary antibody at 4° C. overnight. Membrane was washed three times for 10 min each and incubated with secondary HRP-labeled or IRDye labeled secondary antibody for 40 min. After three times wash with TBST, HRP signal was detected using Femto Maximum Sensitivity chemiluminescent substrate from Thermo Scientific, and IRDye signal was detected by Odyssey (LICOR, Lincoln, Nebr.).

Antibody Endocytosis

MAb159 was biotinylated with EZ-link biotin hydrazide from Thermo Scientific (Rockford, Ill.) following manufacturer's procedure. A549 cells were treated with 10 µg/mL biotinylated MAb159 for 1 hour at 37° C. or at 4° C. The cells were then fixed with 4% paraformaldehyde for 20 min and washed with PBS for 3 times. Cells were permeabilized with 0.1% Triton X-100 and washed with PBS for 3 times. Subsequently cells were stained with streptavidin-FITC (Invitrogen) for 30 min at room temperature. Images were taken with a 100× objective on a Zeiss LSM 510 confocal microscope.

Cell Viability Assay

Cancer cells were seeded in 24-well plates at a density of $2 \times 10^4$ cells/well in a total volume of 500 µL. One day later, the medium was changed to growth medium without glucose. Triplicate wells were treated with 50 µg/mL MAb159 or control mouse IgG (Rockland, Gilbertsville, Pa.). 5 days after treatment, cell viability was assessed using 3-(4,5-dimethylthiazol-2-yl)-2,5-diphenyltetrazolium bromide (MTT) as described previously [35]. Cells were also process for apoptosis analysis with caspase-8/9 colorimetric assay kit (R&D systems, Minneapolis, Minn.) and TdT-mediated dUTP nick-end labeling (TUNEL) assay kit (Promega, Madison, Wis.) following manufacturer's instructions. To examine the effect of MAb159 on primary CLL cells, the cells were isolated as described above and seeded in 96-well plates at a density of $1 \times 10^4$ cells/well in a total volume of 100 µL. Quadruplet wells were treated with MAb159 (20 or 100 µg/mL) or 100 µg/mL normal mouse IgG (Rockland) for 3 days. 10 µL Alamar Blue (Invitrogen, Carlsbad, Calif.) was subsequently added to each well, incubated for 4 hours at 37° C., and fluorescent intensity was measured following manufacturer's instructions.

In Vivo and Ex Vivo Near-Infrared Fluorescence Imaging

When the established xenograft tumors (H249) reached about 400 mm$^3$ in volume, the mice (two per group) were put on Teklad Global 18% Protein Rodent Diet for 3 days and then injected intravenously (i.v.) with 3 mg/kg Cy5.5 labeled antibody (labeled through primary amine). In vivo fluorescence imaging was performed using the Xenogen Lumina XR Imaging System and analyzed using the IVIS Living Imaging 3.0 software (Caliper Life Sciences, Alameda, Calif., USA). A Cy5.5 filter set was used for acquiring the fluorescence of Cy5.5-conjugated antibody. Identical illumination settings (lamp voltage, filters, f/stop, field of views, binning) were used for acquiring all images. Fluorescence emission images were normalized and reported as photons per second per centimeter squared per steradian (p/s/cm2/sr). All near-infrared fluorescence images were acquired using 1 s exposure time (f/stop=4). 28 hours after injection, the mice were perfused with PBS, followed by formalin as described previously [34]. The tumors and organs were then dissected and subjected to ex vivo fluorescence imaging with the same settings as the in vivo fluorescence imaging. The control IgG used in this study is human IgG purified from normal serum (Rockland).

B16 Lung Metastasis Model

The B16 lung metastasis model was described previously [11]. Briefly, B16-Fluc-A1 melanoma cells ($5\times10^5$) were injected through the lateral tail vein. Lung metastasis was monitored by luminescence imaging (Xenogen) every week starting from week 3. The treatment with MAb159 (10 mg/kg, twice a week) started right after the injection of melanoma cells. Following sacrifice at week 4, the lungs were removed to visualize the tumors. Normal mouse IgG (Rockland) was used as control. There were 4 mice in each group.

Orthotopic 4T1 Breast Cancer Model

A total of $6.3\times10^5$ 4T1 cells in 10 µL was injected into the #4 mammary fat pad using Hamilton microsyringe and custom 29 gauge removable needles (Hamilton Catalog #7653-01 and 7803-06 RN/29GA/0.5"/12 degrees). Mouse nipples served as positional cues for fat pad location. Antibody MAb 159 or control normal mouse IgG was administered at 10 mg/kg twice weekly by intra-peritoneal injection and mouse body weight and body condition were monitored to assess metastatic burden and euthanasia end points. The first does was given 30 minutes after 4T1 cell injection. Metastasis in contralateral #9 fat pad, lung, and liver was determined upon terminal necropsy on days 7, 13 and 14 after orthotopic injections. Upon surgical incision, the dermis was separated from the body wall and pinned back to reveal the mammary fat pads. Primary tumor and metastatic mammary fat pads and other organs with visible metastasis were fixed in 10% neutral buffered formalin for 24 hours followed by reconstitution in 30% sucrose at 4° C. These organs were embedded in paraffin and 7.5 micron sections were obtained using Leica RM2235 ultra-microtome.

To determine maximum tumor size in mouse fat pads and to evaluate metastasis at different depths of organ tissue, step-cuts were generated through the entire specimen. 7.5 µm sections were generated at intervals of 150 µm into the specimen and 3-4 slides at multiple depths were analyzed by hematoxylin-eosin staining. Slides were deparraffinized by sequential incubation in xylene (3 min), xylene (3 min), 100% ethanol (1 min), 90% ethanol (1 min), 80% ethanol (1 min) and 75% ethanol (1 min), followed by de-ionized water rinses. Slides were stained for 4 min in CAT Hematoxylin (Biocare Medical) to allow penetration in fatty tissue such as mammary fat pads and de-stained for 1 min using 0.3% acid alcohol. Eosin Y (Fisher Scientific) staining was performed for 3 hours to allow stain penetration into fatty tissue. H&E stained slides were evaluated by microscopy and 4× pictures were taken at the depth where the tumor's diameter was maximum to allow for an accurate comparison. Similarly for evaluation of lung and liver, metastatic burden at multiple depths was evaluated and representative 4× pictures were depicted.

Immunofluorescence and Immunohistochemistry

For immunofluorescence, fresh frozen tissue embedded in OCT was sectioned at 5 µm and fixed in phosphate-buffered 4% paraformaldehyde and washed in PBS. Sections were then blocked with goat serum and incubated with primary antibody overnight at 4° C. After washing in PBS, antibody binding was localized with AlexaFluor conjugated appropriate secondary antibodies (Invitrogen, Carlsbad, Calif.). Nuclei were counterstained with 6-diamidino-2-phenylindole dihydrochloride hydrate (DAPI). Images were obtained with a Nikon Eclipse 80i fluorescence microscope and Meta Morph imaging series system.

For immunohistochemistry, the frozen sections were fixed with 3% formaldehyde for 15 minutes at room temperature, following by two PBS washes. The sections were treated with 3% H202 for 10 min, blocked with goat serum for 1 hour, and incubated with primary antibody for overnight at 4° C. The sections were then washed with PBS and processed with ABC kit (Vector labs, Burlingame, Calif.). The images were obtained with an Olympus BX51 microscope and Image-pro plus 6.0 system.

Four representative pictures were taken for each sample and quantification was performed with Image J (NIH). P value was determined by an unpaired 2-tail student T-test.

Pharmacokinetics

A single 10 mg/kg dose of humanized MAb159 was administered i.v. into three C57BL/7 mice and serum samples were collected at 30 min, 4 hours, 1 day, 2 days and 5 days after injection. The serum levels of the antibody were measured with a capture ELISA assay. Briefly, protein A (1 µg/well) was coated on ELISA plate (Thermo Scientific) in PBS overnight at 4° C. Wells were then blocked with 0.5% BSA in PBS, followed by application of serum and 100 ng AP fused GRP78. The bound antibody-antigen complexes were detected with optical reading at 405 nm following application of AP substrate p-Nitrophenyl Phosphate (PNPP). The pharmacokinetics parameters were calculated using a non-compartmental analysis, where $C_{max}$, $T_{max}$, serum half-life and AUC were determined using the trapezoidal rule.

Toxicology Study

Toxicology study was conducted with C57BL/7 mice, which were injected i.v. twice a week for 5 weeks with PBS, 10 mg/kg humanized MAb159, or 10 mg/kg of an isotype control antibody (n=3). The blood was harvested for Chemistry Panel and Complete Blood Count analysis. The major organs (heart, lung, liver, kidney, pancreas, and thymus) were harvested for tissue analysis. At the end of the experiment, animals were anesthetized using isofluorane and euthanized by exsanguination per protocol approved by the University of Southern California IACUC. During necropsy, all animals were subjected to a full gross examination and observations were noted. Blood for hematology and serum chemistry analyses was collected by cardiac puncture from the vena cava. Blood was collected via a single draw and then 0.2-0.5 mL blood was aliquoted into an EDTA tube for hematology and 0.2-0.5 mL blood was placed into a serum separator tube for serum chemistry. Hematology tests included white blood cell count, red blood cell count, platelet count, leukocyte count (basophils, eosinophils, lymphocytes, neutrophils and monocytes), hemoglobin, hematocrit, mean corpuscular hemoglobin (MCH), mean corpuscular hemoglobin concentration (MCHC), mean corpuscular volume (MCV), polychromasia, and blood parasites. Serum chemistry parameters analyzed included albumin, globulin, aspartate transaminase, alanine transaminase, alkaline phosphatase, total bilirubin, blood urea nitrogen, creatinine, phosphorus, calcium, sodium, chloride, cholesterol, and creatinine phosphokinase. Animal spleen, testis, thymus, mesenteric lymph node, pancreas, heart, liver, esophagus, lung, kidney, and bone marrow smears from the femur were collected for histopathology examination. They were fixed immediately using 10% neutral buffered formalin, and were subjected to hematoxylin-eosin staining and microscopic examination. Hematology, serum chemistry and histopathology experiments were performed commercially at Antech Diagnostics (Irvine, Calif.). All results were compiled, analyzed, and statistical analysis was performed using student's T Test and one-way analysis of variance (ANOVA).

All of the articles and methods disclosed and claimed herein can be made and executed without undue experimentation in light of the present disclosure. While the articles and methods of this invention have been described in terms of preferred embodiments, it will be apparent to those of skill in the art that variations may be applied to the articles and methods without departing from the spirit and scope of the invention. All such variations and equivalents apparent to those skilled in the mi, whether now existing or later developed, are deemed to be within the spirit and scope of the invention as defined by the appended claims. All patents, patent applications, and publications mentioned in the specification are indicative of the levels of those of ordinary skill in the art to which the invention pertains. All patents, patent applications, and publications are herein incorporated by reference in their entirety for all purposes and to the same extent as if each individual publication was specifically and individually indicated to be incorporated by reference in its entirety for any and all purposes. The invention illustratively described herein suitably may be practiced in the absence of any element(s) not specifically disclosed herein. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Sequence Listings

The nucleic and amino acid sequences listed in the accompanying sequence listing are shown using standard letter abbreviations for nucleotide bases and three letter code for amino acids, as defined in 37 C.F.R. 1.822.

SEQ ID NO: 1 is the amino acid sequence of a human cell surface GRP78 polypeptide. The coding sequence is amino acids residues 1-650. Amino acid residues 651-654 represent a C-terminal peptide.

SEQ ID NO: 2 is a nucleic acid sequence encoding a human cell surface GRP78 polypeptide. The coding sequence is nucleic acids 1-1950.

SEQ ID NO: 3 is the amino acid sequence of a heavy chain $CDR_1$ in an antibody which specifically binds cell surface GRP78.

SEQ ID NO: 4 is the amino acid sequence of a heavy chain $CDR_2$ in an antibody which specifically binds cell surface GRP78.

SEQ ID NO: 5 is the amino acid sequence of a heavy chain $CDR_3$ in an antibody which specifically binds cell surface GRP78.

SEQ ID NO: 6 is the amino acid sequence of a light chain $CDR_1$ in an antibody which specifically binds cell surface GRP78.

SEQ ID NO: 7 is the amino acid sequence of a light chain $CDR_2$ in an antibody which specifically binds cell surface GRP78.

SEQ ID NO: 8 is the amino acid sequence of a light chain $CDR_3$ in an antibody which specifically binds cell surface GRP78.

SEQ ID NO: 9 is the amino acid sequence of a heavy chain variable region of a murine antibody which specifically binds cell surface GRP78.

SEQ ID NO: 10 is a nucleic acid sequence encoding a heavy chain variable region of a murine antibody which specifically binds cell surface GRP78.

SEQ ID NO: 11 is the amino acid sequence of a light chain variable region of a murine antibody which specifically binds cell surface GRP78.

SEQ ID NO: 12 is a nucleic acid sequence encoding a light chain variable region of a murine antibody which specifically binds cell surface GRP78.

SEQ ID NO: 13 is the amino acid sequence of a heavy chain variable region of a humanized antibody which specifically binds cell surface GRP78.

SEQ ID NO: 14 is a nucleic acid sequence encoding a heavy chain variable region of a humanized antibody which specifically binds cell surface GRP78.

SEQ ID NO: 15 is the amino acid sequence of a heavy chain variable region of a humanized antibody which specifically binds cell surface GRP78.

SEQ ID NO: 16 is a nucleic acid sequence encoding a heavy chain variable region of a humanized antibody which specifically binds cell surface GRP78.

SEQ ID NO: 17 is the amino acid sequence of a heavy chain variable region of a humanized antibody which specifically binds cell surface GRP78.

SEQ ID NO: 18 is a nucleic acid sequence encoding a heavy chain variable region of a humanized antibody which specifically binds cell surface GRP78.

SEQ ID NO: 19 is the amino acid sequence of a heavy chain variable region of a humanized antibody which specifically binds cell surface GRP78.

SEQ ID NO: 20 is a nucleic acid sequence encoding a heavy chain variable region of a humanized antibody which specifically binds cell surface GRP78.

SEQ ID NO: 21 is the amino acid sequence of a heavy chain variable region of a humanized antibody which specifically binds cell surface GRP78.

SEQ ID NO: 22 is a nucleic acid sequence encoding a heavy chain variable region of a humanized antibody which specifically binds cell surface GRP78.

SEQ ID NO: 23 is the amino acid sequence of a light chain variable region of a humanized antibody which specifically binds cell surface GRP78.

SEQ ID NO: 24 is a nucleic acid sequence encoding a light chain variable region of a humanized antibody which specifically binds cell surface GRP78.

SEQ ID NO: 25 is the amino acid sequence of a light chain variable region of a humanized antibody which specifically binds cell surface GRP78.

SEQ ID NO: 26 is a nucleic acid sequence encoding a light chain variable region of a humanized antibody which specifically binds cell surface GRP78.

SEQ ID NO: 27 is the amino acid sequence of a light chain variable region of a humanized antibody which specifically binds cell surface GRP78.

SEQ ID NO: 28 is a nucleic acid sequence encoding a light chain variable region of a humanized antibody which specifically binds cell surface GRP78.

SEQ ID NO: 29 is the amino acid sequence of a light chain variable region of a humanized antibody which specifically binds cell surface GRP78.

SEQ ID NO: 30 is a nucleic acid sequence encoding a light chain variable region of a humanized antibody which specifically binds cell surface GRP78.

SEQ ID NO: 31 is the amino acid sequence of an epitope comprising amino acid residues 608 to 637 of SEQ ID NO: 1, to which the antibodies and antigen-binding fragments of the present invention bind.

SEQ ID NO: 32 is the amino acid sequence of an epitope comprising amino acid residues 623 to 637 of SEQ ID NO: 1, to which the antibodies and antigen-binding fragments of the present invention bind.

SEQUENCE LISTINGS

SEQ ID NO: 1 - GRP78 amino acid sequence
MKLSLVAAMLLLLSAARAEEEDKKEDVGTVVGIDLGTTYSCVGVFKNGRVEIIA
NDQGNRITPSYVAFTPEGERLIGDAAKNQLTSNPENTVFDAKRLIGRTWNDPS
VQQDIKFLPFKVVEKKTKPYIQVDIGGGQTKTFAPEEISAMVLTKNIKETAEA
YLGKKVTHAVVTVPAYFNDAQRQATKDAGTIAGLNVMRIINEPTAAAIAYG
LDKREGEKNILVFDLGGGTFDVSLLTIDNGVFEVVATNGDTHLGGEDFDQRV
MEHFIKLYKKKTGKDVRKDNRAVQKLRREVEKAKRALSSQHQARIEIESFYE
GEDFSETLTRAKFEELNMDLFRSTMKPVQKVLEDSDLKKSDIDEIVLVGGSTRI
PKIQQLVKEFFNGKEPSRGINPDEAVAYGAAVQAGVLSGDQDTGDLVLLDVCPL
TLGIETVGGVMTKLIPRNTVVPTKKSQIFSTASDNQPTVTIKVYEGERPLTKDN
HLLGTFDLTGIPPAPRGVPQIEVTFEIDVNGILRVTAEDKGTGNKNKITITNDQ
NRLTPEEIERMVNDAEKFAEEDKKLKERIDTRNELESYAYSLKNQIGDKEKLGGK
LSSEDKETMEKAVEEKIEWLESHQDADIEDFKAKKKELEEIVQPIISKLYGSAGPP
PTGEEDTAEKDEL SEQ ID NO: 2 - GRP78 nucleic acid sequence
atgaagctctccctggtggccgcgatgctgctgctgctcagcgcggcgcgggccgaggaggaggacaagaagga
ggacgtgggcacggtggtcggcatcgacctggggaccacctactcctgcgtcggcgtgttcaagaacggccgcgtgga
gatcatcgccaacgatcagggcaaccgcatcacgccgtcctatgtcgccttcactcctgaagggaacgtctgattggcg
atgccgeeaagaaccagctcacctccaaccccgagaacacggtctttgacgccaagcggctcatcggccgcacgtgga
atgacccgtctgtgcagcaggacatcaagttcttgccgttcaaggtggttgaaaagaaaactaaaccatacattcaagtt
gatattggaggtgggcaaacaaagacatttgctcctgaagaaatttctgccatggttctcactaaaatgaaagaaaccg
ctgaggcttatttgggaaagaaggttacccatgcagttgttactgtaccagcctatttaatgatgcccaacgccaagca
accaaagacgctggaactattgctggcctaaatgttatgaggatcatcaacgagcctacggcagctgctattgcttatg
gcctggataagaggggaggggggaagaacatcctggtgtttgacctgggtggcggaaccttcgatgtgtctcttctca
ccattgacaatggtgtcttcgaagttgtggccactaatggagatactcatctgggtggagaagactttgaccagcgtgt
catgaacacttcatcaaactgtacaaaagaagacgggcaaagatgtcaggaagacaatagagctgtgcagaaa
ctccggcgcgaggtagaaaaggccaaacgggccctgtcttcttcagcatcaagcaagaattgaaattgagtccttctat
gaaggagaagacttttctgagaccctgactcgggccaaatttgaagagctcaacatggatctgttccggtctactatga
agcccgtccagaaagtgttggaagattctgatttgaagaagtctgatattgatgaaattgttcttgttggtggctcgactc
gaattccaaagattcagcaactggttaaagagttcttcaatggcaaggaaccatcccgtggcataaaccagatgaag
ctgtagcgtatggtgctgctgtccaggctggtgtgctctctggtgatcaagatacaggtgacctggtactgcttgatgta
tgtccccttacacttggtattgaaactgtgggaggtgtcatgaccaaacacagtggtgcctacca
agaagtctcagatcttttctacagcttctgataatcaaccaactgttacaatcaaggtctatgaaggtgaaagacccctg
acaaaagacaatcatctctgggtacatttgatctgactggaattcctcctgctcctcgtgggtcccacagattgaagt
cacctttgagatagatgtgaatggtattcttcgagtgacagctgaagacaagggtacagggaacaaaaataagatcac
aatcaccaatgaccagaatcgcctgacacctgaagaaatcgaaaggatggttaatgatgctgagaagtttgctgagg
aagacaaaaagctcaaggagcgcattgatactagaaatgagttggaaagctatgcctattctctaaagaatcagattgg
gagataaagaaaagctggaggtaaactttcctctgaagataaggagaccatggaaaaagctgtagaagaaaagatt
gaatggctgaaagccaccaagatgctgacattgaagacttcaaagctaagaagaaggaactggaagaaattgttca
accaattatcagcaaactctatggaagtgcaggccctcccccaactggtgaagaggatacagcagaaaaagatgagt
tgtag SEQ ID NO: 3 - Murine MAb159 heavy chain CDR1 amino acid sequence
SYWMH SEQ ID NO: 4 - Murine MAb159 heavy chain CDR2 amino acid sequence
EINPGNGRTNYNEKFKR SEQ ID NO: 5 - Murine MAb159 heavy chain CDR3 amino acid sequence
LYYYDGTYDY SEQ ID NO: 6 - Murine MAb159 light chain CDR1 amino acid sequence
KASQNVGTDVA SEQ ID NO: 7 - Murine MAb159 light chain CDR2 amino acid sequence
WASNRFT SEQ ID NO: 8 - Murine MAb159 light chain CDR3 amino acid sequence
QQYSSSPWT SEQ ID NO: 9 - Murine MAb159 heavy chain variable region amino acid sequence
QAQLQQPGAELVKPGASVRLSCKASGYTFFSYWMHWVKQRPGQGLEWI
GEINPGNGRTNYNEKFKRKATLTVDKSSSTAYMQLNSLTSEDSAVYYCA
TLYYYDGTYDYWGQGTTLTVSS SEQ ID NO: 10 - Murine MAb159 heavy chain variable region nucleic acid sequence
caggcccaactgcagcagcctggggctgaactggtgaagcctggggcttcagtgaggctgtcctgcaaggcttctg
gttacaccttcaccagctactggatgcactgggtgaagcagaggcctggacaaggccttgagtggattggagagatt
aatcctggcaacggtcgtactaactacaatgagaagttcaagagaaaggccacactgactgtagacaaatcctccag
cacagcctacatgcaactcaacagcctgacatctgaggactctgcggtctattactgtgcaacccttttattactacgatg
gtacttacgactactggggccaaggcaccactctcacagtctcctca SEQ ID NO: 11 - Murine MAb159 light chain variable region amino acid sequence
DIVMTQSHKFMSTSVGDRVSVTCKASQNVGTDVAWYQQKPGQSPKALIY
WASNRFTGVPDRFTGSGSGTDFTLTINNVQSEDLVDYFCQQYSSSPWTFG
GGTKLEIK

SEQUENCE LISTINGS

SEQ ID NO: 12 - Murine MAb159 light chain variable region amino acid sequence
gacattgtgatgacccagtctcacaaattcatgtccacatcagtaggagacaggtcagcgtcacctgcaaggccagt
cagaatgtgggtactgatgtagcctggtatcaacagaaaccagggcaatctcctaaagcactgatttactgggcatcc
aaccggttcactggagtccctgatcgcttcacaggcagtggatctgggacagatttcactctcaccattaacaatgtgc
agtctgaagacttagtagattatttctgtcagcaatatagcagctctccgtggacgttcggtggaggcaccaagctgga
aatcaaa SEQ ID NO: 13 - Humanized heavy chain variable region amino acid sequence
QAQLVQSGAELKKPGASVKLSCKASGYTFTSYWMHWVKQAPGQGLEWI
GEINPGNGRTNYNEKFKRRATLTVDKSASTAYMELSSLRSEDSA
VYYCATLYYYDGTYDYWGQGTTVTVSS SEQ ID NO: 14 - Humanized heavy chain variable region nucleic acid sequence
caggcccagctggtgcagtctggcgeegagctgaagaaacctggcgcctccgtgaagctgtcctgcaaggcctcc
ggctacaccttcaccagctactggatgcactgggtgaaacaggcccaggccagggactggaatggatcggcgag
atcaaccccggcaacgccggaccaactacaacgagaagttcaagcggagagccaccctgaccgtggacaagtc
cgcctccaccgcctacatggaactgtcctccctgcggagcgaggactccggegtgtactactgcgccaccctgtactac
tacgacggcacctacgactactggggccagggcaccaccgtgaccgtgtctagc SEQ ID NO: 15 - Humanized heavy chain variable region amino acid sequence
QAQLVQSGAEVKKPGASVKLSCKASGYTFTSYWMHWVKQAPGQGLEWI
GEINPGNGRTNYNEKFKRRATLTVDKSASTAYMELSSLRSEDTAVYYCAT
LYYYDGTYDYWGQGTTVTVSS SEQ ID NO: 16 - Humanized heavy chain variable region nucleic acid sequence
caggcccagctggtgcagtctggcgeegaggtgaagaaacctggcgcctccgtgaagctgtcctgcaaggcctcc
ggctacaccttcaccagctactggatgcactgggtgaaacaggcccaggccagggactggaatggatcggcgag
atcaaccccggcaacggccggaccaactacaacgagaagttcaagcggagagccaccctgaccgtggacaagtc
cgcctccaccgcctacatggaactgtcctccctgcggagcgaggacaccggegtgtactactgcgccaccctgtac
tactacgacggcacctacgactactggggccagggcaccaccgtgaccgtgtctagc SEQ ID NO: 17 - Humanized heavy chain variable region amino acid sequence
QAQLVQSGAEVKKPGASVKLSCKASGYTFTSYWMHWVRQAPGQGLEWI
GENPGNGRTNYNEKFKRRATLTVDKSASTAYMELSSLRSEDTAVYYCAT
LYYYDGTYDYWGQGTTVTVSS SEQ ID NO: 18 - Humanized heavy chain variable region nucleic acid sequence
caggcccagctggtgcagtctggcgeegaggtgaagaaacctggcgcctccgtgaagctgtcctgcaaggcctcc
ggctacaccttcaccagctactggatgcactgggtgcggcaggccccaggccagggactggaatggatcggcgag
atcaaccccggcaacgccggaccaactacaacgagaagttcaagcggagagccaccctgaccgtggacaagtc
cgcctccaccgcctacatggaactgtcctccctgcggagcgaggacaccggegtgtactactgcgccaccctgtac
tactacgacggcacctacgactactggggccagggcaccaccgtgaccgtgtctagc SEQ ID NO: 19 - Humanized heavy chain variable region amino acid sequence
QAQLVQSGAEVKKPGASVKVSCKASGYTFTSYWMHWVRQAPGQGLEWI
GEINPGNGRTNYNEKFKRRATITVDKSASTAYMELSSLRSEDTAVYYCAT
LYYYDGTYDYWGQGTTVTVSS SEQ ID NO: 20 - Humanized heavy chain variable region nucleic acid sequence
caggcccagctggtgcagtctggcgccgaggtgaagaaacctggcgcctccgtgaaggtgtcctgcaaggcctcc
ggctacaccttcaccagctactggatgcactgggtgcggcaggccccaggccagggactggaatggatcggcgag
atcaaccccggcaacgccggaccaactacaacgagaagttcaagcggagagccaccatcaccgtggacaagtc
cgcctccaccgcctacatggaactgtcctccctgcggagcgaggacaccgccgtgtactactgcgccaccctgtact
actacgacggcacctacgactactggggccagggcaccaccgtgaccgtgtctagc SEQ ID NO: 21 - Humanized heavy chain variable region amino acid sequence
QAQLVQSGAEVKKPGASVKVSCKASGYTFTSYWMHWVRQAPGQGLEWI
GEINPGNGRTNYNEKFKRRVTITVDKSASTAYMELSSLRSEDTAVYYCAT
LYYYDGTYDYWGQGTTVTVSS SEQ ID NO: 22 - Humanized heavy chain variable region nucleic acid sequence
caggcccagctggtgcagtctggcgccgaggtgaagaaacctggcgcctccgtgaaggtgtcctgcaaggcctcc
ggctaaccttcaccagctactggatgcactgggtgcggcaggccccaggccagggactggaatggatcggcgaga
tcaaccccggcaacggccggaccaactacaacgagaagttcaagcggagagtgaccatcaccgtggacaagtcc
gcctccaccgcctacatggaactgtcctccctgcggagcgaggacaccggegtgtactactgcgccaccctgtactact
acgacggcacctacgactactggggccagggcaccaccgtgaccgtgtctagc SEQ ID NO: 23 - Humanized light chain variable region amino acid sequence
DIVMTQSPSFLSASVGDRVTITCKASQNVGTDVAWYQQKPGKAPKALIY
WASNRFTGVPDRFTGSGSGTDFTLTISSLQSEDVADYFCQQYSSSPWTFG
GGTKVEIK SEQ ID NO: 24 - Humanized light chain variable region nucleic acid sequence
gacatcgtgatgacccagtcccccagcttcctgtccgcctccgtgggcgacagagtgaccatcacatgcaaggcctccca
gaacgtgggcaccgacgtggcctggtatcagcagaagcccggcaaggcccccaaggccctgatctactgggcctccaaccg -continued

SEQUENCE LISTINGS

```
gttcaccggcgtgcccgacagattcaccggctctggctccggcaccgacttcaccctgaccatctccagcctgcagtccgagg
acgtggccgactacttctgccagcagtactcctccagcccctggaccttcggcggaggcaccaaggtggaaatcaag
```

SEQ ID NO: 25 - Humanized light chain variable region amino acid sequence
DIVMTQSPSSLSASVGDRVTITCKASQNVGTDVAWYQQKPGKAPKALIYWA
SNRFTGVPDRFTGSGSGTDFTLTISSLQAEDVADYFCQQYSSSPWTFGGGTKV
EIK SEQ ID NO: 26 - Humanized light chain variable region nucleic acid sequence
```
gacatcgtgatgacccagtcccccagctccctgtccgcctccgtgggcgacagagtgaccatcacatgcaaggcctccca
gaacgtgggcacagacgtggcctggtatcagcagaagcccggcaaggcccccaaggccctgatctactgggcctccaa
ccggttcaccggcgtgcccgacagattcaccggctctggctccggcaccgacttcaccctgaccatctccagcctgcag
gccgaggacgtggccgactacttctgccagcagtactcctccagcccctggaccttcggcggaggcaccaaggtggaaa
tcaag
```

SEQ ID NO: 27 - Humanized light chain variable region amino acid sequence
DIVMTQSPSSLSASVGDRVTITCKASQNVGTDVAWYQQKPGKAPKALIYWA
SNRFTGVPDRFSGSGSGTDFTLTISSLQAEDVADYFCQQYSSSPWTFGGGTKVEIK SEQ ID NO: 28 - Humanized light chain variable region nucleic acid sequence
```
gacatcgtgatgacccagtcccccagctccctgtccgcctccgtgggcgacagagtgaccatcacatgcaaggcctccca
gaacgtgggcacagacgtggcctggtatcagcagaagcccggcaaggcccccaaggccctgatctactgggcctccaaccg
gttcacggcgtgcccgacagattctccggctctggctccggcaccgacttcaccctgaccatctccagcctgcaggccga
ggacgtggccgactacttctgccagcagtactcctccagcccctggaccttcggcggaggcaccaaggtggaaatcaag
```

SEQ ID NO: 29 - Humanized light chain variable region amino acid sequence
DIQMTQSPSSLSASVGDRVTITCKASQNVGTDVAWYQQKPGKAPKALIYWA
SNRFTGVPDRFSGSGSGTDFTLTISSLQAEDVADYFCQQYSSSPWTFGGGTKV
EIK SEQ ID NO: 30 - Humanized light chain variable region nucleic acid sequence
```
gacatccagatgacccagtcccccagctccctgtccgcctccgtgggcgacagagtgaccatcacatgcaaggcctccca
gaacgtgggcaccgacgtggcctggtatcagcagaagcccggcaaggcccccaaggccctgatctactgggcctccaa
ccggttcaccggcgtgcccgacagattctccggctctggctccggcaccgacttcaccctgaccatctccagcctgcagg
ccgaggacgtggccgactacttctgccagcagtactcctccagcccctggaccttcggcggaggcaccaaggtggaaat
caag
```

SEQ ID NO: 31 - Amino acid sequence of an epitope on GRP78 polypeptide
QDADIEDFKAKKKELEEIVQPIISKLYGS SEQ ID NO: 32 - Amino acid sequence of an epitope on GRP78 polypeptide
LEEIVQPIISKLYGS

What is claimed is:

1. An isolated antibody or antigen-binding fragment thereof that binds to human cell surface glucose regulated protein 78 (GRP78)(SEQ ID NO: 1), wherein said antibody or antigen-binding fragment binds to an epitope depicted in SEQ ID NO: 31 comprises a heavy chain variable region and a light chain variable region selected from the group consisting of the following pairs of sequences: SEQ ID NO: 13 and SEQ ID NO: 23; SEQ ID NO: 15 and SEQ ID NO: 27; SEQ ID NO: 17 and SEQ ID NO: 25; SEQ ID NO: 19 and SEQ ID NO: 25; SEQ ID NO: 19 and SEQ ID NO: 29; or SEQ ID NO: 21 and SEQ ID NO: 23.

2. An isolated antibody or antigen-binding fragment thereof according to claim 1, wherein said antibody or antigen-binding fragment thereof is less immunogenic in a human subject than the monoclonal antibody which comprises heavy chain variable region consisting of SEQ ID NO: 9 and a light chain variable region consisting of SEQ ID NO: 11;

wherein said antibody or antigen-binding fragment thereof binds said cell surface GRP78 with a similar or greater binding affinity than the monoclonal antibody which comprises a heavy chain variable region consisting of SEQ ID NO: 9 and a light chain variable region consisting of SEQ ID NO: 11; and/or wherein said antibody or antigen-binding fragment thereof binds to said cell surface GRP78 with a dissociation constant ($K_D$) of at least about $1\times10^{-3}$ M, at least about $1\times10^{-4}$ M, at least about $1\times10^{-5}$ M, at least about $1\times10^{-6}$ M, at least about $1\times10^{-7}$ M, at least about $1\times10^{-8}$ M, at least about $1\times10^{-9}$ M, at least about $1\times10^{-10}$ M, at least about $1\times10^{-11}$ M, or at least about $1\times10^{-12}$ M.

3. An isolated antibody or antigen-binding fragment thereof according to claim 1, wherein said antibody or antigen-binding fragment thereof is a polyclonal antibody, a monoclonal antibody or antigen-binding fragment thereof, a recombinant antibody, a diabody, a chimerized or chimeric antibody or antigen-binding fragment thereof, a humanized antibody or antigen-binding fragment thereof, a fully human antibody or antigen-binding fragment thereof, a CDR-grafted antibody or antigen-binding fragment thereof, a single chain antibody, an Fv, an Fd, an Fab, an Fab', or an F(ab')$_2$, or synthetic or semi-synthetic antibodies.

4. A pharmaceutical composition comprising an antibody or antigen-binding fragment thereof according to claim 1 in pharmaceutically acceptable carriers or excipients.

5. An isolated antibody or antigen-binding fragment thereof according to claim 1, wherein said antibody or antigen-binding fragment is labeled, wherein said label is a fluorescent label, a radioactive label, or a label having a distinctive nuclear magnetic resonance signature.

6. An isolated immunoconjugate comprising an antibody or antigen-binding fragment according to claim 1 linked to an effector molecule.

7. An immunoconjugate of claim 6, wherein the effector molecule is an immunotoxin, cytokine, chemokine, therapeutic agent, or a chemotherapeutic agent.

\* \* \* \* \*